(12) United States Patent
Samsoondar

(10) Patent No.: US 10,661,270 B2
(45) Date of Patent: *May 26, 2020

(54) DISPOSABLE CARTRIDGE SYSTEM FOR POINT-OF-CARE TESTING

(71) Applicant: INVIDX CORP., Markham, Ontario (CA)

(72) Inventor: James Samsoondar, Markham (CA)

(73) Assignee: INVIDX CORP., Markham, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/296,539

(22) Filed: Mar. 8, 2019

(65) Prior Publication Data

US 2019/0224667 A1 Jul. 25, 2019

Related U.S. Application Data

(63) Continuation-in-part of application No. 15/995,895, filed on Jun. 1, 2018, now Pat. No. 10,272,430, which
(Continued)

(51) Int. Cl.
*B01L 3/00* (2006.01)
*G01N 33/49* (2006.01)

(52) U.S. Cl.
CPC ......... *B01L 3/502* (2013.01); *B01L 3/502715* (2013.01); *B01L 3/502738* (2013.01);
(Continued)

(58) Field of Classification Search
CPC .............. B01L 3/502; B01L 3/502715; B01L 3/502753; B01L 3/502738; B01L 3/523; B01L 2300/0864; B01L 2300/0681; B01L 2200/04; B01L 2300/048; B01L 2200/0689; B01L 2400/049; B01L 2400/0487; B01L 2200/0684; B01L 2300/043; B01L 2300/042; G01N 33/4905

See application file for complete search history.

(56) References Cited

U.S. PATENT DOCUMENTS 4,514,091 A 4/1985 Kaspar et al.
4,722,714 A 2/1988 Marbourg, Jr.
(Continued)

FOREIGN PATENT DOCUMENTS

CA 2911318 A1 11/2015
WO 2016/049545 A1 3/2016

OTHER PUBLICATIONS

International Search Report and Written Opinion in International Application No. PCT/CA2017/050584, dated Jan. 15, 2018.

*Primary Examiner* — Sally A Merkling
(74) *Attorney, Agent, or Firm* — J.A. Lindeman & Co. PLLC

(57) ABSTRACT

Disposable cartridges comprising hinged caps and optical chambers for measuring one or more properties of a blood sample are described. Blood flow in the disposable cartridges may be regulated by either positive or negative pressure. Other embodiments of cartridges comprising a biosensor chamber disposed downstream of the optical chamber are also described. Methods for measuring one or more properties of a blood sample using different cartridge embodiments are provided.

27 Claims, 33 Drawing Sheets

Related U.S. Application Data is a continuation-in-part of application No. 15/680,736, filed on Aug. 18, 2017, now Pat. No. 9,999,884, which is a continuation of application No. PCT/CA2017/050584, filed on May 16, 2017, which is a continuation-in-part of application No. 15/356,630, filed on Nov. 20, 2016, now Pat. No. 9,821,307.

(60) Provisional application No. 62/258,520, filed on Nov. 22, 2015.

(52) U.S. Cl.
CPC ......... B01L 3/502753 (2013.01); B01L 3/523 (2013.01); G01N 33/4905 (2013.01); *B01L 2200/04* (2013.01); *B01L 2200/0684* (2013.01); *B01L 2200/0689* (2013.01); *B01L 2300/042* (2013.01); *B01L 2300/043* (2013.01); *B01L 2300/048* (2013.01); *B01L 2300/0681* (2013.01); *B01L 2300/0864* (2013.01); *B01L 2400/049* (2013.01); *B01L 2400/0487* (2013.01)

(56) References Cited

U.S. PATENT DOCUMENTS

| | | | |
|---|---|---|---|
| 6,077,233 A * | 6/2000 | Blake | G01N 33/4905 422/69 |
| 6,750,053 B1 | 6/2004 | Opalsky et al. | |
| 7,682,833 B2 * | 3/2010 | Miller | B01L 3/502707 422/537 |
| 9,470,673 B2 | 10/2016 | Samsoondar | |
| 2010/0196908 A1 * | 8/2010 | Opalsky | B01L 7/52 435/6.1 |

* cited by examiner

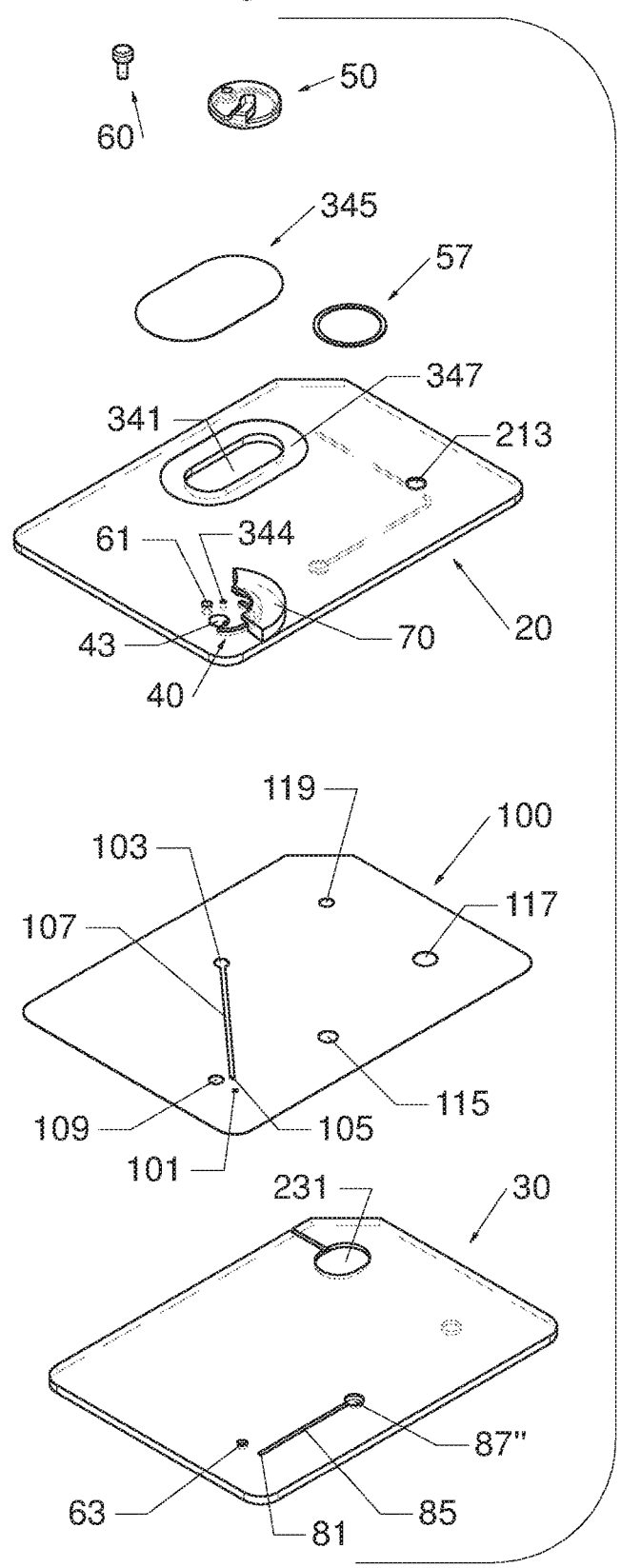
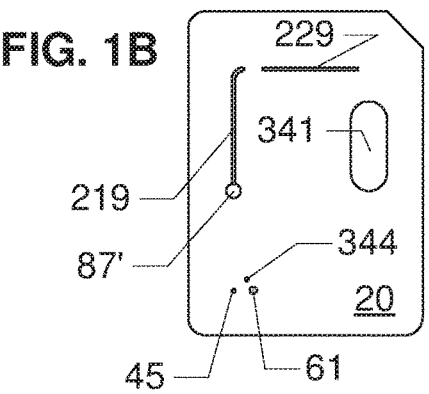
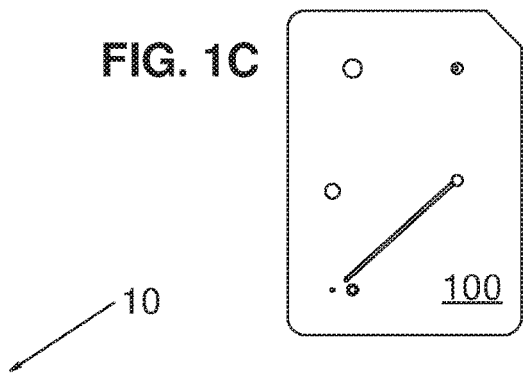
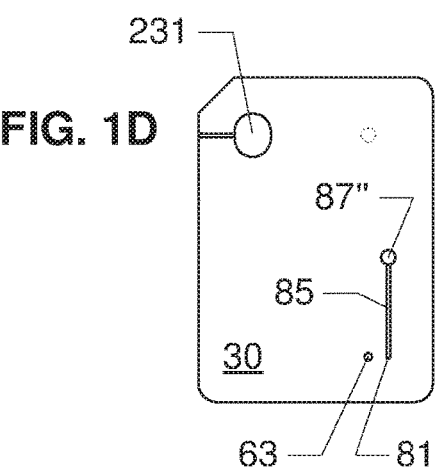
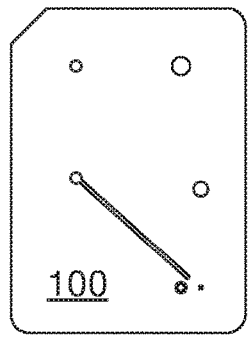

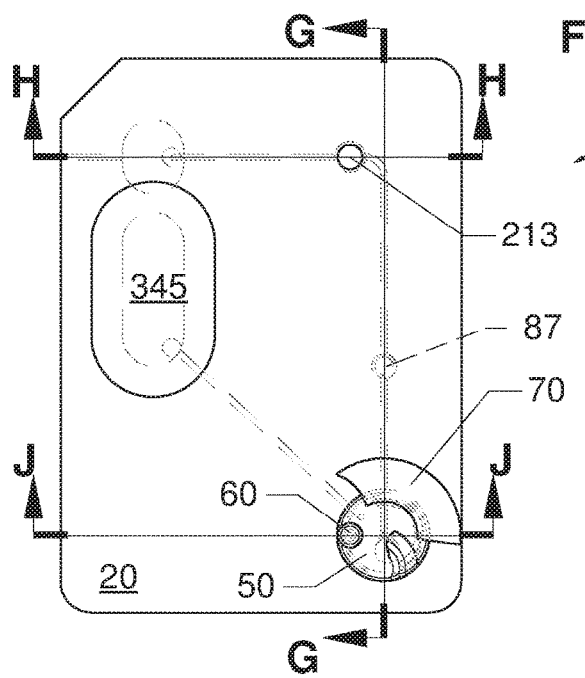
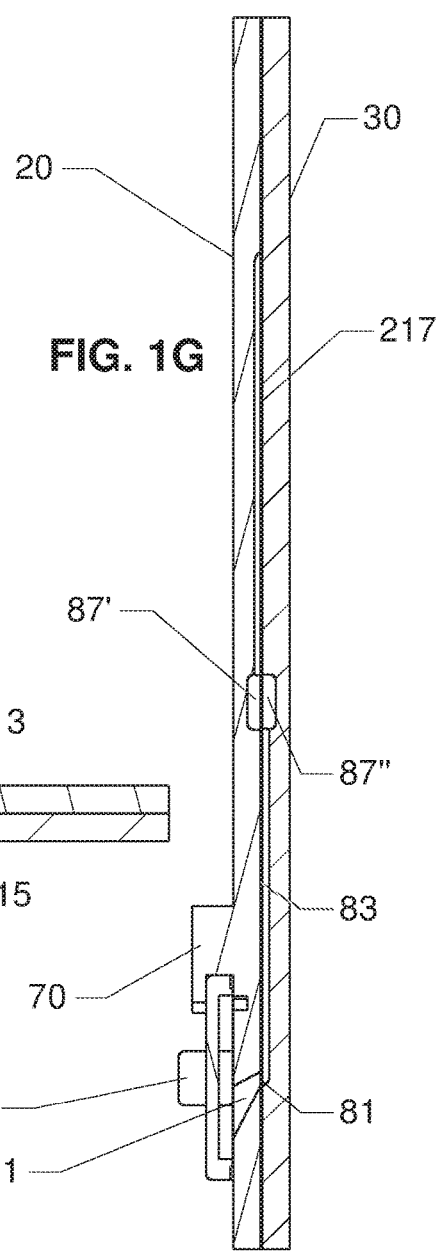
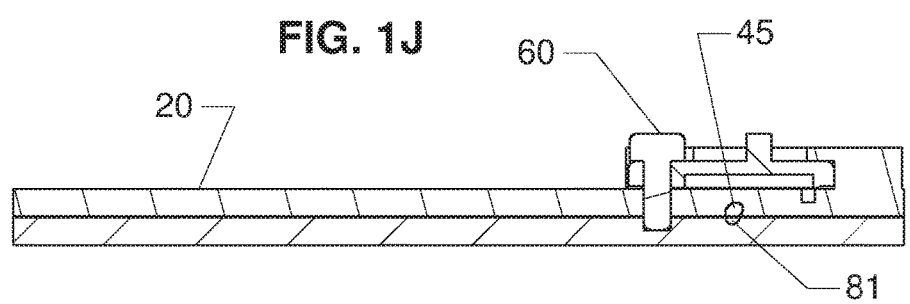

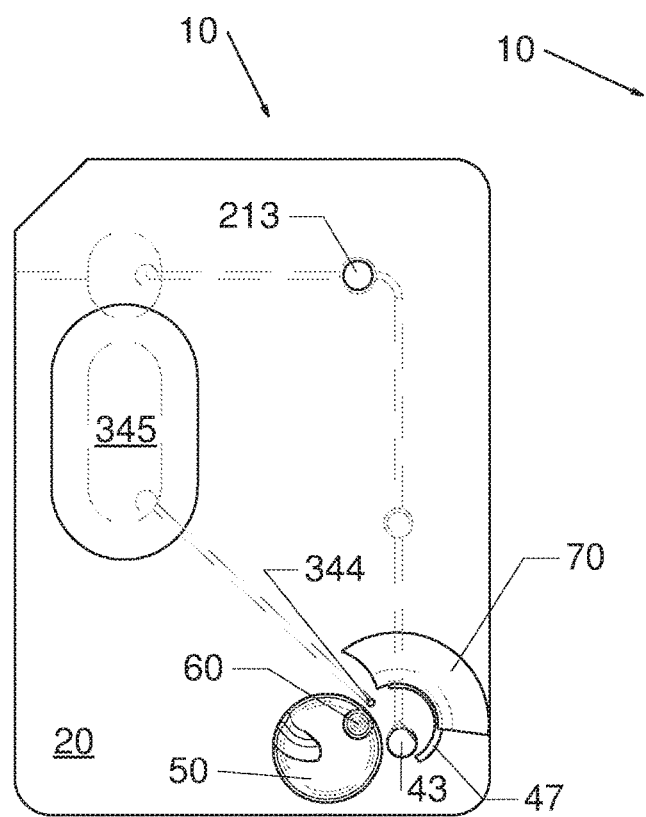
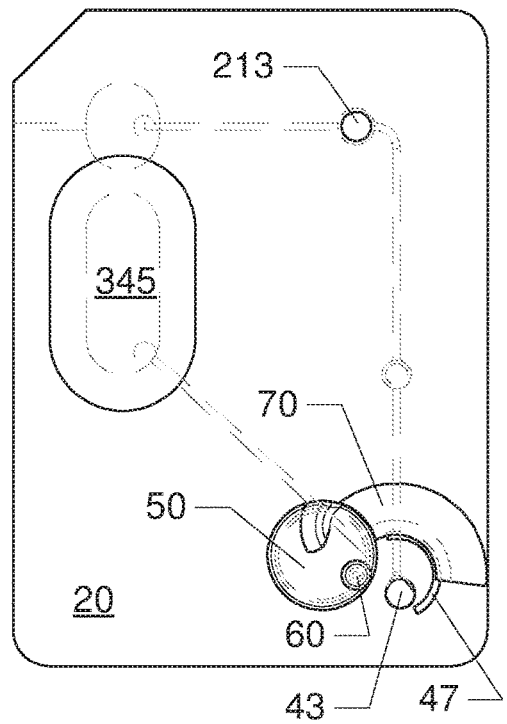
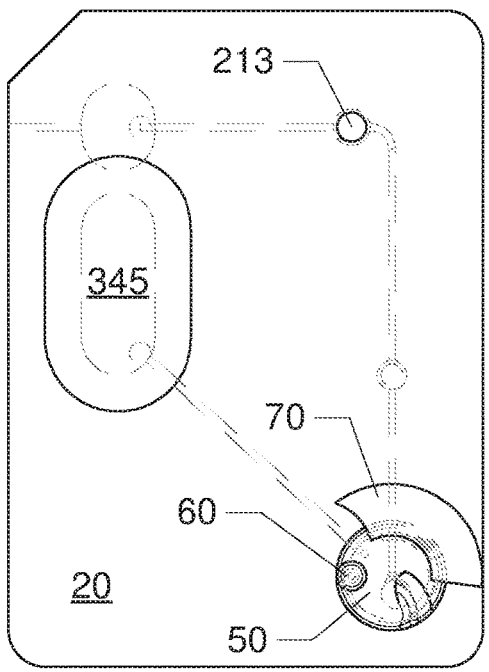

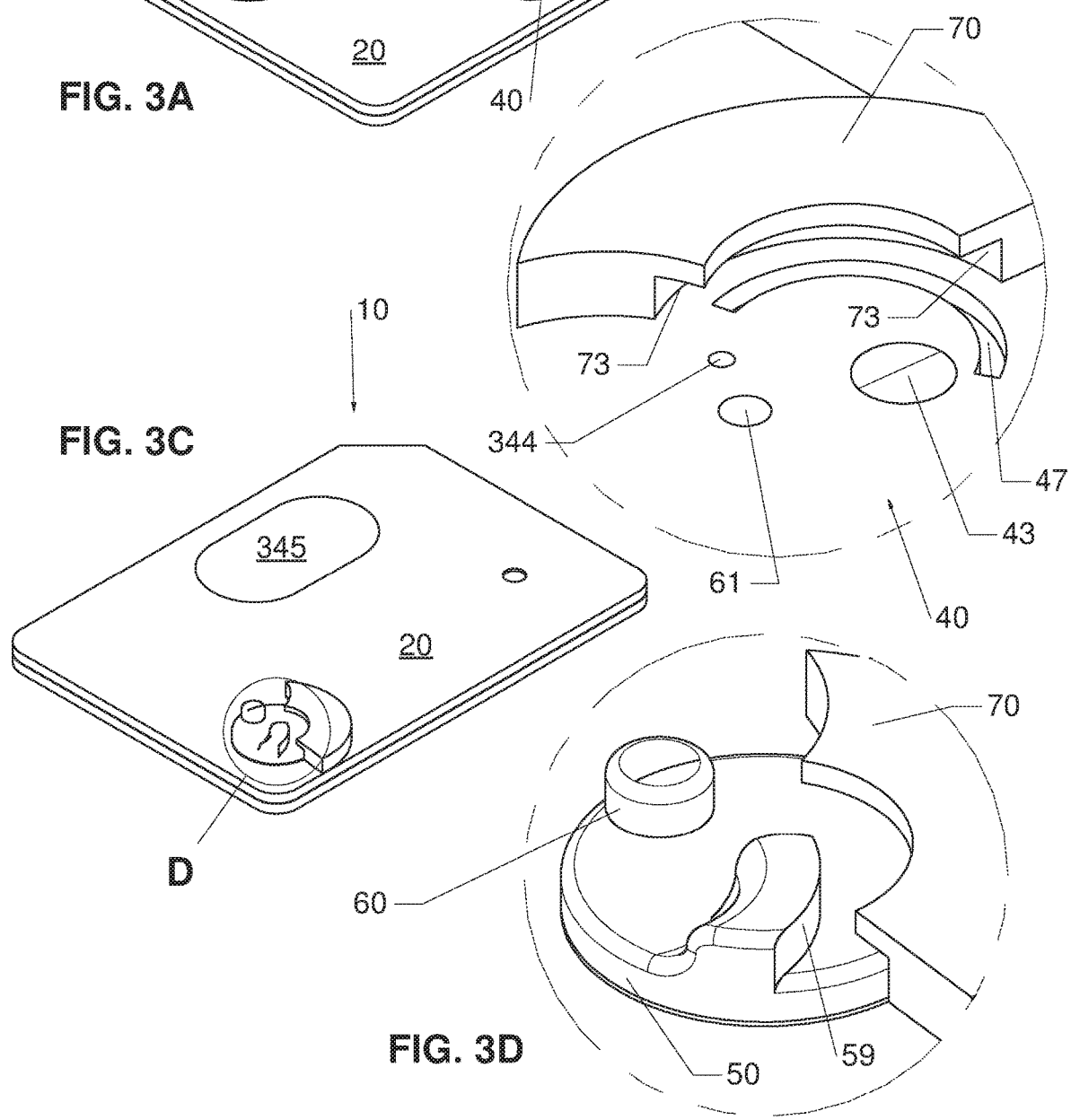

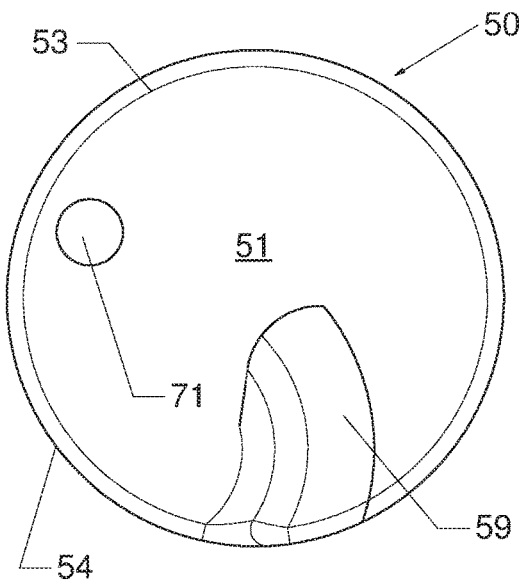
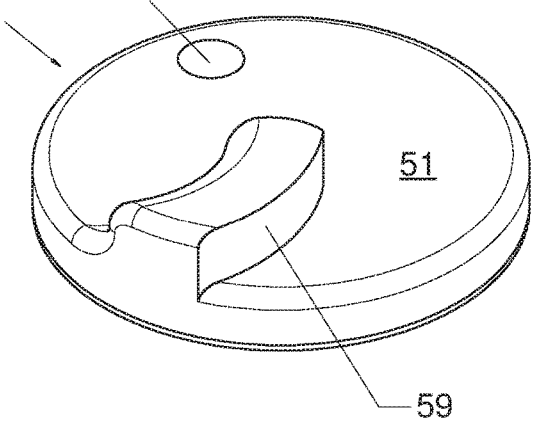
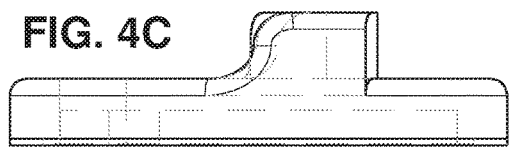
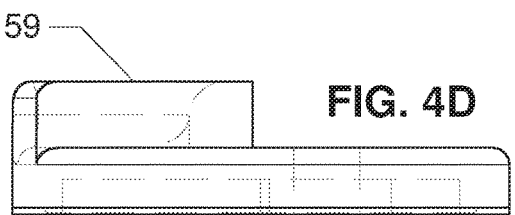
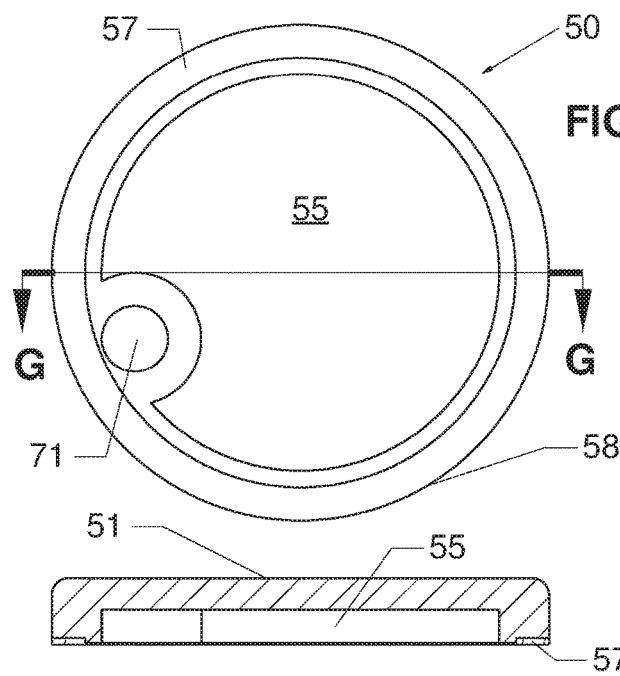
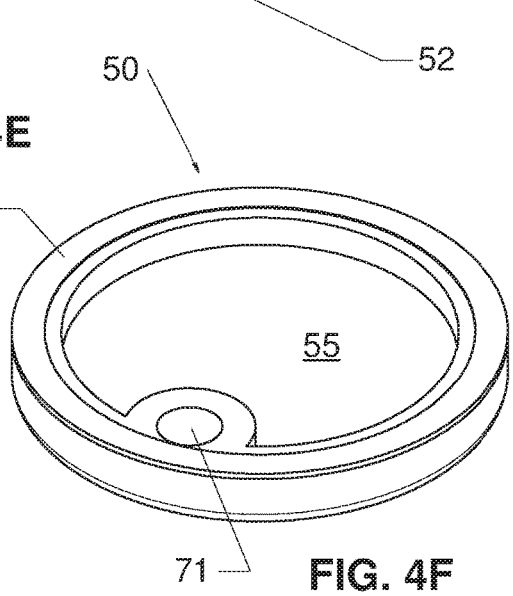

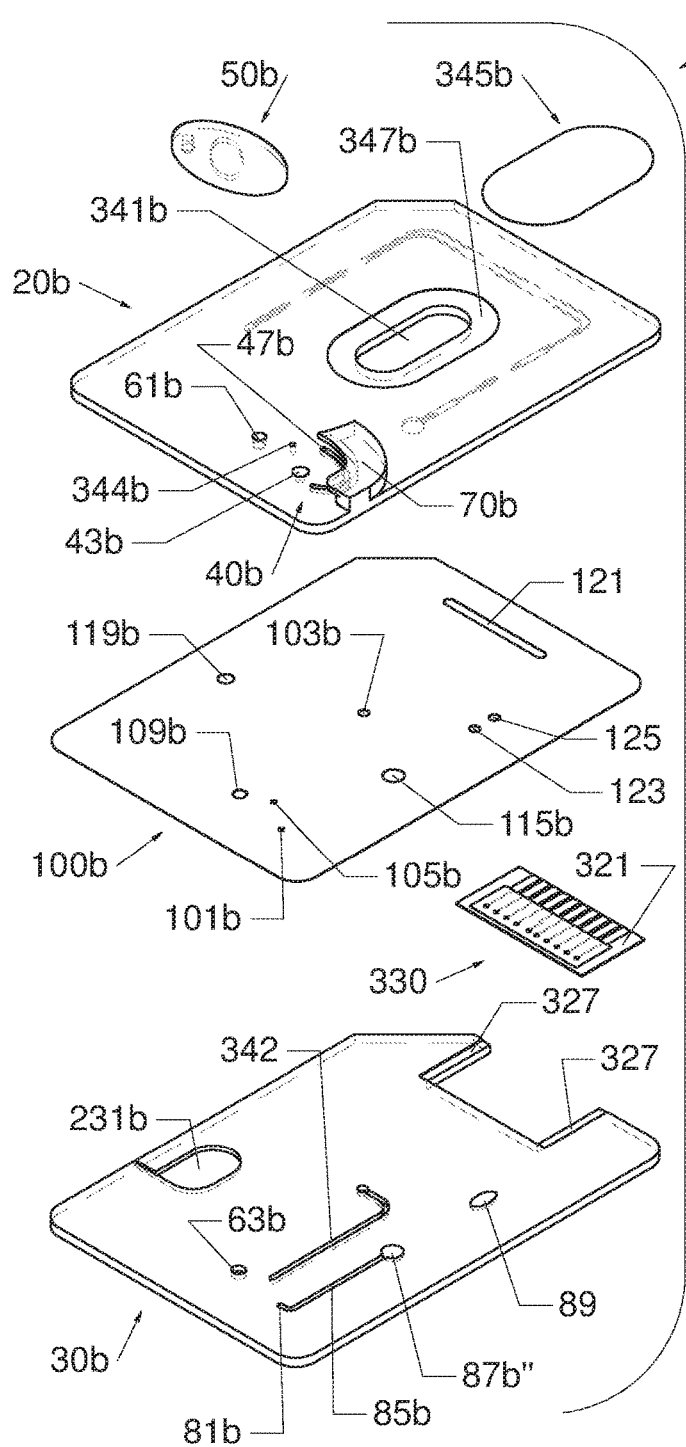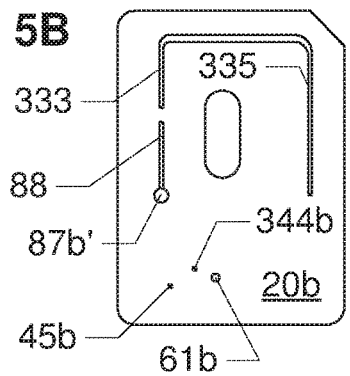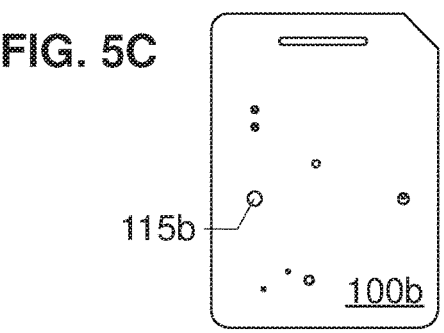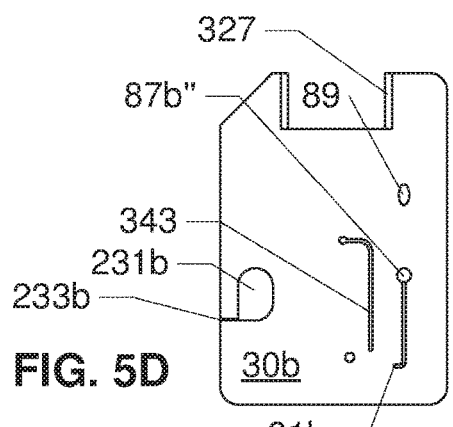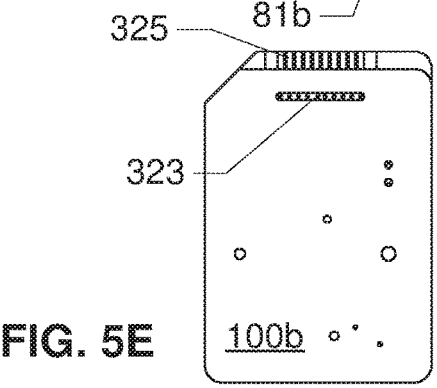

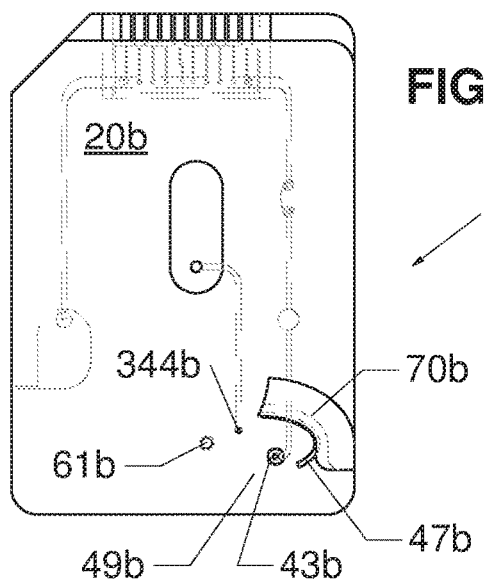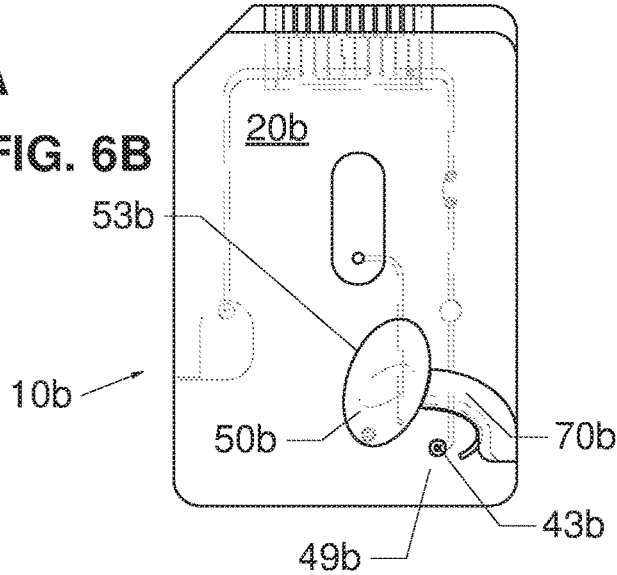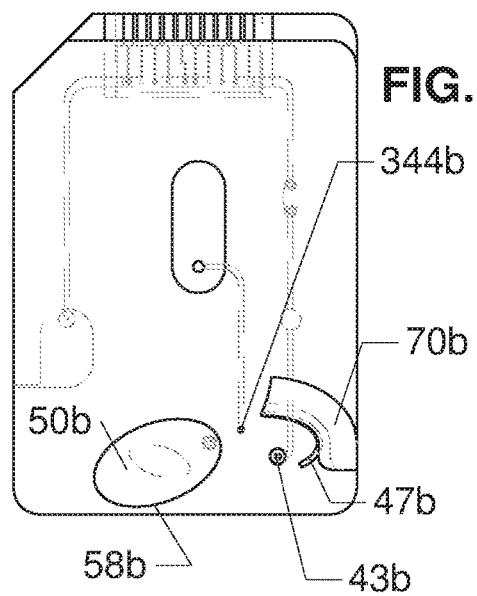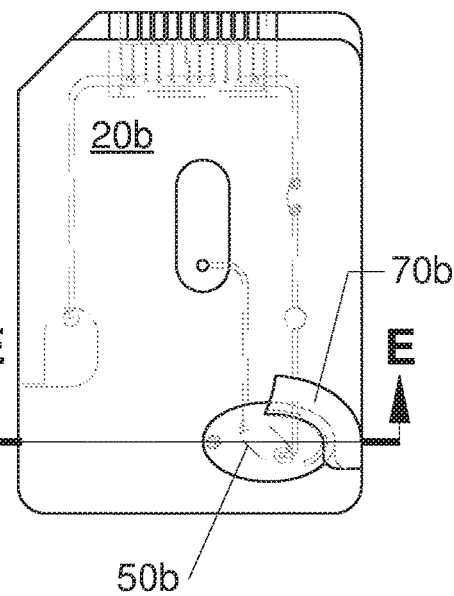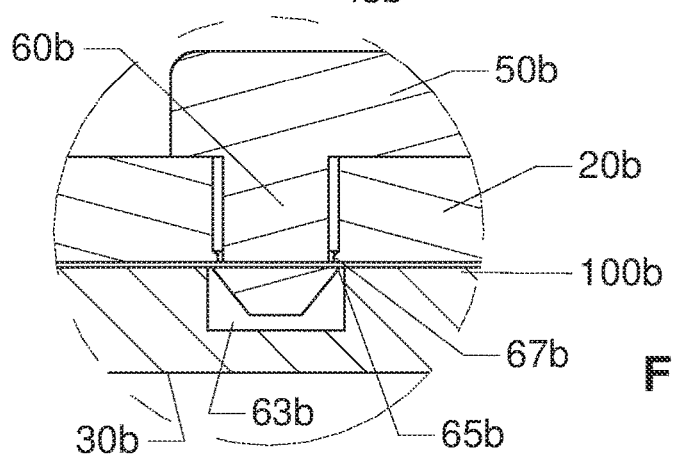

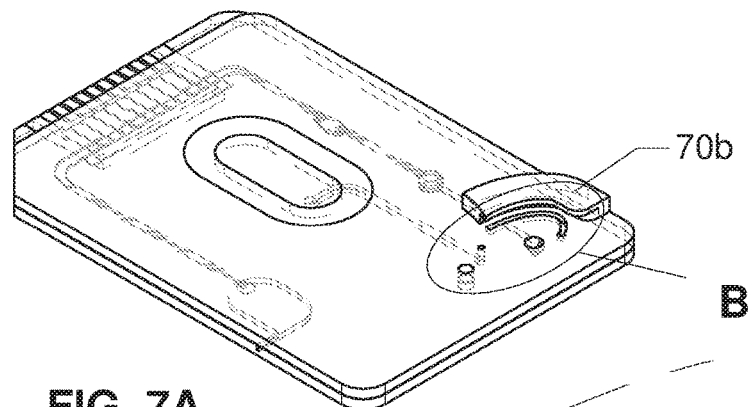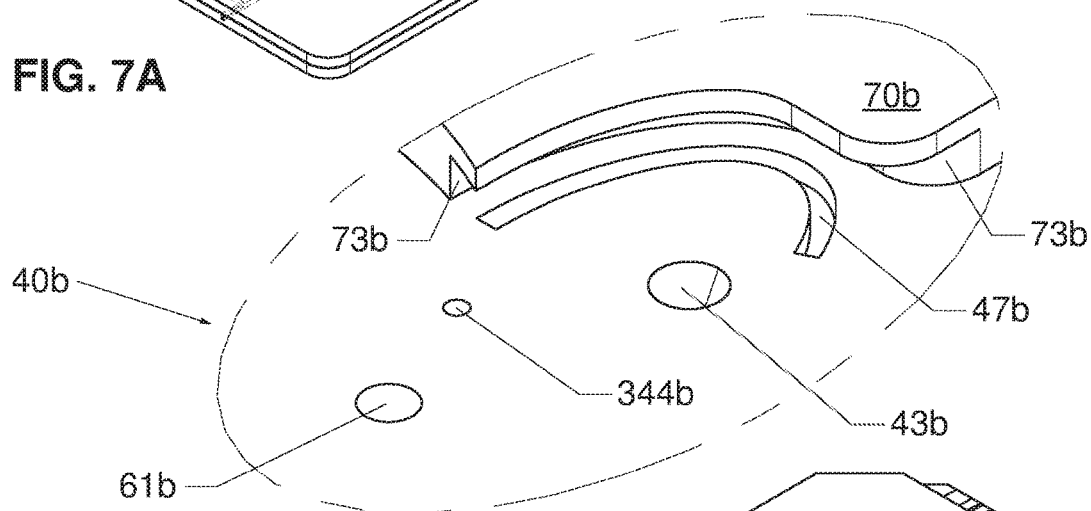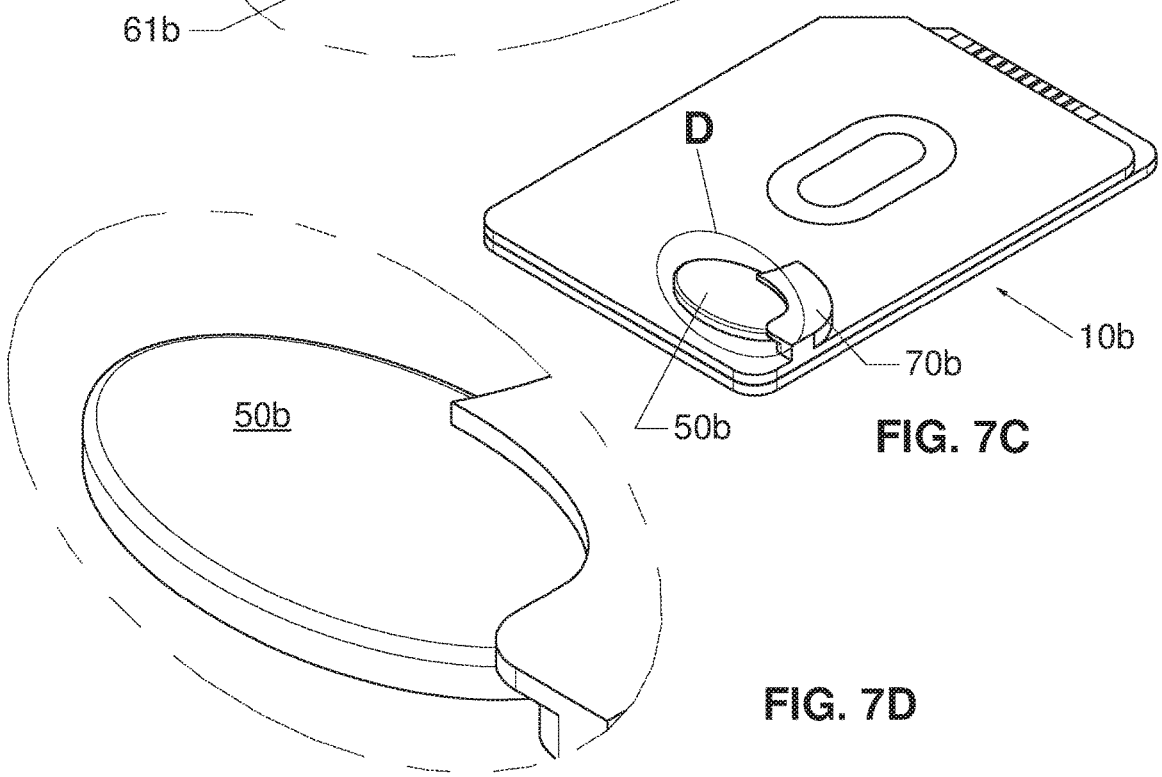

FIG. 8A
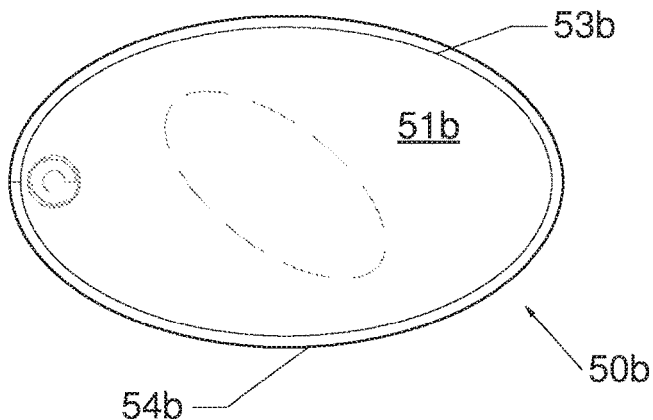
FIG. 8B
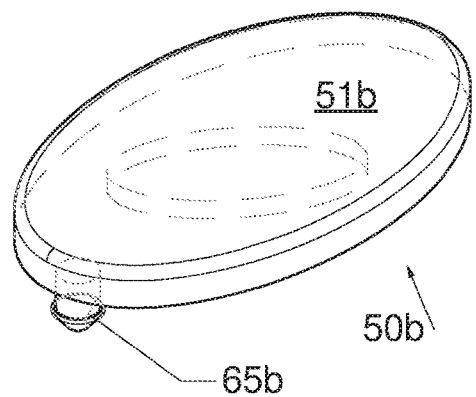
FIG. 8C
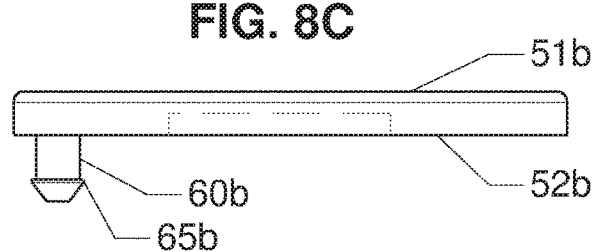
FIG. 8D
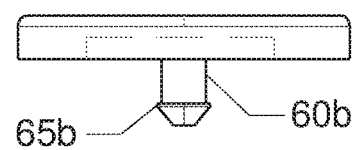
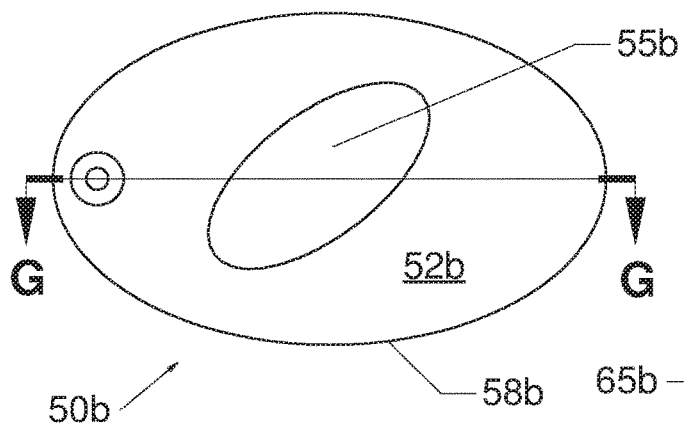
FIG. 8E
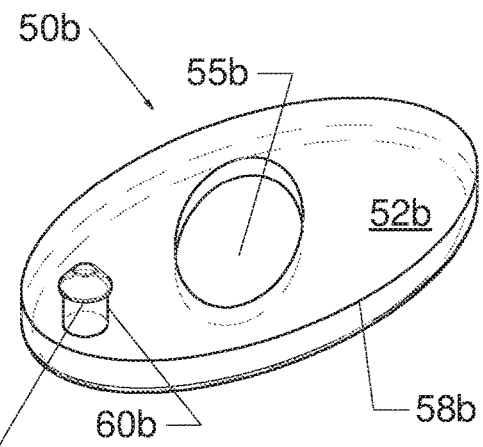
FIG. 8F
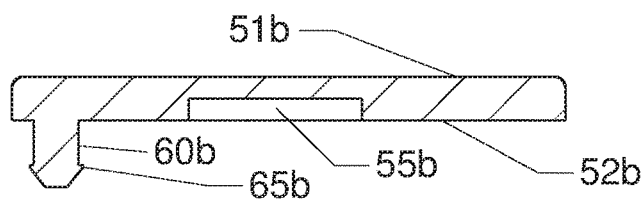
FIG. 8G

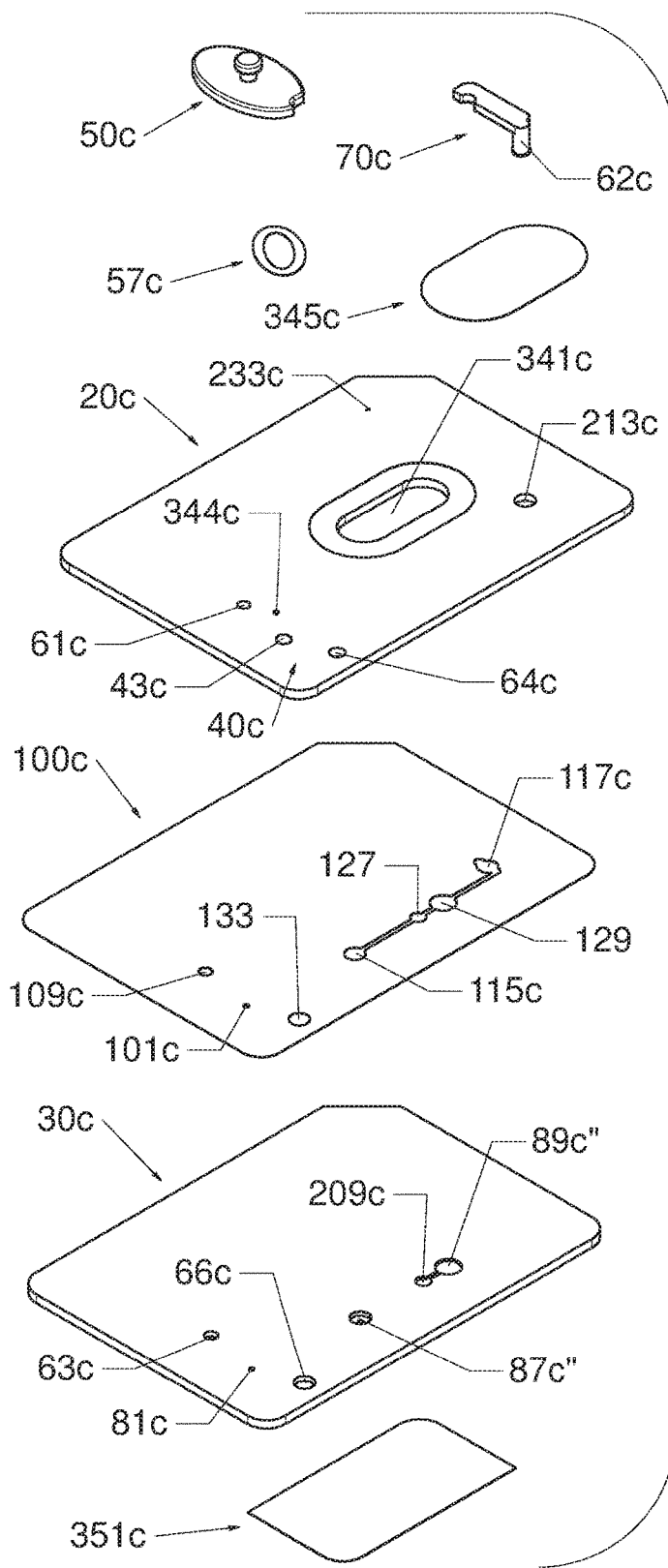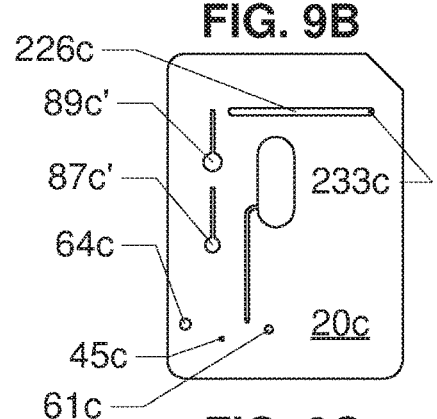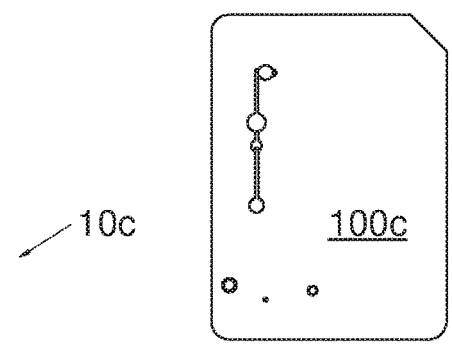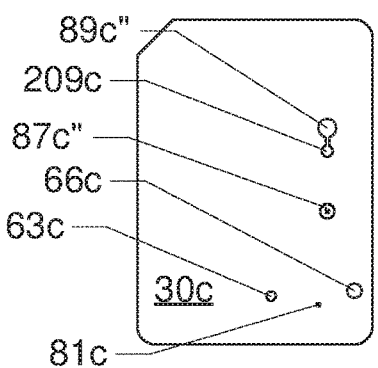

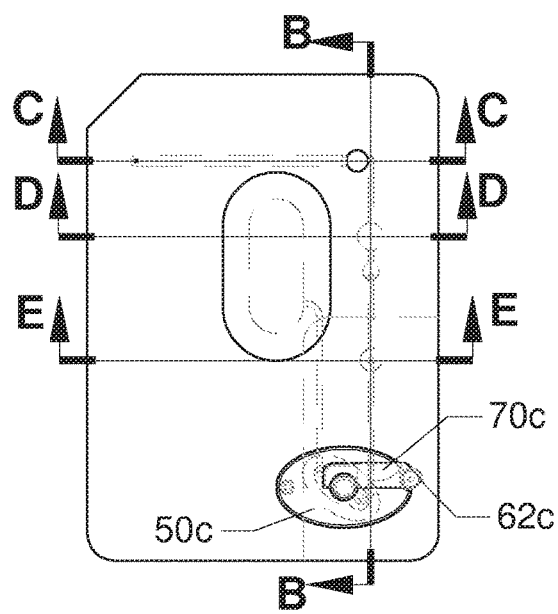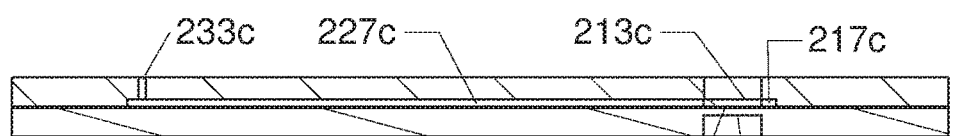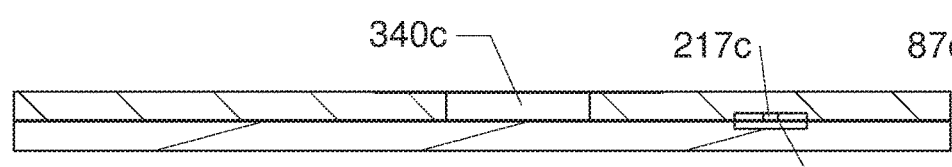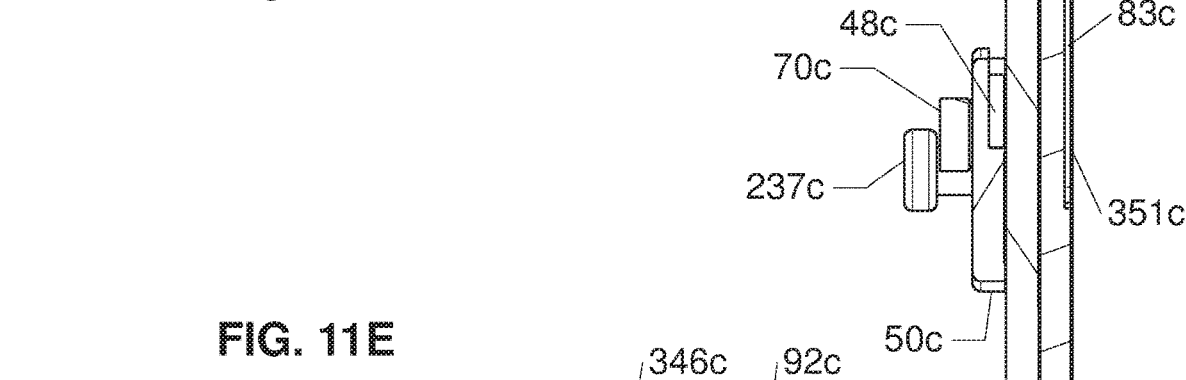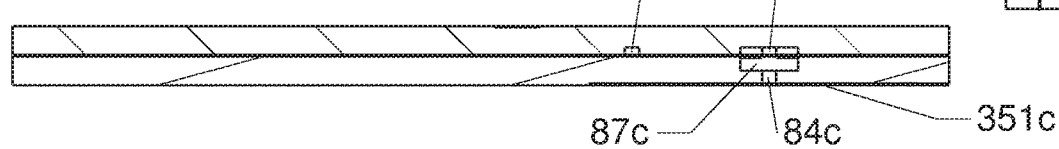

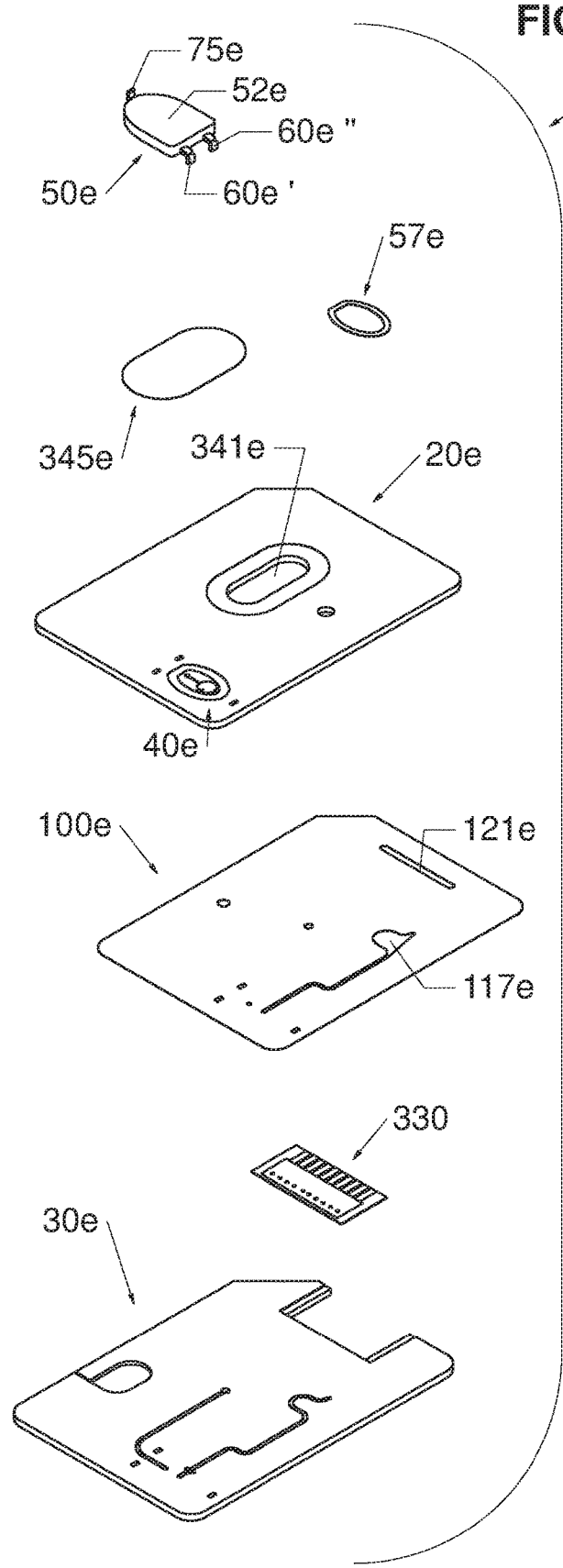
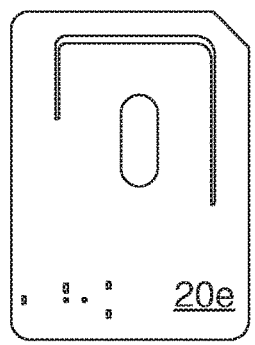
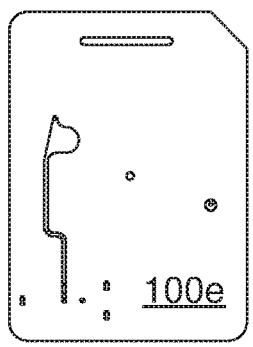
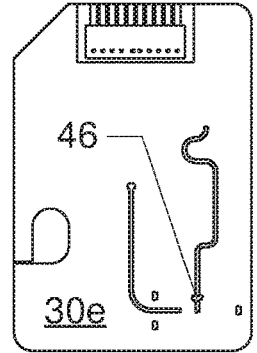
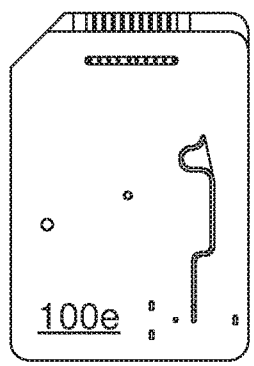

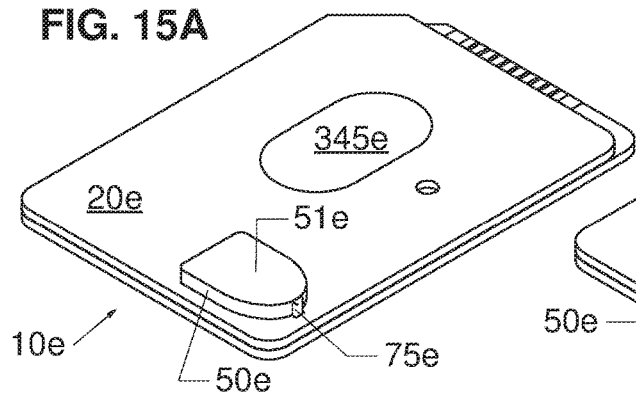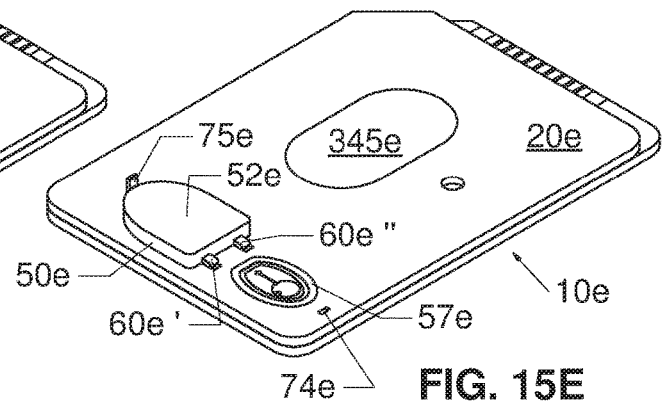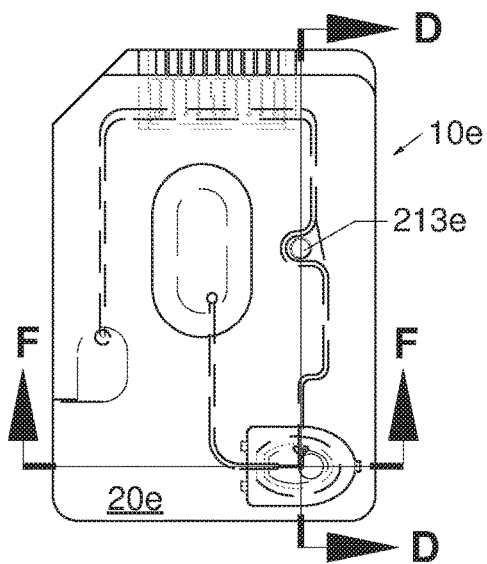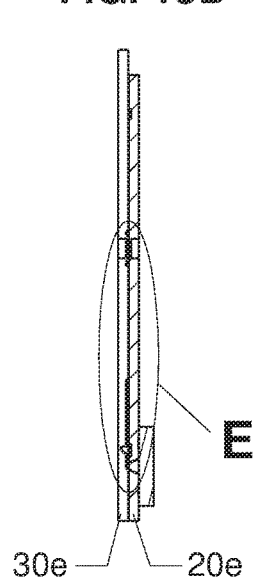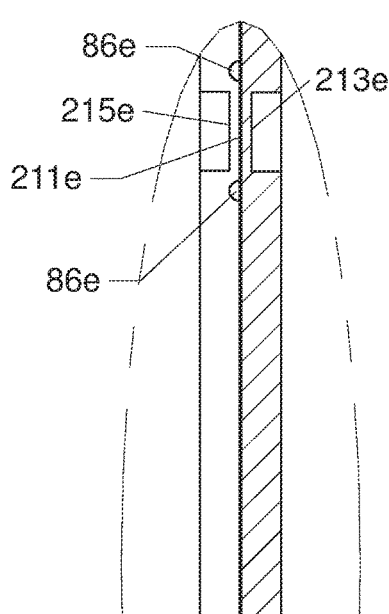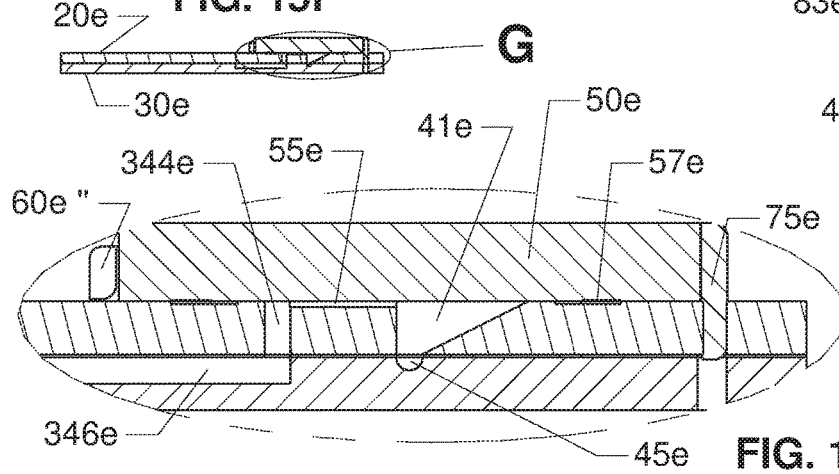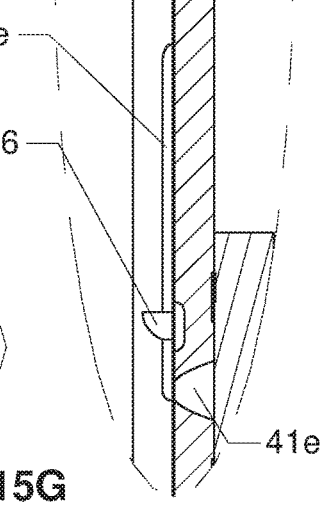

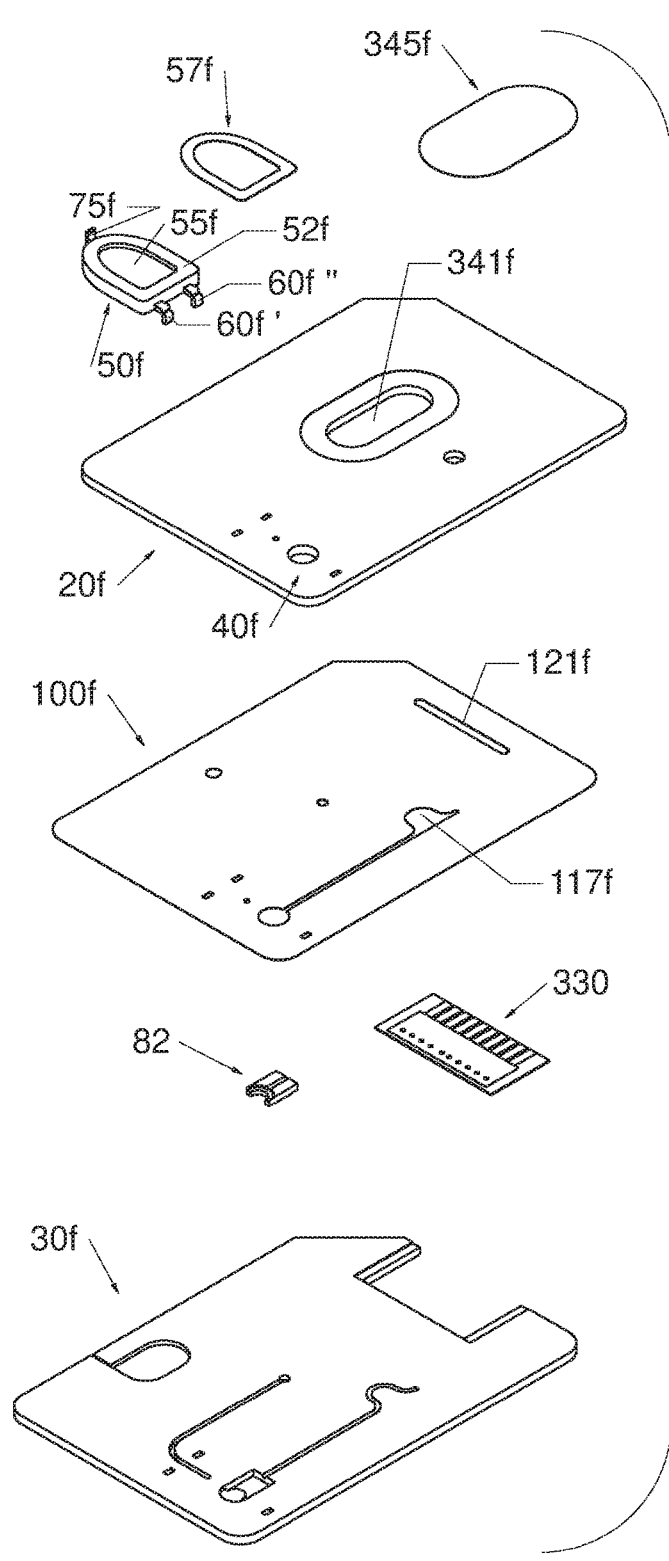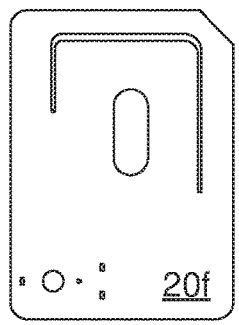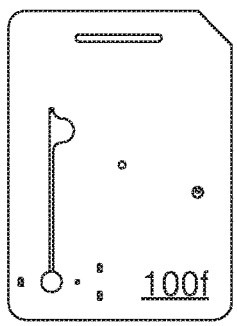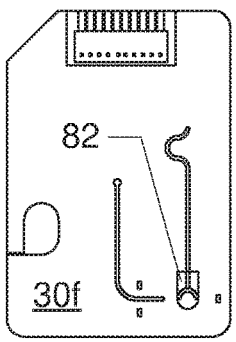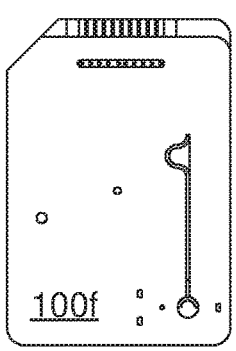

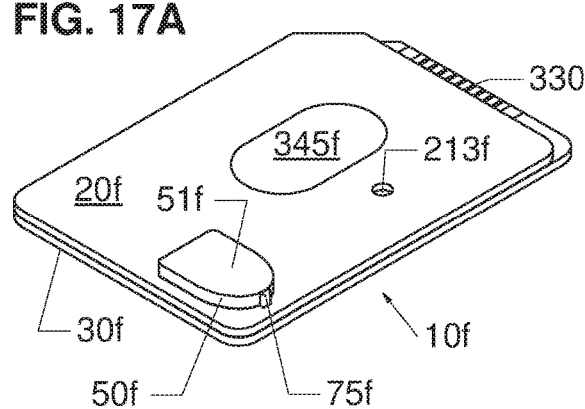
FIG. 17A
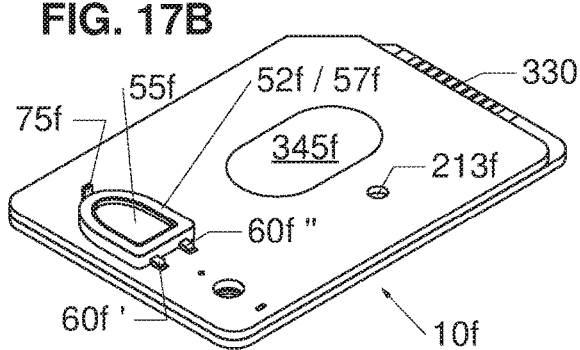
FIG. 17B
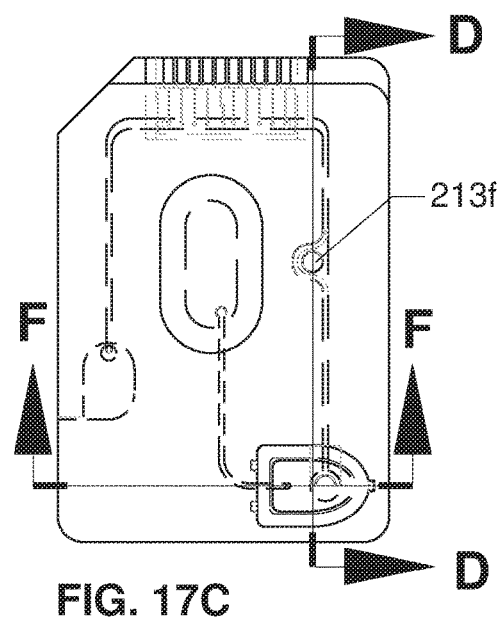
FIG. 17C
FIG. 17D
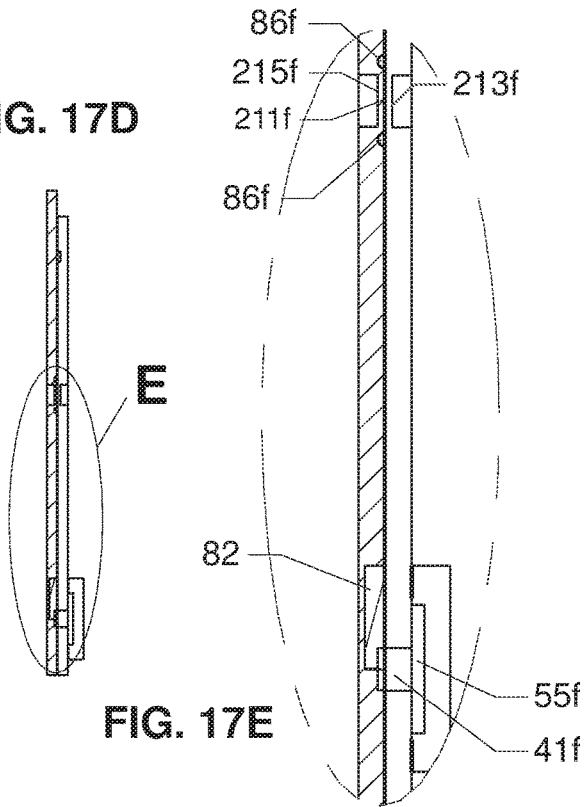
FIG. 17E
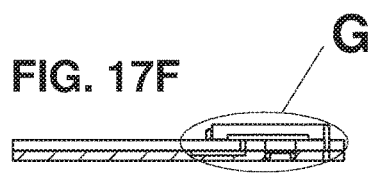
FIG. 17F
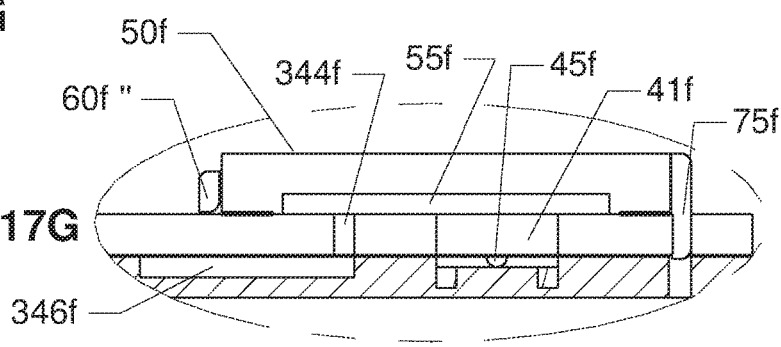
FIG. 17G

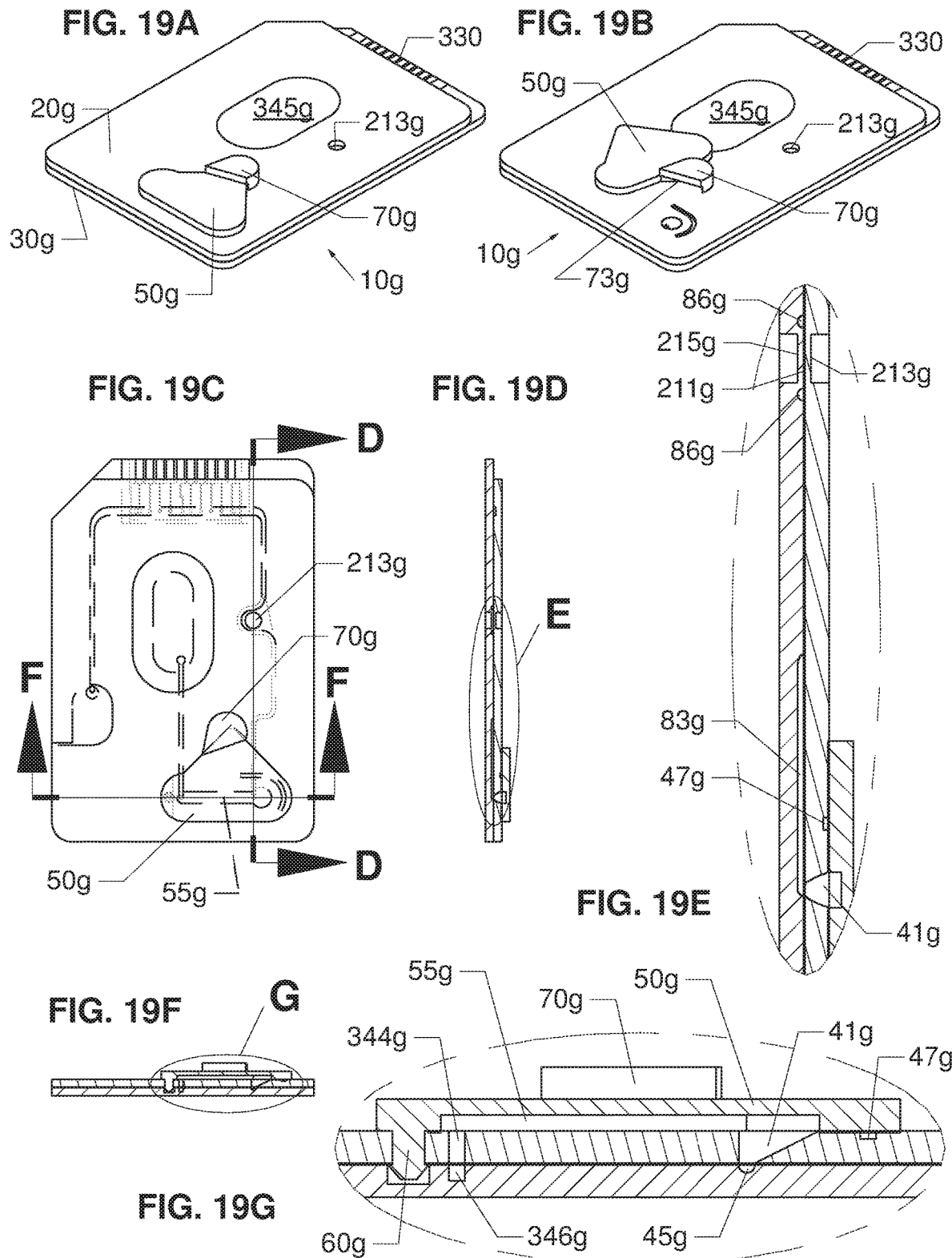

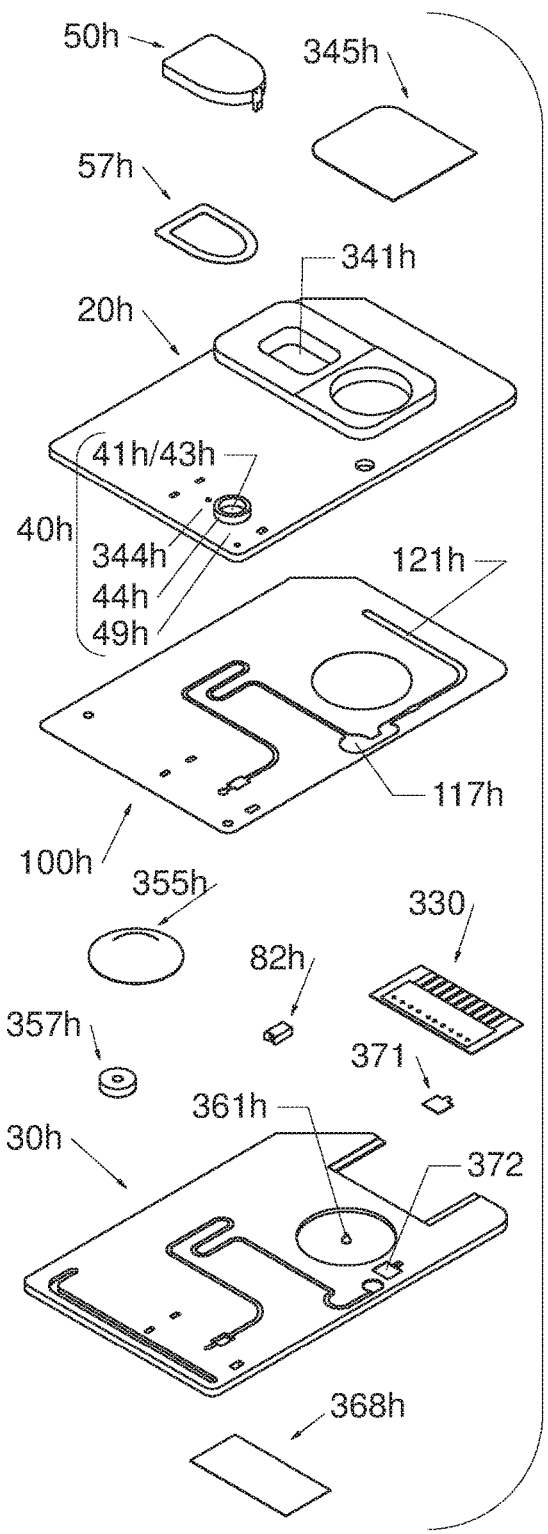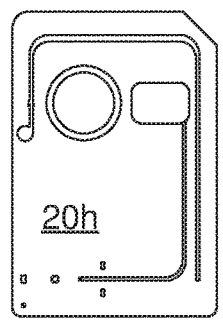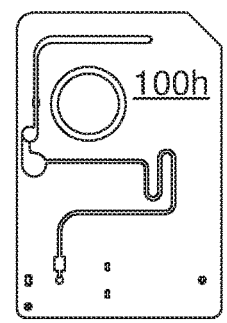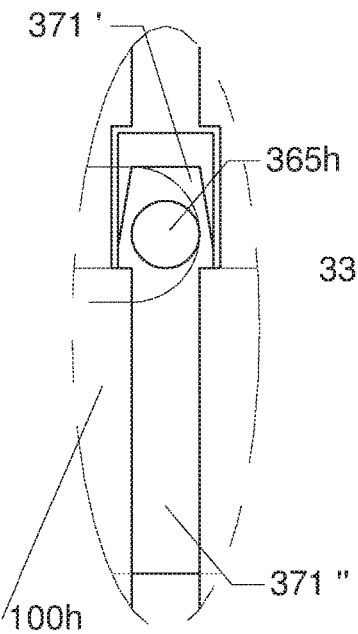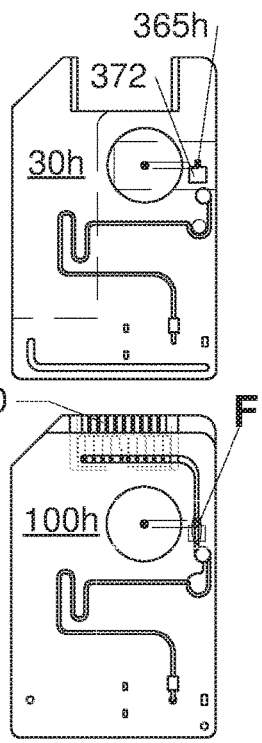

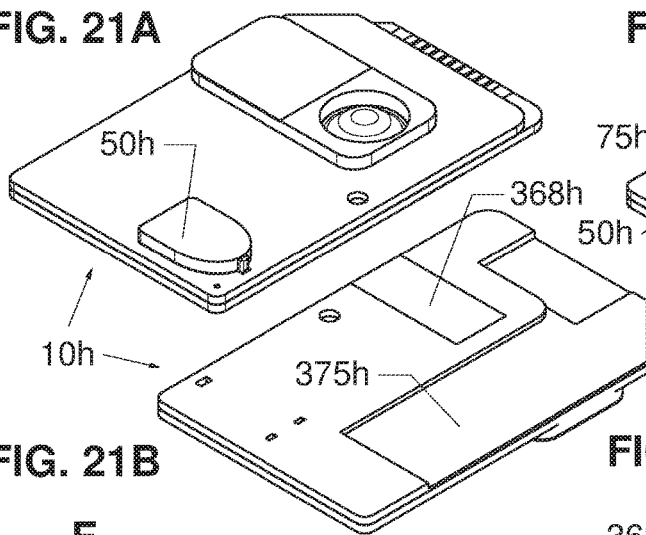
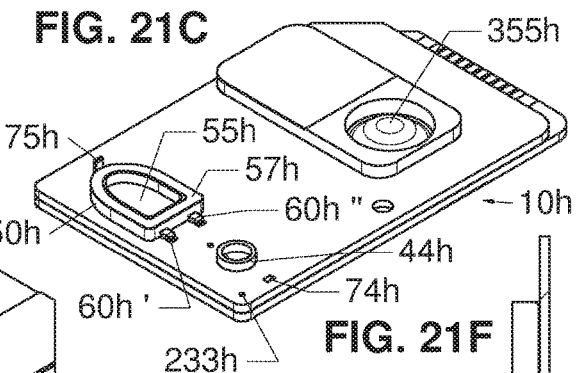
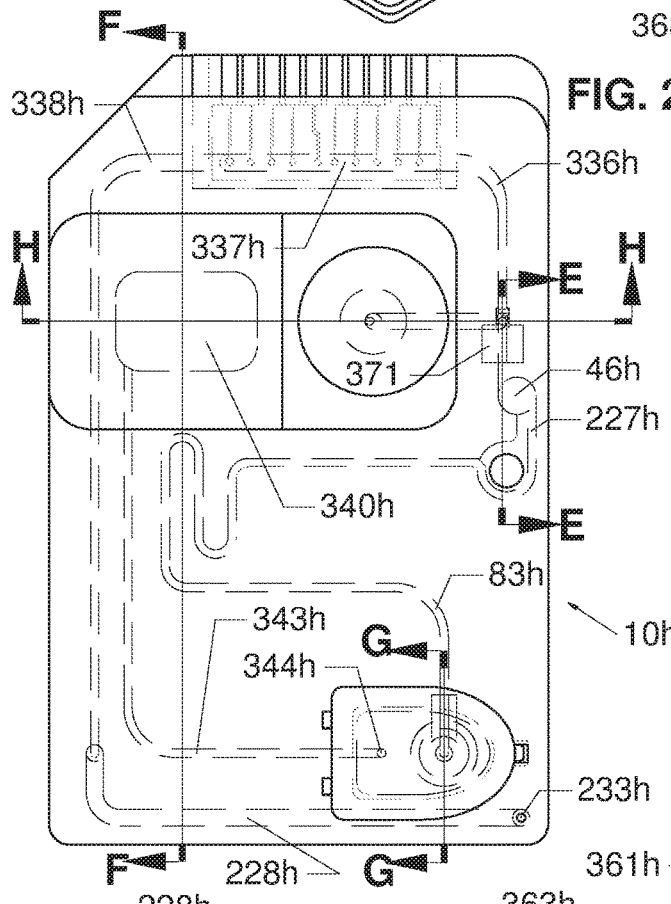
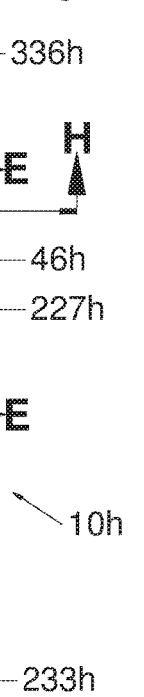
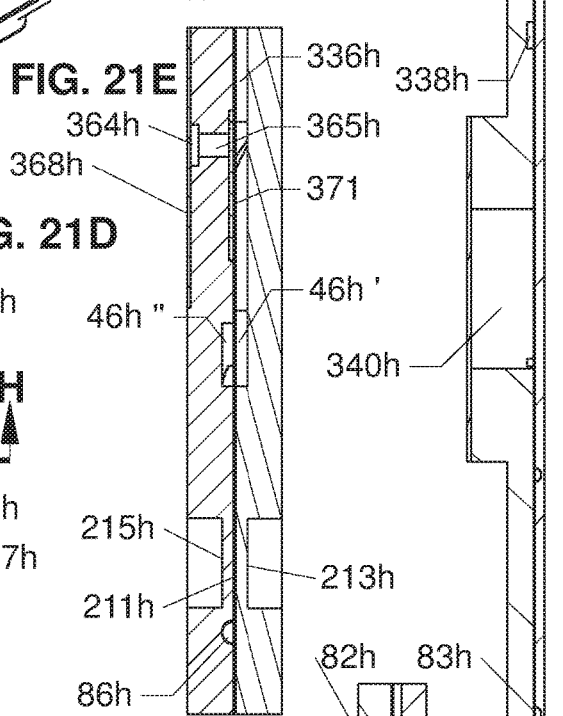
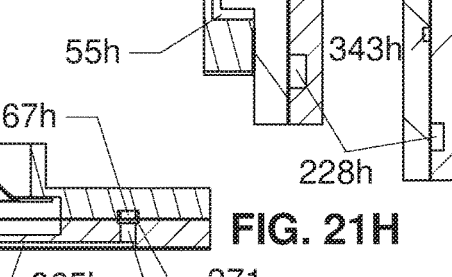
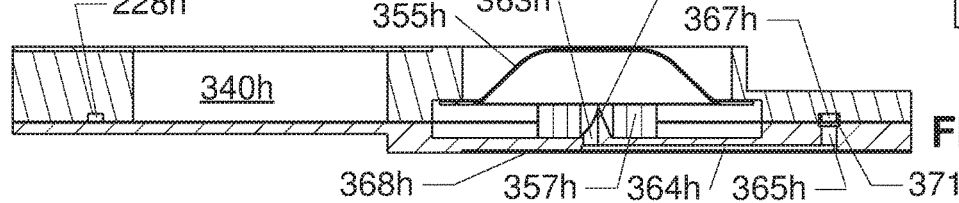

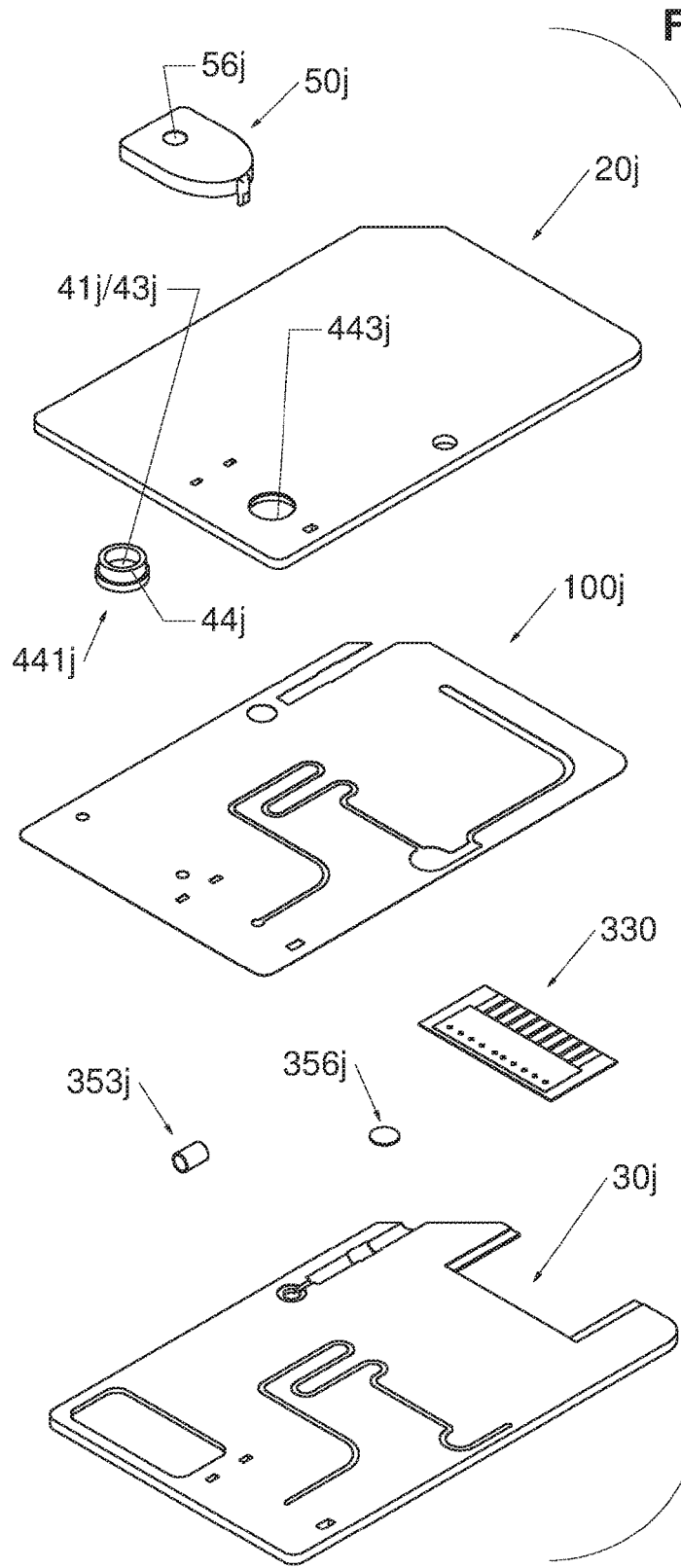
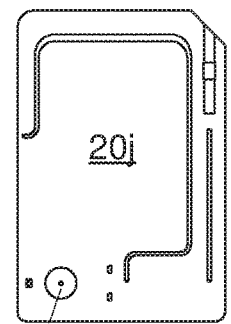
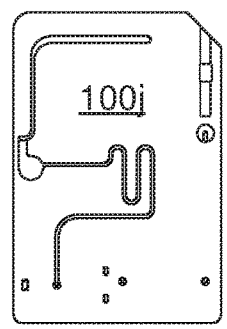
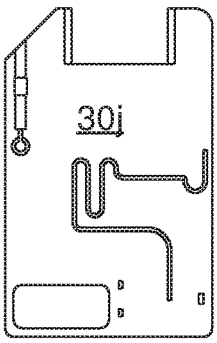
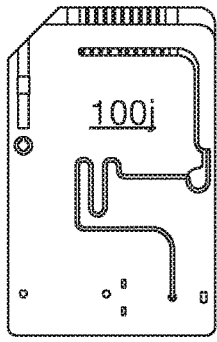

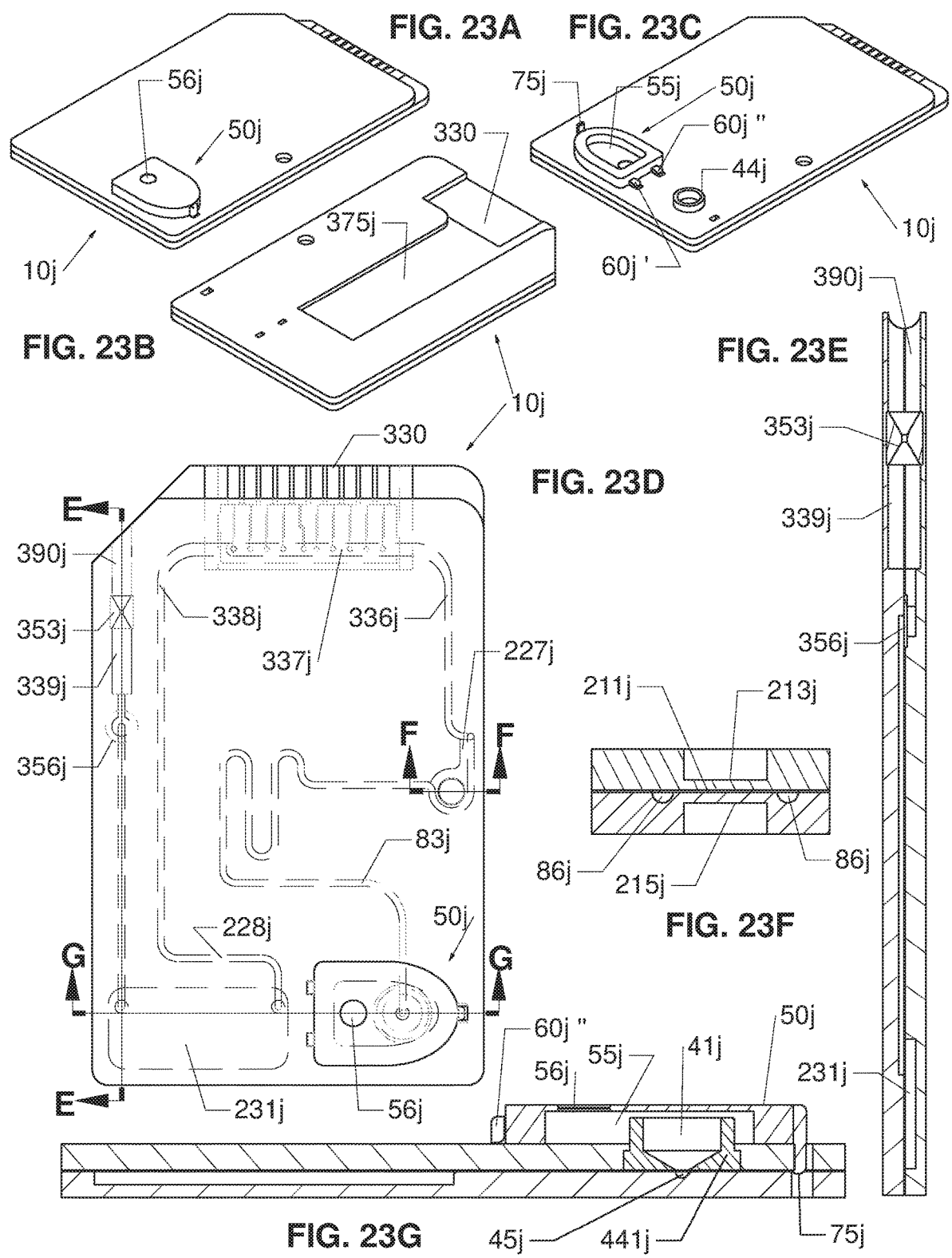

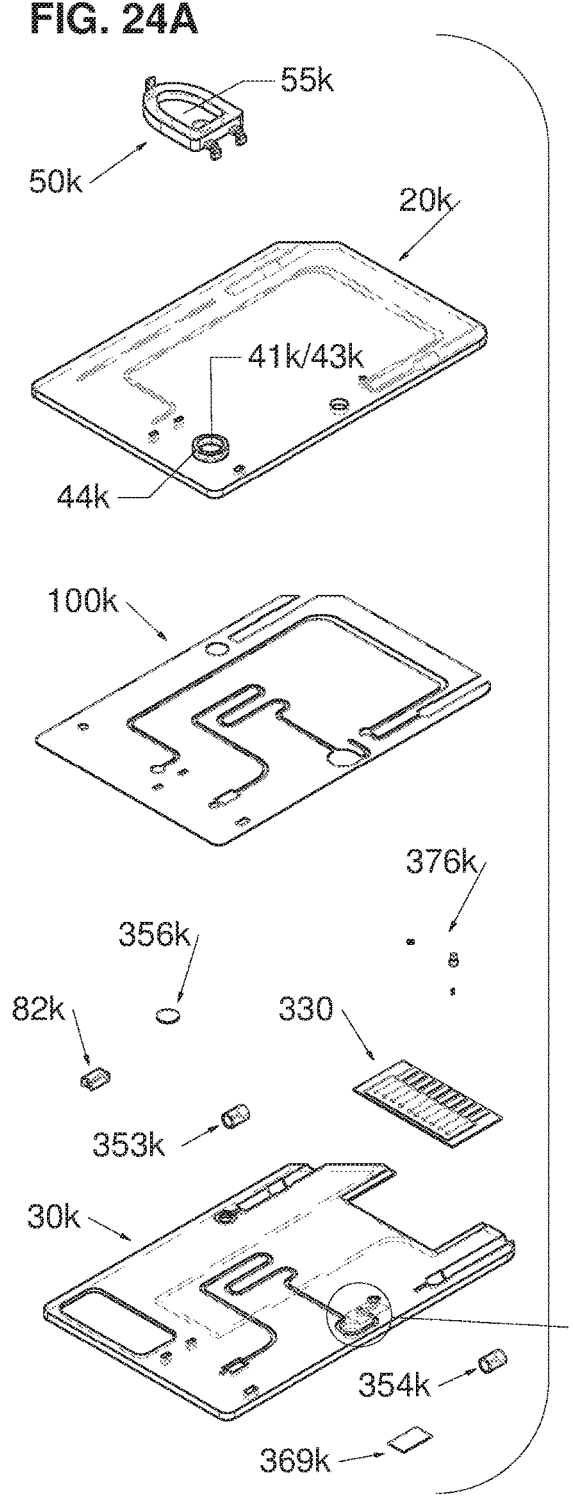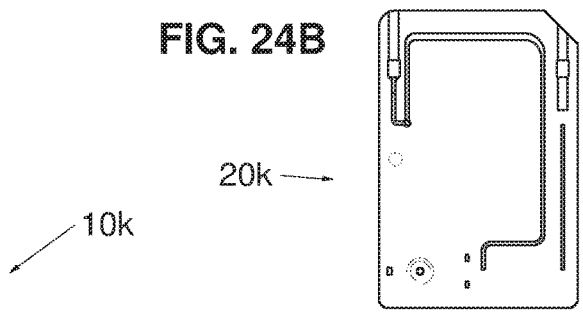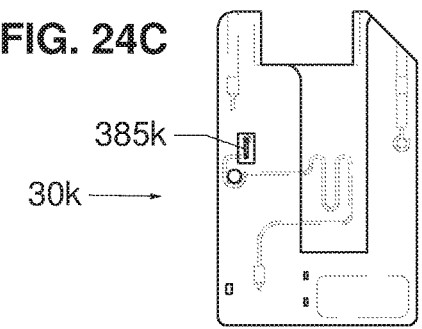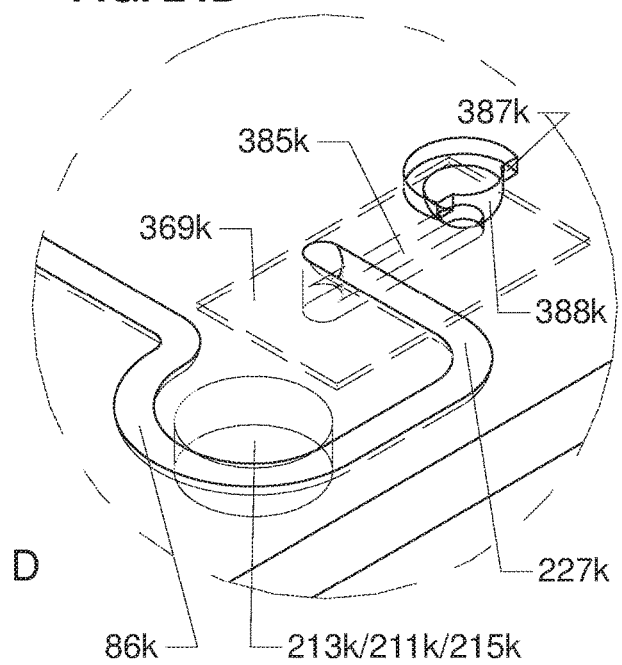
FIG. 24A
FIG. 24B
FIG. 24C
FIG. 24D

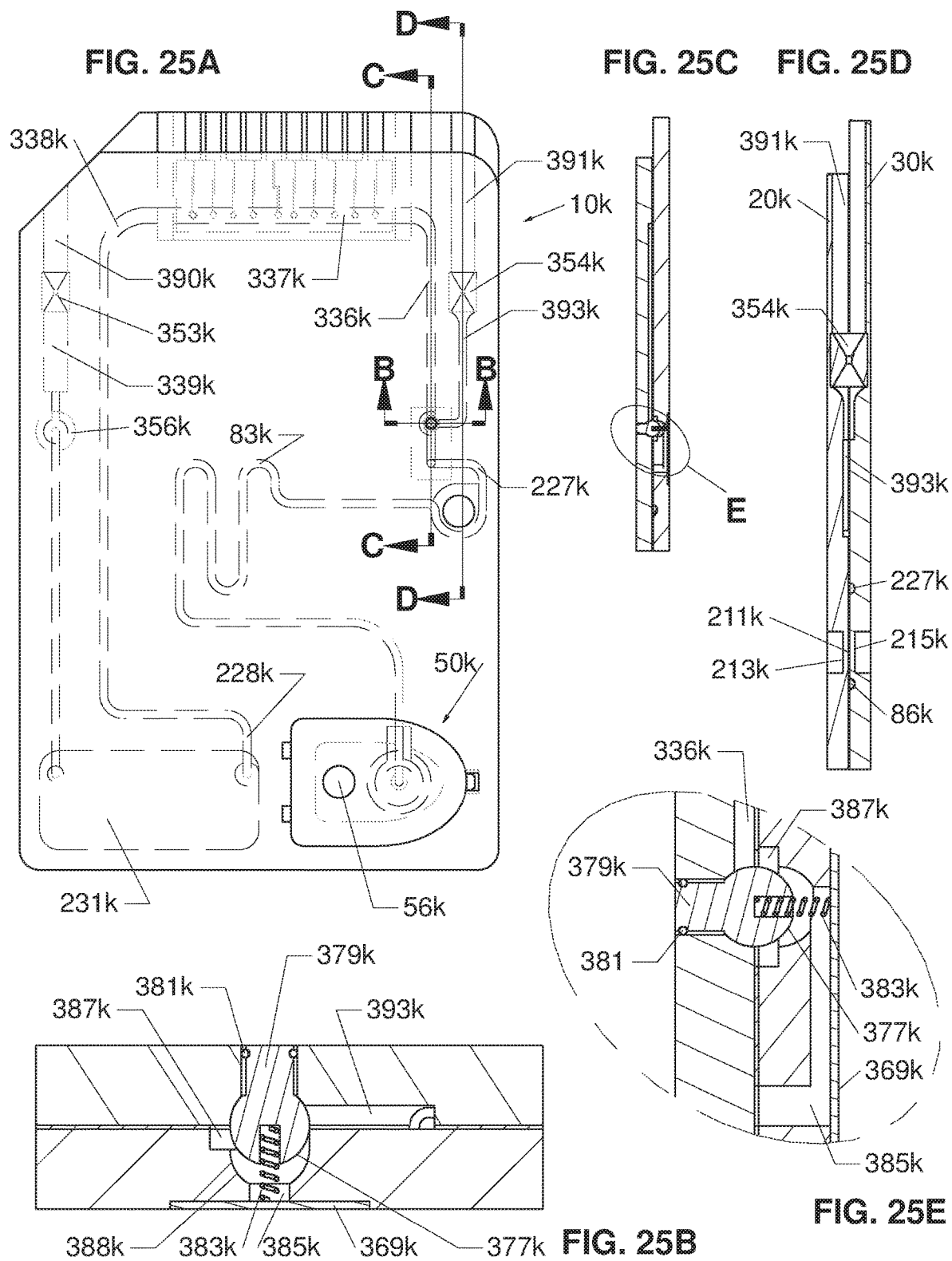

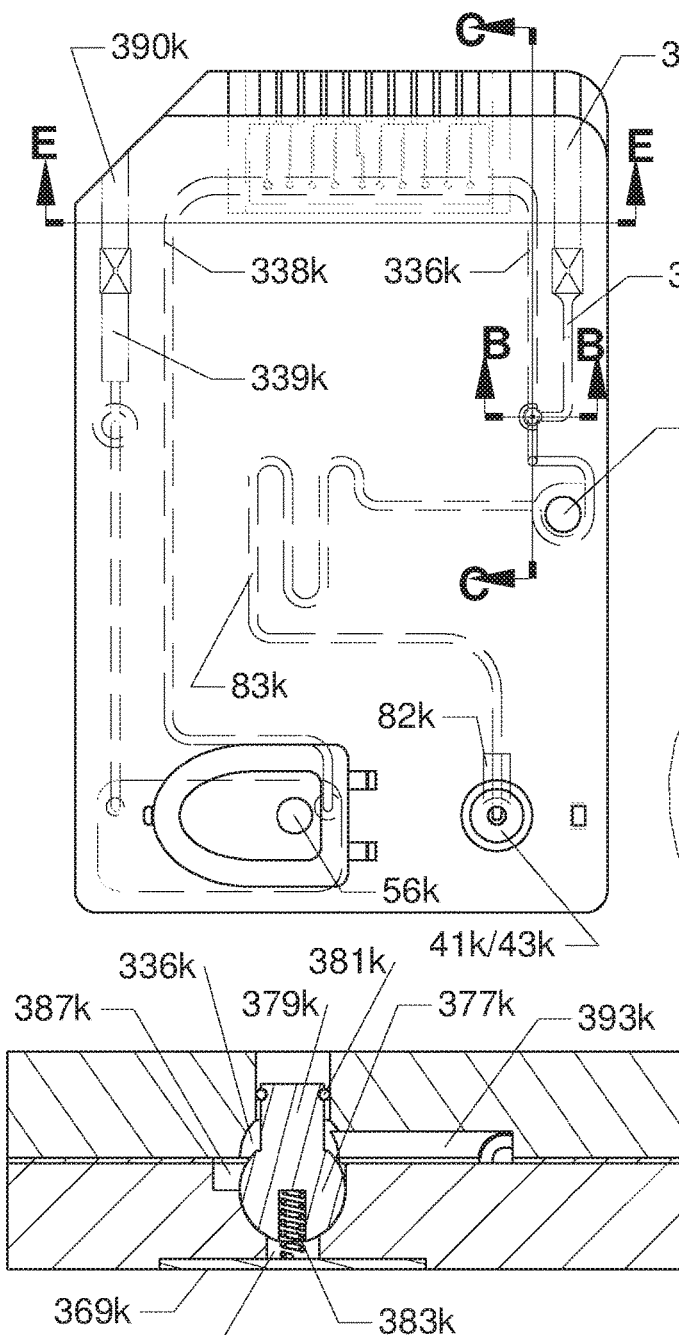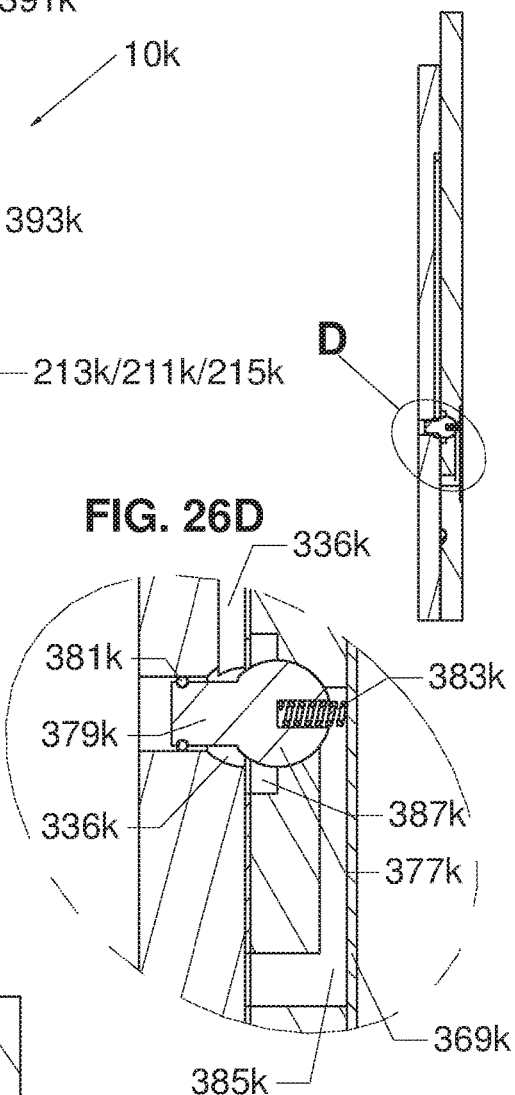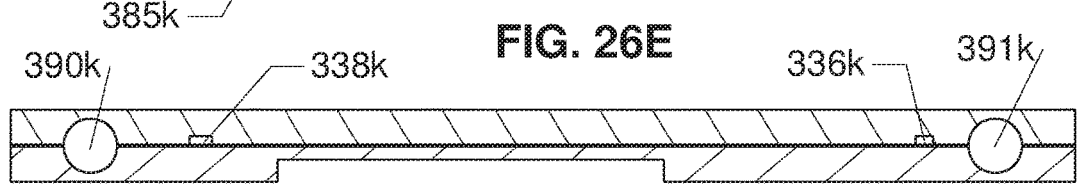

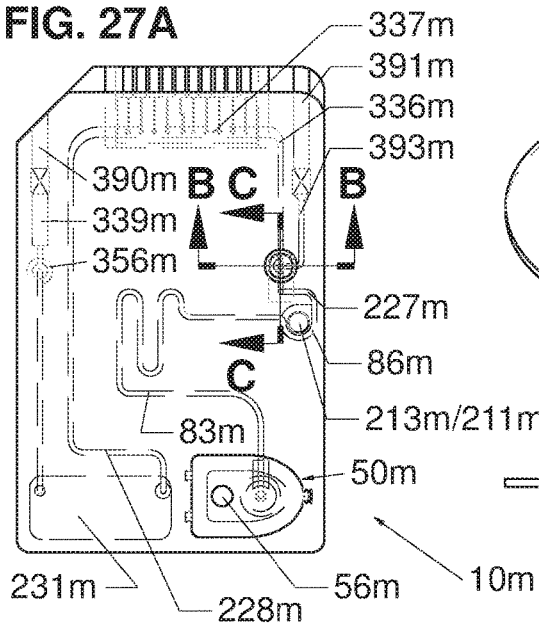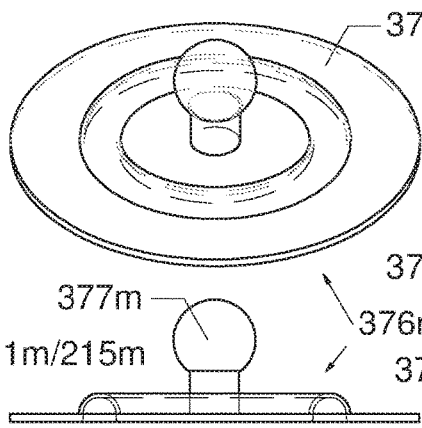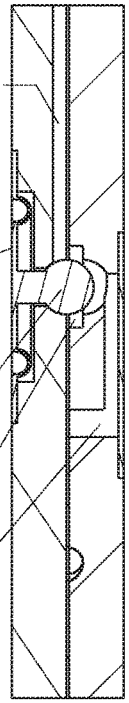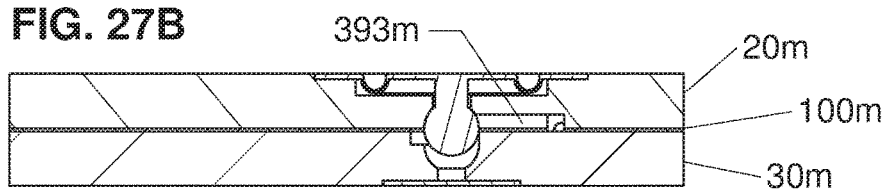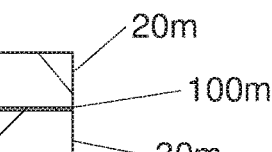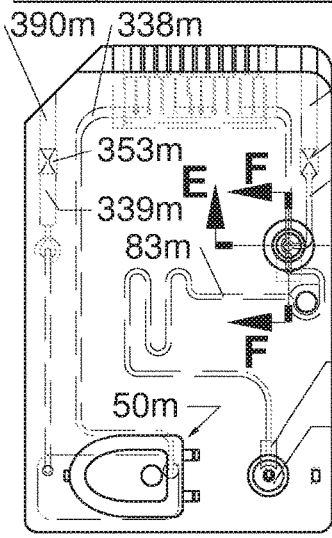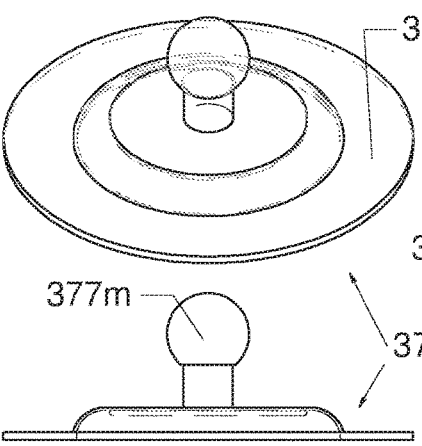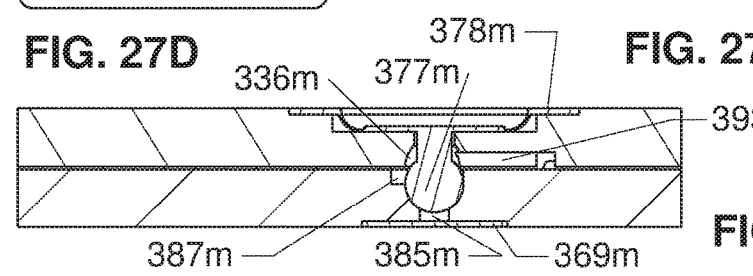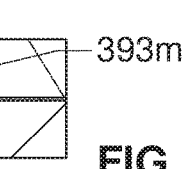

DISPOSABLE CARTRIDGE SYSTEM FOR POINT-OF-CARE TESTING

CROSS-REFERENCE TO RELATED APPLICATIONS

This application is a continuation-in-part of U.S. application Ser. No. 15/995,895, filed Jun. 1, 2018, now U.S. Pat. No. 10,272,430; which is a continuation-in-part of U.S. application Ser. No. 15/680,736, filed Aug. 18, 2017, now U.S. Pat. No. 9,999,884; which is a continuation of International Application No. PCT/CA2017/050584, filed May 16, 2017; and is a continuation-in-part of U.S. application Ser. No. 15/356,630, filed Nov. 20, 2016, now U.S. Pat. No. 9,821,307; which claims the benefit of U.S. Provisional Application No. 62/258,520, filed Nov. 22, 2015; the entire contents of each of which are incorporated herein by reference.

FIELD OF THE INVENTION

The invention relates to a disposable cartridge used for measuring a property of a blood sample. The disposable cartridge is useful for point-of-care testing (POCT).

BACKGROUND OF THE INVENTION

The result of reaction between a liquid sample and one or more reagent, preferably dry, depends on the quantity of the one or more reagent and the volume of liquid sample. Although any type of liquid sample is implied, serum, plasma and blood (also referred to as whole blood) are samples of particular interest. When blood is allowed to clot and the sample is centrifuged, the yellow liquid that sits on top of the blood clot is called serum. If the blood is collected in a tube containing an anticoagulant, for example heparin, and the sample is centrifuged, the yellow liquid that sits on top of the packed red blood cells is called plasma. The ratio of the packed red cell volume to the total volume of whole blood is referred to as the hematocrit. Since only the RBCs contain hemoglobin, total hemoglobin concentration is highly correlated with hematocrit, except in cases of for example, macrocytic anemia where the mean red cell hemoglobin concentration is lower than that of a normal red cell. Some analyzers measure hematocrit by electrical conductivity and convert the hematocrit measurement to a total hemoglobin concentration, and some analyzers measure total hemoglobin concentration by spectroscopy, and convert the total hemoglobin concentration to a hematocrit value. Spectroscopic calibration algorithms can be developed to measure both hematocrit and total hemoglobin concentration.

Point-of-care Testing (POCT) is defined as medical diagnostic testing performed outside the clinical laboratory in close proximity to where the patient is receiving care. POCT is typically performed by non-laboratory personnel and the results are used for clinical decision making. For the sake of convenience and rapid turnaround time, blood is the sample of choice. Due to the complexity of blood, certain tests can only be performed on serum or plasma.

POCT has a range of complexity and procedures that vary from manual procedures to automated procedures conducted by portable analyzers. POCT is most efficient when the sample of interest can be applied to or loaded onto a test cartridge, the sample inlet capped, and the remaining steps are performed automatically after the loaded and capped test cartridge is inserted into a slot or receptor of an analyzer.

Some blood tests, for example coagulation assays and immunoassays require a fixed volume of sample, for example, to ensure that when mixed with a reagent the ratio of the volume of sample to the volume of the reagent is held constant. Other tests, for example that determine electrolytes, do not require a fixed volume of sample. In the case of electrolytes, sample volume may not be an issue if the electrolyte concentration is estimated by measuring electrical activity in the sample, but other issues regarding sample volume must be considered. Electrolytes are examples of tests that are usually measured using electrochemical sensors, also referred to as biosensors. There are other tests that do not require a fixed volume of sample, and cannot be measured using biosensors, for example CO-oximetry and bilirubin. CO-oximetry is a spectroscopic or optical technique that is used to measure the amount different Hemoglobin (Hb) species present in a blood sample, for example, Oxy-Hb, Deoxy-Hb, Met-Hb, Carboxy-Hb and Total-Hb.

Electrolytes and CO-oximetry measurements do not usually require fixed volumes of blood, but a process is required to regulate the distance the blood is allowed to travel along microfluidic channels inside the cartridge. This distance is controlled by regulating the volume of blood dispensed from the sample storage well. The term metered blood means blood supplied in a measured or regulated amount.

Applying an unmetered sample volume to test strips is well known; some test strips contain absorbing sections that can accommodate a known volume of plasma, after the red cells are retained in another section of the test strip near the blood application site. In some cases, the hematocrit affects the plasma flow in test strips, and therefore correction for hematocrit may improve accuracy of the analyte measurement. In some test cartridges, a pipette that is designed to aspirate a predetermined sample volume, is used to apply a fixed volume of sample to the test cartridge.

U.S. Pat. No. 6,750,053 to Opalsky et al and U.S. Pat. No. 7,682,833 to Miller et al disclose devices for rapidly metering samples. U.S. Pat. No. 6,750,053 describes a snap-shut seal and states (column 11 lines 16-19) that the "volume of the metered fluid sample is the volume of the holding chamber 20 between the orifice (48 in FIG. 5) in the wall of the holding chamber and the capillary stop 22." U.S. Pat. No. 7,682,833 discloses (column 23 lines 39-43) that the "location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed." In the cases of U.S. Pat. Nos. 6,750,053 and 7,682,833, while the fluid sample is metered, the sample in the sample collection well (illustrated in U.S. Pat. No. 6,750,053 as element 12 in FIG. 3) is wasted.

Sample size is a major consideration for POCT systems, especially when it is desirable to use a small drop of blood obtained by puncturing the skin of a body part; the sample is referred to as a pin-prick sample. With some patients, it is difficult to obtain a small drop of blood, therefore there is a need to avoid any blood wastage. This is particularly true for neonatal blood testing.

Prothrombin Time (PT) is an example of a coagulation test, which requires a fixed sample volume. PT is usually reported as PT-INR (PT-International Normalized Ratio). The result for a prothrombin time performed on a normal individual will vary according to variations between different types and batches of thromboplastins used. The INR was devised to standardize the results using an ISI (International Sensitivity Index) value. Each manufacturer assigns an ISI value for any thromboplastin they manufacture. Another factor which affects PT-INR when using whole blood, as is the case of POCT, is the hematocrit. Only plasma contains coagulation factors, but a whole blood sample has a variable number of red cells mixed in, depending on the patient's hematocrit. These red cells take up space in the test cartridge. The coagulation factors that are being tested, are all in the liquid part of blood, i.e., the plasma. Because patients have different hematocrits, each patient sample adds a different amount of liquid plasma to the cartridge, but the amount of thromboplastin in the test cartridge is fixed. In a patient with low hematocrit, the excess plasma volume dilutes the reagent i.e., thromboplastin, and slows clot formation, resulting in a falsely increased PT-INR. PT-INR measured in the laboratory usually uses plasma, and plasma measurement of PT-INR is considered the gold standard. Therefore, whole blood PT-INR measurement will differ from the laboratory PT-INR measurement, which uses plasma. For POCT of PT-INR, correction can be made for an average hematocrit value, but errors in the PT-INR will increase as the hematocrit value moves away from the average hematocrit value. POCT of PT-INR usually use biosensors (also referred to as electrochemical detectors) that in many cases do not provide hematocrit measurement because the blood clots within seconds, after the blood is mixed with the thromboplastin.

U.S. Pat. No. 9,470,673 and CA Pat. No. 2,978,737 to Samsoondar, teach disposable cartridges for operation with a joint spectroscopic and biosensor blood analyzer. These publications teach a male-configured cartridge inlet, with the dual purposes of engaging a female-configured cap for sealing the inlet, and engaging a capillary adaptor for drawing blood into the cartridge by capillary action. The described combination of cap, capillary adaptor and inlet provides for dispensing blood from a syringe into the cartridge, as well as drawing capillary blood from a pin prick drop of blood on a patient's skin into the cartridge, for testing. U.S. Pat. No. 9,470,673 and CA Pat. No. 2,978,737 do not teach how the inlet can engage a cap that is hingedly attached to the cartridge, to provide a sealed configuration having a closed air passage for connecting an air bladder to the blood storage conduit, in order to push blood from the sample well into the optical chamber, or into both the optical chamber and the biosensor chamber, using pressurized air from the air bladder. These documents also do not teach how the capillary adaptor as described, can be used if a cap is hingedly attached to the body of the cartridge, and they do not teach a sample storage well for storing most of the blood sample.

U.S. Pat. No. 7,108,833 to Samsoondar teaches a sample tab comprising a sample well having an inlet for receiving a blood sample, and a hinged cap for engaging with the inlet, wherein when the cap is engaged with the inlet after the sample is deposited in the sample well, the capped sample well becomes an optical chamber. U.S. Pat. No. 7,108,833 does not teach a blood flow channel.

U.S. Pat. No. 5,096,669 to Lauks teaches a disposable cartridge having a housing, a sample inlet, a hinged snap-on cap for sealing the inlet after drawing the sample into the cartridge by capillary action, and an air bladder. U.S. Pat. No. 5,096,669 does not teach an optical chamber.

Neither of the aforementioned publications teaches or suggests the use of negative pressure to regulate blood flow. U.S. Pat. No. 9,901,928 to Lin et al teaches the use of negative pressure to draw blood into a disposable cartridge, but U.S. Pat. No. 9,901,928 does not teach or suggest an optical chamber.

A disposable cartridge for measuring a property of a sample is useful for POCT, and a disposable cartridge having a cap hingedly attached to a cartridge is safe, easy to operate with an analyzer, and the operation can be automated.

SUMMARY OF THE INVENTION

The invention relates to a disposable cartridge used for measuring a property of a sample. The disposable cartridge is useful for point-of-care testing (POCT).

Described herein is a system (A) for measuring one or more properties of a blood sample. The system (A) comprises:
i) a cartridge comprising:
  a cartridge body having an upper surface and a lower surface;
  a sample storage well for storing the blood sample, the sample storage well comprising a top portion for receiving the blood sample and a bottom portion for releasing at least a portion of the blood sample into a sample storage conduit, wherein the area of the top portion is substantially larger than the area of the bottom portion;
  an optical chamber for generating one or more signals during sample interrogation, the one or more signals used to calculate the one or more properties of the blood sample;
  the sample storage conduit for transferring the at least a portion of the blood from the sample storage well to the optical chamber;
  a cap hingedly attached to the cartridge body via a hinge, the cap having a top side and an underside;
ii) an analyzer, the analyzer comprising:
  a receptor for receiving the cartridge;
  a source of electromagnetic radiation for interrogating the blood in the optical chamber after the cartridge is inserted into the receptor;
  one or more detectors for receiving the one or more signals generated in the optical chamber; and
  one or more processors for controlling the analyzer and calculating the one or more properties of the blood sample from the one or more signals received by the one or more detectors; and wherein
iii) the system further comprising a positive pressure means for regulating blood flow in the cartridge, the positive pressure means comprising:
  an air bladder in the cartridge for generating pressurized air;
  an air bladder exit port located on the upper surface of the cartridge, the air bladder exit port operatively connected with the air bladder;
  an overflow conduit in communication with the optical chamber and a vent;
  a flat surface located on the upper surface of the cartridge body, the flat surface of the cartridge body surrounding the top portion of the sample storage well and the air bladder exit port; and
  a cap flat surface located on the underside of the cap; wherein
  the cartridge is adjustable between an unsealed configuration and a sealed configuration by rotating the cap about the hinge;
  in the unsealed configuration the sample storage well is configured to receive the blood sample; and
  in the sealed configuration a portion of the flat surface of the cartridge body mates with the cap flat surface to form a closed air passage operatively connecting the air bladder exit port to the sample storage well so that pressurized air from the air bladder exit port is transferable to the sample storage well, wherein the closed air passage is facilitated by a groove set into the upper surface of the cartridge body, a recess set into the underside of the cap, or a combination thereof, whereby when the air bladder is squeezed the portion of blood is urged from the sample storage well towards the optical chamber, and air within the overflow conduit is purged through the vent;

Additionally, in the system (A) as described above, the cartridge may comprise a biosensor chamber disposed between, and in operative communication with, the optical chamber and the vent. The biosensor chamber comprising one or more biosensors for generating one or more signals used to calculate an additional one or more properties of the blood sample. The cartridge may further comprise a calibration fluid pouch in operative communication with the biosensor chamber. The calibration fluid pouch containing calibration fluid for calibrating the one or more biosensors Also described herein is a system (B) for measuring one or more properties of a blood sample. The system (B) comprises:

i) a cartridge comprising:
a cartridge body having an upper surface and a lower surface;
a sample storage well for storing the blood sample, the sample storage well comprising a top portion for receiving the blood sample and a bottom portion for releasing at least a portion of the blood sample into a sample storage conduit, wherein the area of the top portion is substantially larger than the area of the bottom portion;
an optical chamber for generating one or more signals during sample interrogation, the one or more signals used to calculate the one or more properties of the blood sample;
the sample storage conduit for transferring the at least a portion of the blood from the sample storage well to the optical chamber;
a cap hingedly attached to the cartridge body via a hinge, the cap having a top side and an underside;

ii) an analyzer, the analyzer comprising:
a receptor for receiving the cartridge;
a source of electromagnetic radiation for interrogating the blood in the optical chamber after the cartridge is inserted into the receptor;
one or more detectors for receiving the one or more signals generated in the optical chamber; and
one or more processors for controlling the analyzer and calculating the one or more properties of the blood sample from the one or more signals received by the one or more detectors; and wherein iii) the system further comprising a negative pressure means for regulating blood flow in the cartridge, the negative pressure means comprising:
a vacuum pump in the analyzer for generating negative pressure;
a vacuum hollow needle comprising a first end operatively connected to the vacuum pump, a second end distal to the first end and operatively connected to the first end, the vacuum hollow needle further comprising an outer surface;
a cartridge exit duct disposed downstream of the optical chamber and operatively connected to the optical chamber, the cartridge exit duct comprising a vacuum sealing member for frictionally engaging the outer surface of the vacuum hollow needle so that the negative pressure is transferable to the cartridge exit duct; wherein the cartridge is adjustable between an open configuration and a closed configuration by rotating the cap about the hinge;
in the open configuration the sample storage well is configured to receive the blood sample; and
in the closed configuration, the sample storage well is covered with the cap, the cap further comprising a cap breathable plug for subjecting the blood sample in the sample storage well to atmospheric pressure, whereby the at least a portion of the blood flows from the sample storage well towards the optical chamber when the cartridge exit duct is under negative pressure.

Furthermore, the system (B) as described above the cartridge may comprise a biosensor chamber disposed between, and in operative communication with, the optical chamber and the cartridge exit duct. The biosensor chamber comprising one or more biosensors for generating one or more signals used to calculate an additional one or more properties of the blood sample, and a biosensor chamber exit.

In the system (B) as described above, the analyzer may also comprise an analyzer calibration fluid pouch comprising calibration fluid and a collapsible wall. The analyzer calibration fluid pouch for dispensing calibration fluid. The analyzer calibration fluid pouch may be operatively connected to an analyzer calibration fluid dispensing needle. The analyzer calibration fluid dispensing needle comprising a first end in operative communication with the analyzer calibration fluid pouch, a second end distal to the first end for dispensing the calibration fluid, and an outer surface. The analyzer may also comprise an actuator for operating a directional valve located in the cartridge. Furthermore, the cartridge may comprise a calibration duct comprising an internal segment and a calibration sealing member. The calibration sealing member for frictionally engaging the outer surface of the analyzer calibration fluid dispensing needle, so that the calibration fluid may be transferred from the analyzer calibration fluid pouch to the internal segment of the calibration duct. The cartridge therefore comprises a calibration fluid flow path beginning at the internal segment of the calibration duct and ending at a point between the biosensor chamber exit and the cartridge exit duct, a blood flow path beginning at the sample storage well and ending at a point between the biosensor chamber exit and the cartridge exit duct, and a junction where the calibration fluid flow path intersects with the blood flow path. The directional valve of the cartridge is disposed at the junction, and movable from a first position to a second position. In the first position the directional valve establishes an operative communication between the vacuum pump and a leading edge of the blood. In the second position, the directional valve establishes an operative communication between the vacuum pump and the analyzer calibration fluid pouch.

In either system (A) or (B) as described above, the top portion of the sample storage well may comprise a boss for increasing the storage capacity sample storage well. Furthermore, the cartridge further comprises one of an enlarged cavity disposed in the sample storage conduit, and a hydrophobic insert adjacent to and aligned with the sample storage conduit, and the sample storage well further comprising internal walls, the internal walls of the sample storage well characterized as being more wettable than a surface of the sample storage conduit. Furthermore, the sample storage well may be a separate structure inserted in the cartridge body as a sample storage well insert.

Also described herein is a cartridge (A). The cartridge (A) comprises a cartridge body having:
- an upper surface and a lower surface, and a sample inlet portion located on the upper surface,
- the sample inlet portion comprising a sample storage well for storing a blood sample, the sample storage well comprising a top portion for receiving the blood sample and a bottom portion for releasing at least a portion of the blood sample into a sample storage conduit, wherein the area of the top portion is substantially larger than the area of the bottom portion;
- an air bladder exit port;
- a flat surface of the cartridge body, the flat surface of the cartridge body surrounding the top portion of the sample storage well and the air bladder exit port;
- an optical chamber for generating one or more signals during sample interrogation, the one or more signals used to calculate one or more properties of the blood sample;
- the sample storage conduit for transferring the at least a portion of the blood from the sample storage well to the optical chamber;
- an air bladder for generating pressurized air, the air bladder operatively connected with the air bladder exit port;
- a vent for relieving pressure in the optical chamber;
- a cap hingedly connected to the cartridge body via a hinge, the cap having a top side and an underside, wherein at least a portion of the underside comprises a cap flat surface;
- wherein, the cartridge is adjustable between an unsealed (open) configuration and a sealed (closed) configuration by rotating the cap about the hinge. In the unsealed (open) configuration the sample storage well is configured to receive the blood sample. In the sealed (closed) configuration a portion of the flat surface of the cartridge body mates with a portion of the cap flat surface to form a closed air passage operatively connecting the air bladder exit port to the sample storage well so that when the air bladder is squeezed pressurized air from the air bladder exit port is transferable to the sample storage well. The closed air passage is facilitated by a groove set into the upper surface of the cartridge body, a recess set into the underside of the cap, or a combination thereof. So that when the air bladder is squeezed the portion of the blood is urged from the sample storage well towards the optical chamber.

The cartridge (A) as described above may further comprise a biosensor chamber, the biosensor chamber disposed between, and in operative communication with, the optical chamber, the vent, and a biosensor chamber exit. The biosensor chamber comprising one or more biosensors for generating one or more signals that may be used to calculate one or more properties of the blood sample. The cartridge also comprises a calibration fluid pouch in operative communication with the biosensor chamber. The calibration fluid pouch contains calibration fluid that may be used to calibrate the one or more biosensors. The cartridge defines a blood flow path beginning at the sample storage well and ending at a point between the biosensor chamber exit and the vent, a calibration fluid flow path beginning at the calibration fluid pouch and ending at a point between the biosensor chamber exit and the vent, and a junction where the blood flow path and the calibration fluid flow path intersect. The cartridge comprises a directional valve disposed at the junction. The directional valve movable from a first position to a second position, wherein in the first position the directional valve permits movement of the calibration fluid along the calibration fluid flow path, and in the second position, the directional valve permits movement of the at least a portion of the blood along the blood flow path.

Furthermore, described herein is a cartridge (B). Cartridge (B) comprises a cartridge body having:
- an upper surface and a lower surface;
- a sample storage well disposed at the upper surface for storing a blood sample. The sample storage well comprising a top portion for receiving the blood sample and a bottom portion for releasing at least a portion of the blood sample into a sample storage conduit. The area of the top portion is substantially larger than the area of the bottom portion;
- an optical chamber for generating one or more signals during sample interrogation, the one or more signals may be used to calculate one or more properties of the blood sample;
- the sample storage conduit for transferring the portion of the blood from the sample storage well to the optical chamber;
- a cartridge exit duct disposed downstream of, and operatively connected to, the optical chamber, the cartridge exit duct comprising a vacuum sealing member for frictionally engaging an outer surface of a vacuum hollow needle when the cartridge is connected to the vacuum hollow needle of an analyzer. The vacuum hollow needle for transferring negative pressure from a vacuum pump of an analyzer to the cartridge exit duct; and
- a cap hingedly connected to the cartridge body via a hinge, the cap having a top side and an underside; wherein
- the cartridge is adjustable between an open configuration and a closed configuration by rotating the cap about the hinge. In the open configuration the sample storage well is configured to receive the blood sample. In the closed configuration, the sample storage well is covered with the cap. The cap further comprising a cap vent for subjecting the blood sample in the sample storage well to atmospheric pressure. In cartridge (B), the portion of the blood flows from the sample storage well to the cartridge exit duct when the cartridge exit duct is under negative pressure.

The cartridge (B) as described above may further comprises a biosensor chamber. The biosensor chamber disposed downstream of, and operatively connected to, the optical chamber and a biosensor chamber exit. The biosensor chamber comprising one or more biosensors for generating one or more signals that may be used to calculate an additional one or more properties of the blood sample.

The cartridge (B) as described above may also comprise a calibration duct comprising an internal segment of the calibration duct and a calibration sealing member. The calibration sealing member for frictionally engaging an outer surface of an analyzer calibration fluid dispensing needle, when the cartridge is connected with the analyzer, so that calibration fluid is transferable from an analyzer calibration fluid pouch located in the analyzer, to the internal segment of the calibration duct. The cartridge defines a calibration fluid flow path beginning at the internal segment of the calibration duct and ending at a point between the biosensor chamber exit and the cartridge exit duct, a blood flow path beginning at the sample storage well and ending at a point between the biosensor chamber exit and the cartridge exit duct, and a junction where the calibration fluid path intersects with the blood flow path. The cartridge comprises a directional valve, movable from a first position to a second position, wherein in the first position the directional valve permits movement of the calibration fluid along the calibration fluid flow path, and in the second position, the directional valve permits movement of a portion of the blood along the blood flow path. By having the directional valve disposed at the junction, an operative communication may be established between the vacuum pump and a leading edge of the at least a portion of the blood, or between the vacuum pump and the analyzer calibration fluid pouch.

In the cartridge (A) or (B) as described above, the top portion of the sample storage well may comprise a boss for increasing storage capacity of the sample storage well. The cartridge (A) or (B) may further comprises one of an enlarged cavity disposed in the sample storage conduit, and a hydrophobic insert adjacent to and aligned with the sample storage conduit, and the sample storage well further comprising internal walls, the internal walls of the sample storage well characterized as being more wettable than a surface of the sample storage conduit. Furthermore, the sample storage well may be a separate structure inserted in the cartridge body as a sample storage well insert.

Furthermore, in the cartridge (A) or (B) as defined above, the sample storage conduit may comprise an enlarged cavity. Additionally, the sample storage conduit may comprise at least one reagent, and the sample storage conduit comprises a mixing chamber.

Also provided herein is a method for measuring blood coagulation of a blood sample. The method comprising:
  providing a system comprising a disposable cartridge, an analyzer, and one of a positive pressure means for regulating flow of at least a portion of the blood sample in the cartridge, and a negative pressure means for regulating flow of at least a portion of the blood sample in the cartridge;
  the cartridge comprising:
    a cartridge body having an upper surface and a lower surface;
    a sample storage well comprising a top portion for receiving the blood sample and a bottom portion for releasing at least a portion of the blood sample into a sample storage conduit, wherein the area of the top portion is substantially larger than the area of the bottom portion;
    an optical chamber for generating one or more signals during sample interrogation; and
    the sample storage conduit further comprising one or more than one reagent, the sample storage conduit fluidly connecting the sample storage well and the optical chamber;
  the analyzer comprising:
    a receptor for receiving the cartridge;
    a source of electromagnetic radiation (EMR) for interrogating contents of the optical chamber;
    a spectrometer comprising a grating for dispersing the EMR emerging from at least a portion of the blood sample in the optical chamber, into component wavelengths, to produce dispersed EMR;
    a one-dimensional multi-channel detector for receiving the dispersed EMR from the grating and producing the one or more that one signals; and
    one or more processors for controlling the analyzer and processing the one or more than one signals received by the spectrometer;
  receiving the blood sample in the sample storage well;
  establishing a flow of at least a portion of the blood sample within the sample storage conduit;
  mixing the one or more reagents with at least a portion of the blood sample to produce a mixture;
  filling the optical chamber with at least some of the mixture;
  interrogating the mixture in the optical chamber with the EMR in a temporal manner to produce a set of temporal optical measurements over a range of wavelengths and over a range of time;
  preparing a primary two-dimensional matrix of the set of temporal optical measurements;
  preparing a secondary two-dimensional matrix comprising a subset of optical measurements for a plurality of selected wavelengths obtained from the range of wavelengths, and a plurality of selected times obtained from the range of time;
  calculating correlation coefficients for subsequent pairs of optical measurements from the secondary two-dimensional matrix;
  using the calculated correlation coefficients for generating an order derivative of a temporal correlation coefficient curve; and
  applying predefined criteria to the order derivative of a temporal correlation coefficient curve identifying at which selected time a coagulation process begins and at which selected time the coagulation process ends to determine a specific blood coagulation time; and
  reporting the specific blood coagulation time.

In the method described above, the order derivative of the set of calculated temporal correlation coefficients may be selected from one of a zero, a first, and a second, order derivative.

Other aspects and features of the present invention will become apparent, to those having ordinary skill in the art, upon review of the following description of specific embodiments of the invention, which are provided as examples.

BRIEF DESCRIPTION OF THE DRAWINGS

A better understanding of the novel features and advantages of the present invention will be made by reading the detailed description of the preferred embodiments provided later, in conjunction with the accompanying drawings, in which:

FIG. 1A is an exploded top perspective view of disposable cartridge 10 for measuring a property of a sample, the cartridge having a rapid sample metering system, according to a first embodiment of the cartridge;

FIG. 1B is a bottom view of the first housing member 20 of the cartridge shown in FIG. 1A;

FIG. 1C is the bottom view of the first housing member 20 of the cartridge shown in FIG. 1B, overlaid by and in alignment with the gasket 100 shown in FIG. 1A;

FIG. 1D is a top view of the second housing member 30 of the cartridge shown in FIG. 1A;

FIG. 1E is the top view of the second housing member 30 shown in FIG. 1D, overlaid by and in alignment with the gasket 100 shown in FIG. 1A;

FIG. 1F is a top view of the cartridge 10 shown in FIG. 1A, with the cap 50 in a fully closed position;

FIG. 1G is a first enlarged cross-sectional view through the cartridge shown in FIG. 1F along line G-G;

FIG. 1H is a second enlarged cross-sectional view through the cartridge shown in FIG. 1F along line H-H;

FIG. 1J is a third enlarged cross-sectional view through the cartridge shown in FIG. 1F along line J-J;

FIG. 2B is a top view of the cartridge 10 shown collectively in FIGS. 1A-1J, with the cap 50 in a fully open position;

FIG. 2C is a top view of the cartridge 10 shown collectively in FIGS. 1A-1J, with the cap 50 in a partly open position;

FIG. 2D is a top view of the cartridge 10 shown collectively in FIGS. 1A-1J, with the cap 50 in a fully closed position FIG. 3A is a perspective view of the cartridge 10 shown in FIG. 2A, with air bladder 340 open;

FIG. 3B is a detailed view of detail B of the cartridge shown in FIG. 3A, showing details of the sample inlet portion 40;

FIG. 3C is a perspective top view of the cartridge 10 shown in FIG. 2D;

FIG. 3D is a detailed view of detail D of the cartridge shown in FIG. 3C;

FIG. 4A is a top view of the cap 50 shown in FIGS. 2B-2D;

FIG. 4B is a perspective top view of the cap 50 shown in FIG. 4A;

FIG. 4C is a front view of the cap 50 shown in FIG. 4A;

FIG. 4D is a right side view of the cap 50 shown in FIG. 4A;

FIG. 4E is a bottom view of the cap 50 shown in FIG. 4A;

FIG. 4F is a perspective bottom view of the cap 50 shown in FIG. 4E;

FIG. 4G is a cross-sectional view through the cap 50 shown in FIG. 4E along line G-G;

FIG. 5A is an exploded top perspective view of the disposable cartridge 10b for measuring a property of a sample, the cartridge having a rapid sample metering system, according to a second embodiment of the cartridge;

FIG. 5B is a bottom view of the first housing member 20b of the cartridge shown in FIG. 5A;

FIG. 5C is the bottom view of the first housing member 20b shown in FIG. 5B, overlaid by and in alignment with the gasket 100b shown in FIG. 5A;

FIG. 5D is a top view of the second housing member 30b of the cartridge shown in FIG. 5A;

FIG. 5E is the top view of the second housing member 30b shown in FIG. 5D, overlaid by and in alignment with the gasket 100b shown in FIG. 5A;

FIG. 6A is a top view of the cartridge 10b shown collectively in FIGS. 5A-5H, with the cap 50b removed FIG. 6B is a top view of the cartridge 10b shown collectively in FIGS. 5A-5H, with the cap 50b in a fully open position;

FIG. 6C is a top view of the cartridge 10b shown collectively in FIGS. 5A-5H, with the cap 50b in a partly open position;

FIG. 6D is a top view of the cartridge 10b shown collectively in FIGS. 5A-5H, with the cap 50b in a fully closed position;

FIG. 6E is a cross-sectional view of cartridge 10b shown in FIG. 6D along line E-E;

FIG. 6F is a detailed view of detail F of cartridge 10b shown in FIG. 6E, showing a snap-fit mechanism for attaching the pin 60b of cap 50b in the cartridge;

FIG. 7A is a perspective top view of the cartridge 10b with the cap 50b removed, shown in FIG. 6A;

FIG. 7B is a detailed view of detail B of the cartridge shown in FIG. 7A, showing details of the sample inlet portion 40b;

FIG. 7C is a perspective top view of the cartridge 10b shown in FIG. 6D;

FIG. 7D is a detailed view of detail D of the cartridge shown in FIG. 7C;

FIG. 8A is a top view of the cap 50b shown in FIG. 7C;

FIG. 8B is a perspective top view of the cap 50b shown in FIG. 8A;

FIG. 8C is a front view of the cap 50b shown in FIG. 8A;

FIG. 8D is a right side view of the cap 50b shown in FIG. 8A;

FIG. 8E is a bottom view of the cap 50b shown in FIG. 8A;

FIG. 8F is a perspective bottom view of the cap 50b shown in FIG. 8E;

FIG. 8G is a cross-sectional view through the cap 50b shown in FIG. 8E along line G-G;

FIG. 9A is an exploded top view of the disposable cartridge 10c for measuring a property of a sample, the cartridge having a rapid sample metering system, according to a third embodiment of the cartridge;

FIG. 9B is a bottom view of the first housing member 20c of the cartridge shown in FIG. 9A;

FIG. 9C is the bottom view of the first housing member 20c shown in FIG. 9B, overlaid by and in alignment with the gasket 100c shown in FIG. 9A;

FIG. 9D is a top view of the second housing member 30c of the cartridge shown in FIG. 9A;

FIG. 9E is the top view of the second housing member 30c shown in FIG. 9D, overlaid by and in alignment with the gasket 100c shown in FIG. 9A;

FIG. 11A is a top view of the cartridge 10c (similar to the view shown in FIG. 9F) with the cap 50c in a fully closed position, for illustrating the internal structure;

FIG. 11B is a first enlarged cross-sectional view through the cartridge 10c shown in FIG. 11A along line B-B;

FIG. 11C is a second enlarged cross-sectional view through the cartridge 10c shown in FIG. 11A along line C-C;

FIG. 11D is a third enlarged cross-sectional view through the cartridge 10c shown in FIG. 11A along line D-D;

FIG. 11E is a fourth enlarged cross-sectional view through the cartridge 10c shown in FIG. 11A along line E-E;

FIG. 14A is an exploded top view of the disposable cartridge 10e in an open configuration, for measuring a property of a sample, according to a fifth embodiment of the cartridge;

FIG. 14B is a bottom view of the first housing member 20e of the cartridge shown in FIG. 14A;

FIG. 14C is the bottom view of the first housing member 20e of the cartridge shown in FIG. 14B, overlaid by and in alignment with the gasket 100e shown in FIG. 14A;

FIG. 14D is a top view of the second housing member 30e of the cartridge shown in FIG. 14A;

FIG. 14E is the top view of the second housing member 30e shown in FIG. 14D, overlaid by and in alignment with the gasket 100e shown in FIG. 14A;

FIG. 15A is a perspective top view of the cartridge 10e in a closed configuration;

FIG. 15B is a perspective top view of the cartridge 10e in an open configuration;

FIG. 15C is a top view of the cartridge 10e in a closed configuration;

FIG. 15D is a first cross-sectional view through the cartridge 10e shown in FIG. 15C along line D-D;

FIG. 15E is a detailed view of detail E of the cartridge shown in FIG. 15D;

FIG. 15F is a second cross-sectional view through the cartridge 10e shown in FIG. 15C along line F-F;

FIG. 15G is a detailed view of detail G of the cartridge shown in FIG. 15F;

FIG. 16A is an exploded top view of the disposable cartridge 10f in an open configuration, for measuring a property of a sample, according to a sixth embodiment of the cartridge;

FIG. 16B is a bottom view of the first housing member 20f of the cartridge shown in FIG. 16A;

FIG. 16C is the bottom view of the first housing member 20f of the cartridge shown in FIG. 16B, overlaid by and in alignment with the gasket 100f shown in FIG. 16A;

FIG. 16D is a top view of the second housing member 30f of the cartridge shown in FIG. 16A;

FIG. 16E is the top view of the second housing member 30f shown in FIG. 16D, overlaid by and in alignment with the gasket 100f shown in FIG. 16A;

FIG. 17A is a perspective top view of the cartridge 10f in a closed configuration;

FIG. 17B is a perspective top view of the cartridge 10f in an open configuration;

FIG. 17C is a top view of the cartridge 10f in a closed configuration;

FIG. 17D is a first cross-sectional view through the cartridge 10f shown in FIG. 17C along line D-D;

FIG. 17E is a detailed view of detail E of the cartridge shown in FIG. 17D;

FIG. 17F is a second cross-sectional view through the cartridge 10f shown in FIG. 17C along line F-F;

FIG. 17G is a detailed view of detail G of the cartridge shown in FIG. 17F;

FIG. 19A is a perspective top view of the cartridge 10g in a closed configuration;

FIG. 19B is a perspective top view of the cartridge 10g in an open configuration;

FIG. 19C is a top view of the cartridge 10g in a closed configuration;

FIG. 19D is a first cross-sectional view through the cartridge 10g shown in FIG. 19C along line D-D;

FIG. 19E is a detailed view of detail E of the cartridge shown in FIG. 19D;

FIG. 19F is a second cross-sectional view through the cartridge 10g shown in FIG. 19C along line F-F;

FIG. 19G is a detailed view of detail G of the cartridge shown in FIG. 19F;

FIG. 20A is an exploded top view of the disposable cartridge 10h in a closed configuration, for measuring one or more properties of a sample, according to an eighth embodiment of the cartridge;

FIG. 20B is a bottom view of the first housing member 20h of the cartridge shown in FIG. 20A;

FIG. 20C is the bottom view of the first housing member 20h of the cartridge shown in FIG. 20B, overlaid by and in alignment with the gasket 100h shown in FIG. 20A;

Figure 2A:
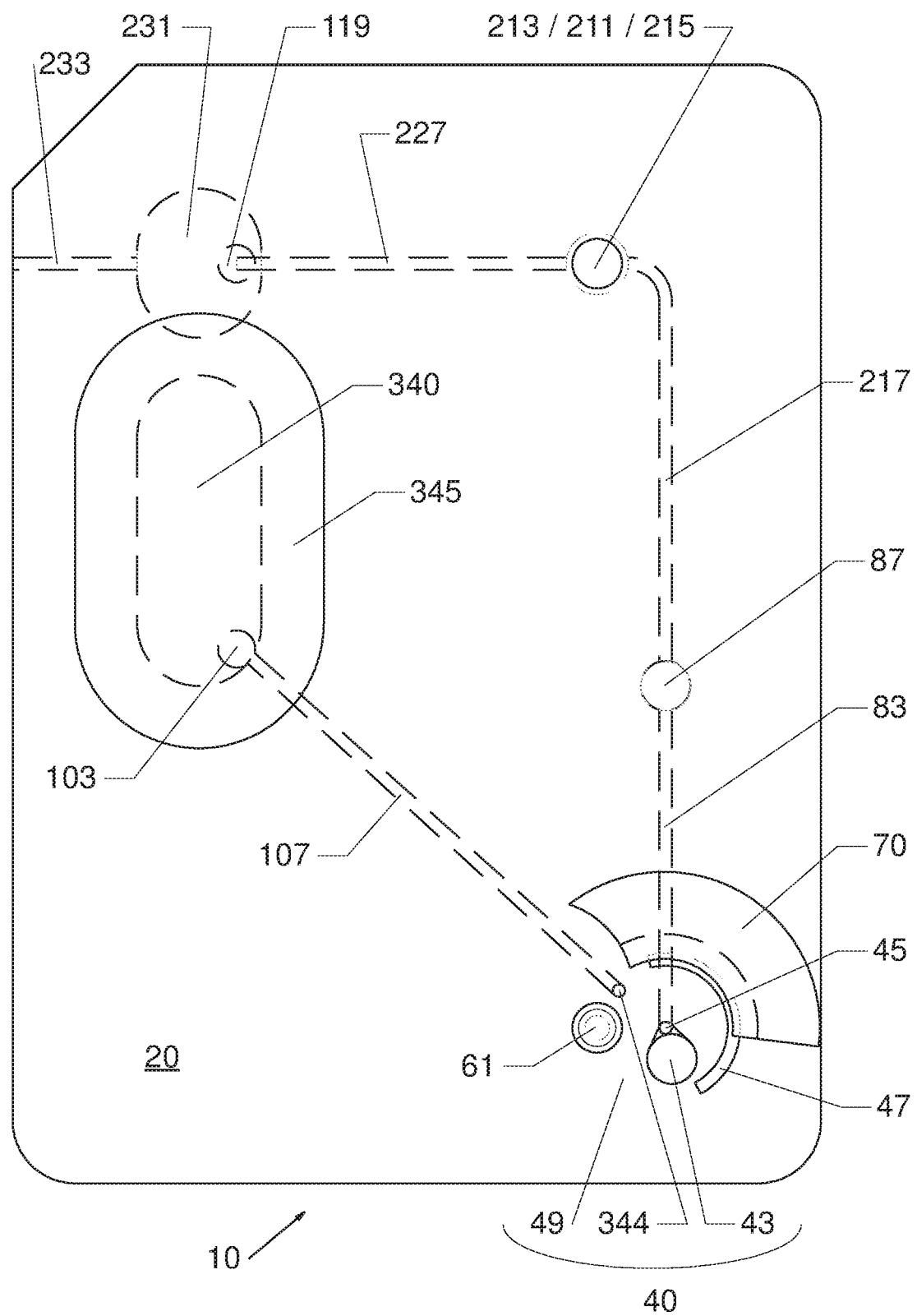
FIG. 2A is a top view of the cartridge 10 shown collectively in FIGS. 1A-1J, with the cap 50 and pin 60 removed.

FIG. 20D is a top view of the second housing member 30*h* of the cartridge shown in FIG. 20A, showing cavity 372 for anchoring elastomeric flap 371;

FIG. 20E is the top view of the second housing member 30*h* shown in FIG. 20D, overlaid by and in alignment with the gasket 100*h* shown in FIG. 20A, with the biosensor array 330 installed;

FIG. 20F is a detailed view of detail F of the cartridge shown in FIG. 20E, showing elastomeric flap 371 underneath gasket 100*h*;

FIG. 21A is a perspective view of the cartridge 10*h* in a closed configuration, showing the upper surface;

FIG. 21B is a perspective view of the cartridge 10*h*, showing the bottom or lower surface;

FIG. 21C is a perspective view of the cartridge 10*h* in an open configuration, showing the upper surface;

FIG. 21D is a top view of the cartridge 10*h* in a closed configuration, showing the upper surface;

FIG. 21E is a first enlarged cross-sectional view through the cartridge 10*h* shown in FIG. 21D along line E-E;

FIG. 21F is a second enlarged cross-sectional view through the cartridge 10*h* shown in FIG. 21D along line F-F;

FIG. 21G is a third enlarged cross-sectional view through the cartridge 10*h* shown in FIG. 21D along line G-G;

FIG. 21H is a fourth enlarged cross-sectional view through the cartridge 10*h* shown in FIG. 21D along line H-H;

FIG. 22A is an exploded top view of the disposable cartridge 10*j* in a closed configuration, for measuring one or more properties of a sample, according to a ninth embodiment of the cartridge;

FIG. 22B is a bottom view of the first housing member 20*j* of the cartridge shown in FIG. 22A, showing sample storage well insert 441*j* installed;

FIG. 22C is the bottom view of the first housing member 20*j* of the cartridge shown in FIG. 22B, overlaid by and in alignment with the gasket 100*j* shown in FIG. 22A;

FIG. 22D is a top view of the second housing member 30*j* of the cartridge shown in FIG. 22A;

FIG. 22E is the top view of the second housing member 30*j* shown in FIG. 22D, overlaid by and in alignment with the gasket 100*j* shown in FIG. 22A;

FIG. 23A is a perspective view of the cartridge 10*j* in a closed configuration, showing the upper surface;

FIG. 23B is a perspective view of the cartridge 10*j*, showing the bottom or lower surface;

FIG. 23C is a perspective view of the cartridge 10*j* in an open configuration, showing the upper surface;

FIG. 23D is a top or upper view of the cartridge 10*j* in a closed configuration;

FIG. 23E is a first enlarged cross-sectional view through the cartridge 10*j* shown in FIG. 23D along line E-E;

FIG. 23F is a second enlarged cross-sectional view through the cartridge 10*j* shown in FIG. 23D along line F-F;

FIG. 23G is a third enlarged cross-sectional view through the cartridge 10*j* shown in FIG. 23D along line G-G;

FIG. 24A is an exploded top view of the disposable cartridge 10*k* in an open configuration, for measuring one or more properties of a sample, according to a tenth embodiment of the cartridge;

FIG. 24B is a bottom view of the first housing member 20*k* of the cartridge shown in FIG. 24A;

FIG. 24C is a bottom view of the second housing member 30*k* of the cartridge shown in FIG. 24A;

FIG. 24D is a detailed view of the detail D of the second housing member 30*k* of the cartridge shown in FIG. 24A;

FIG. 25A is a top view of the cartridge 10*k* in a closed configuration;

FIG. 25B is a first (enlarged) cross-sectional view through the cartridge 10*k* shown in FIG. 25A along line B-B, showing the ball of a directional valve in an up position;

FIG. 25C is a second (not enlarged) cross-sectional view through the cartridge 10*k* shown in FIG. 25A along line C-C, showing the ball of the directional valve in an up position;

FIG. 25D is a third (enlarged) cross-sectional view through the cartridge 10*k* shown in FIG. 25A along line D-D;

FIG. 25E is a detailed view of detail E of the cartridge shown in FIG. 25C;

FIG. 26A is a top view of the cartridge 10*k* in an open configuration;

FIG. 26B is a first (enlarged) cross-sectional view through the cartridge 10*k* shown in FIG. 26A along line B-B, showing the ball of the directional valve in a down position;

FIG. 26C is a second (not enlarged) cross-sectional view through the cartridge 10*k* shown in FIG. 26A along line C-C, showing the ball of the directional valve in a down position;

FIG. 26D is a detailed view of detail D of the cartridge shown in FIG. 26C;

FIG. 26E is a third (enlarged) cross-sectional view through the cartridge 10*k* shown in FIG. 26A along line E-E, showing cartridge exit duct 390*k* and calibration duct 391*k* for allowing needles of an analyzer to enter the cartridge;

FIG. 27A is a top view of the cartridge 10*m* in a closed configuration, for measuring one or more properties of a sample, according to an eleventh embodiment of the cartridge, with the ball of a directional valve in an up position;

FIG. 27B is a first enlarged cross-sectional view through the cartridge 10*m* shown in FIG. 27A along line B-B, showing the ball of the directional valve in the up (or retracted) position;

FIG. 27C is a second enlarged cross-sectional view through the cartridge 10*m* shown in FIG. 27A along line C-C, showing the ball of the directional valve in the up (or retracted) position;

FIG. 27D is a top view of the cartridge 10*m* in an open configuration, with the ball of the directional valve in the down position;

FIG. 27E is a first enlarged cross-sectional view through the cartridge 10*m* shown in FIG. 27D along line E-E, showing the ball of the directional valve in a down (or extended) position;

FIG. 27F is a second enlarged cross-sectional view through the cartridge 10*m* shown in FIG. 27D along line F-F, showing the ball of the directional valve in the down (or extended) position;

FIG. 27G is a perspective view of the valve element 376*m* of cartridge 10*m*, in an inverted position (for displaying the ball 377*m* in a retracted position), with the ball in a retracted position;

FIG. 27H is a front view of the valve element 376*m* shown in FIG. 27G (observe the ball 377*m* in a retracted position);

FIG. 27J is a perspective view of the valve element 376*m* of cartridge 10*m*, in an inverted position (for displaying the ball 377*m* in an extended position), with the ball in an extended position; and FIG. 27K is a front view of the valve element 376*m* shown in FIG. 27J (observe the ball 377*m* in an extended position).

For a better understanding of the present invention, and to show more clearly how it may be carried into effect, reference will now be made, by way of example, to the accompanying drawings, and which are described in the following detailed description of preferred aspects of the invention.

DETAILED DESCRIPTION OF PREFERRED ASPECTS OF THE INVENTION

A disposable cartridge for measuring one or more properties of a sample is described. The disposable cartridge is useful for point-of-care testing (POCT). The disposable cartridge provides for automatic sample volume metering so that after applying an unknown sample volume to the cartridge, a specific volume of the sample is used for measuring the property of the sample.

For example, and as described in detail below, the disposable cartridge may comprise a cartridge body having an upper surface and a lower surface, a cap hingedly (or pivotally) connected to the cartridge body by a pin or hinge so that the cap is positioned on the upper surface of the cartridge body. The cap comprises a top side and an underside. The underside may comprise a cap recess surrounded by a flat surface (also referred to as a cap flat surface). The disposable cartridge further comprises a sample inlet portion located on the upper surface of the cartridge body. The sample inlet portion including:

a sample storage well comprising a top surface that defines a top opening (also termed a top portion) for receiving the sample and a bottom portion (a bottom opening defined by the cartridge body) for releasing at least some of the sample into a sample storage conduit;

an air bladder exit port;

and a flat surface (also referred to as a body flat surface) surrounding the sample storage well and the air bladder exit port, the body flat surface for engaging the flat surface of the underside of the cap. Regarding the fifth, sixth, seventh, eighth, ninth, tenth and eleventh embodiments of a cartridge, and depending on the wettability of the sample storage well, the wettability of the sample storage conduit, the use of a hydrophobic insert, and the strategic location of an enlarged cavity in the sample storage conduit, most of the sample may be stored in the sample storage well. Therefore, it should be understood that in some embodiments the sample storage conduit may function mostly as a conduit for transferring sample from the sample storage well to a detection chamber, whereas in other embodiments, for example the first embodiment, the sample storage conduit may store a substantial portion of the sample, before the sample is forced into the detection chamber. Either positive pressure may be applied to the surface of the sample in the storage well, or negative pressure may be applied to the leading edge of the sample, in order to establish a sample flow path. When some of the embodiments of the cartridge are properly inserted into the receptor of the analyzer, the optical chamber of the cartridge is usually inside the analyzer thereby shielding the optical chamber from room light, and the sample storage well is usually outside the analyzer with the closed cap projecting upwards out of the cartridge body. Therefore, the sample storage conduit may function as the conduit for operatively connecting the optical chamber and the sample storage well.

In embodiments one to four and seven described below, the cap includes a sweeping edge that may be used to skim off any excess of the sample when received by the sample storage well, the sample inlet portion or both, when the cap is pivotally rotated from an open position where the cartridge is in an unsealed configuration, to a closed positioned where the cartridge is in a sealed configuration. The sample storage conduit is in operative communication with the bottom opening of the sample storage well and an enlarged cavity, and is used to receive a portion of the sample. The total volume of the sample in the cartridge, when in the sealed configuration, is equivalent to the volume measured from the top opening of the sample storage well to the capillary break. The cartridge body further comprises a detection chamber in operative communication with the enlarged cavity (may also be referred to as capillary break based on its function) and the sample storage conduit (via a detection chamber inlet conduit). The detection chamber is for receiving a portion of the total volume of the sample from the sample storage conduit and for generating one or more signals during sample interrogation, the signals used to calculate one or more properties of the sample. The cartridge body may also comprise a vent in fluid communication with the detection chamber, the vent for relieving pressure in the detection chamber, and an air bladder in fluid or operative communication with the air bladder exit port. When the disposable cartridge is in the unsealed configuration, the sample storage well is open and available to receive the sample. When in the sealed configuration and the cap is in a closed position, the cap recess facilitates provision of a closed air passage connecting the air bladder exit port and the sample storage well for communicating pressurized air from the air bladder to the sample storage well via the air bladder exit port, so that when the air bladder is pressed or squeezed, the volume of the sample, or a portion thereof, is urged from the sample storage conduit into the detection chamber.

In embodiments five and six (see FIGS. 14A to 17H), and eight to eleven (see FIGS. 20A to 27K) as described below, the cap is hingedly attached so that the cap rotates vertically with reference to a plane substantially orthogonal to the plane defined by the body flat surface surrounding the sample storage well and the air bladder exit port of the cartridge, as opposed to the horizontal motion with reference with reference to a plane defined by the body flat surface surrounding the sample storage well and the air bladder exit port, as described with reference to embodiments one to four and seven (see FIGS. 1 to 13, 18 and 19). In cartridges that do not comprise an air bladder exit port, the cap rotation plane may be described as a vertical plane with reference to a plane substantially orthogonal to a plane defined by a surface surrounding the hinge.

In embodiments five, six and eight an air bladder is used to regulate the volume of the blood released from the sample storage well. In embodiments one to four and seven, the air bladder is used to regulate the distance from the vent that the front end or leading edge of the blood is allowed to flow.

Also described herein is a method for measuring a property of a blood sample. The method comprises depositing a blood sample into the sample storage well of the disposable cartridge as defined herein, the disposable cartridge in the unsealed configuration. In some cartridges, the cartridge cap is rotated horizontally or along a plane generally defined by the flat surface surrounding the sample storage well and the air bladder exit port of the cartridge, about a pin. Excess blood is skimmed off and the disposable cartridge is adjusted from an unsealed configuration to a sealed configuration, producing a sealed cartridge containing a known volume of the sample. In other cartridges, the cartridge cap rotates vertically with reference to a plane orthogonal to a plane generally defined by the flat surface surrounding the sample storage well and the air bladder exit port of the cartridge. In cartridges comprising a vertically rotating cap, the surface of the blood sample deposited in the sample storage well is not skimmed off, and the volume of the deposited sample used is regulated by controlling the extent to which the air bladder is squeezed. The sealed cartridge is inserted into a receptor of an analyzer, the analyzer comprising the receptor for receiving the disposable cartridge, one or more processors for controlling the analyzer; means for activating the air bladder; and one or more detectors for receiving the one or more signals from one or more detection chambers and sending the one or more signals to the one or more processors for transforming the one or more signals into one or more properties of the sample. After the closed cartridge is inserted into the analyzer receptor, the air bladder is activated and provides the pressurized air so that at least some of the sample moves through one of the detection chamber inlet conduits. The cartridge may contain at least one reagent, and a reagent chamber, containing the at least one reagent. If the cartridge contains at least one reagent, then the at least one reagent is dissolved in the blood to produce a mixture of the blood and the at least one reagent. The blood, or the mixture of blood and the at least one reagent, is urged into the detection chamber and the property of the blood sample is measured in the detection chamber using the analyzer.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−25% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The terms "operatively connected", "in operative communication", "in fluid communication" or "fluidly connected" and the like, describe elements of the disposable cartridge, for example, channels, ducts, conduits, tunnels, passageways, that permit either fluid flow, gas flow, or both fluid and gas flow between the various compartments or elements within the disposable cartridge that are connected by the channels, ducts, conduits, tunnels, passageways and the like.

Disposable Cartridges with a Rapid Sample Metering System

Detailed description of novel features of examples of the invention is discussed now, and is best understood with reference to the accompanying drawings. These examples are to be considered non-limiting, and a person of ordinary skill in the art will understand that variations are within the scope of the invention, even though they are not explicitly illustrated. The same reference numerals are used for similar elements in different examples; in some cases, letters are appended to the end of the reference numerals to denote the embodiment of the invention illustrated. For example, the letters "b" (FIGS. 5-8), "c" (FIGS. 9-11), "d" (FIGS. 12-13), "e" (FIGS. 14-15), "f" (FIGS. 16-17), "g" (FIGS. 18-19), "h" (FIGS. 20-21), "j" (FIGS. 22-23), "k" (FIGS. 24-26) and "m" (FIG. 27) are used to refer to the $2^{nd}$, $3^{rd}$, $4^{th}$, $5^{Th}$, $6^{th}$, $7^{th}$, $8^{th}$, $9^{th}$, $10^{th}$ and, $11^{th}$ embodiments or examples of the invention, respectively. It should be noted that absence of a letter after a reference numeral does not imply that the element belongs to the first example of the invention. For easy reference, Table 1 provides a list of the reference numerals used, and a brief description of the corresponding structural features.

TABLE 1

Description of Structural Features.

| Reference Numerals | Description of Structural Features |
|---|---|
| 10 | A first embodiment of a cartridge |
| 10b | A second embodiment of a cartridge |
| 10c | A third embodiment of a cartridge |
| 10d | A fourth embodiment of a cartridge |
| 10e | A fifth embodiment of a cartridge |
| 10f | A sixth embodiment of a cartridge |
| 10g | A seventh embodiment of a cartridge |
| 10h | An eight embodiment of a cartridge |
| 10j | A ninth embodiment of a cartridge |
| 10k | A tenth embodiment of a cartridge |
| 10m | An eleventh embodiment of a cartridge |
| 20 | First housing member of cartridge 10 |
| 20b | First housing member of cartridge 10b |
| 20c | First housing member of cartridge 10c |
| 20d | First housing member of cartridge 10d |
| 20e | First housing member of cartridge 10e |
| 20f | First housing member of cartridge 10f |
| 20g | First housing member of cartridge 10g |
| 20h | First housing member of cartridge 10h |
| 20j | First housing member of cartridge 10j |

TABLE 1-continued

Description of Structural Features.

| Reference Numerals | Description of Structural Features |
|---|---|
| 20k | First housing member of cartridge 10k |
| 20m | First housing member of cartridge 10m |
| 30 | Second housing member of cartridge 10 |
| 30b | Second housing member of cartridge 10b |
| 30c | Second housing member of cartridge 10c |
| 30d | Second housing member of cartridge 10d |
| 30e | Second housing member of cartridge 10e |
| 30f | Second housing member of cartridge 10f |
| 30g | Second housing member of cartridge 10g |
| 30h | Second housing member of cartridge 10h |
| 30j | Second housing member of cartridge 10j |
| 30k | Second housing member of cartridge 10k |
| 30m | Second housing member of cartridge 10m |
| 40 | A sample inlet portion of cartridge 10, which comprises some elements of the cartridge that interact with the cap 50 |
| 40b | A sample inlet portion of cartridge 10b, which comprises some elements of the cartridge that interact with the cap 50b |
| 40c | A sample inlet portion of cartridge 10c, which comprises some elements of the cartridge that interact with the cap 50c |
| 40d | A sample inlet portion of cartridge 10d, which comprises some elements of the cartridge that interact with the cap 50d |
| 40e | A sample inlet portion of cartridge 10e, which comprises some elements of the cartridge that interact with the cap 50e |
| 40f | A sample inlet portion of cartridge 10f which comprises some elements of the cartridge that interact with the cap 50f |
| 40g | A sample inlet portion of cartridge 10g, which comprises some elements of the cartridge that interact with the cap 50g |
| 40h | A sample inlet portion of cartridge 10h, which comprises some elements of the cartridge that interact with the cap 50h |
| 41 | A sample storage well of an inlet portion 40 of cartridge 10 |
| 41b | A sample storage well of cartridge 10b |
| 41d | A sample storage well of cartridge 10d |
| 41e | A sample storage well of cartridge 10e |
| 41f | A sample storage well of cartridge 10f |
| 41g | A sample storage well of cartridge 10g |
| 41h | A sample storage well of cartridge 10h |
| 41j | A sample storage well of cartridge 10j |
| 41k | A sample storage well of cartridge 10k |
| 41m | A sample storage well of cartridge 10m |
| 43 | Top opening (or top portion) of a sample storage well 41 of cartridge 10 |
| 43b | Top opening (or top portion) of a sample storage well 41b of cartridge 10b |
| 43c | Top opening (or top portion) of a sample storage well of cartridge 10c |
| 43d | Top opening (or top portion) of a sample storage well 41d of cartridge 10d |
| 43e | Top opening (or top portion) of a sample storage well 41e of cartridge 10e |
| 43f | Top opening (or top portion) of a sample storage well 41f of cartridge 10f |
| 43g | Top opening (or top portion) of a sample storage well 41g of cartridge 10g |
| 43h | Top opening (or top portion) of a sample storage well 41h of cartridge 10h |
| 43j | Top opening (or top portion) of a sample storage well 41j of cartridge 10j |
| 43k | Top opening (or top portion) of a sample storage well 41k of cartridge 10k |
| 43m | Top opening (or top portion) of a sample storage well 41m of cartridge 10m |
| 44h | Sample storage well boss of cartridge 10h |
| 44j | Sample storage well boss of cartridge 10j |
| 44k | Sample storage well boss of cartridge 10k |
| 44m | Sample storage well boss of cartridge 10m |
| 45 | Bottom opening (or bottom portion) of sample storage well 41 of cartridge 10 |
| 45b | Bottom opening (or bottom portion) of sample storage well 41b of cartridge 10b |
| 45d | Bottom opening (or bottom portion) of sample storage well 41d of cartridge 10d |
| 45c | Bottom opening (or bottom portion) of sample storage well of cartridge 10c |
| 45d | Bottom opening (or bottom portion) of sample storage well of cartridge 10d |
| 45e | Bottom opening (or bottom portion) of sample storage well 41e of cartridge 10e |
| 45f | Bottom opening (or bottom portion) of sample storage well 41l of cartridge 10f |
| 45g | Bottom opening (or bottom portion) of sample storage well 41g of cartridge 10g |
| 45h | Bottom opening (or bottom portion) of sample storage well 41h of cartridge 10h |
| 45j | Bottom opening (or bottom portion) of sample storage well 41j of cartridge 10j |
| 46 | Enlarge cavity near the bottom opening 45e of sample storage well 41e of cartridge 10e, for providing means for minimizing blood flow out of the sample storage well 41e, except when the air bladder 340e is squeezed |
| 46h | Enlarged cavity comprising a top portion 46h'' and a bottom portion 46h'' (see FIG. 21D and E) |

TABLE 1-continued

Description of Structural Features.

| Reference Numerals | Description of Structural Features |
|---|---|
| 47 | A sample overflow well of an inlet portion 40 of cartridge 10 |
| 47b | A sample overflow well of an inlet portion 40b of cartridge 10b |
| 47g | A sample overflow well of an inlet portion 40g of cartridge 10g |
| 48c | Groove disposed at the underside and at the sweeping portion of the cap 50c of cartridge 10c, for storing excess sample |
| 48d | Groove disposed at the underside and at the sweeping portion of the cap 50d, for storing excess sample |
| 49 | A sliding surface of inlet portion 40 of cartridge 10, surrounding sample storage well 41 |
| 49b | A sliding surface of inlet portion 40b of cartridge 10b, surrounding sample storage well 41b |
| 49c | A sliding surface of inlet portion 40c of cartridge 10c, surrounding sample storage well 41c |
| 49d | A sliding surface of inlet portion 40d of cartridge 10d, surrounding sample storage well 41d |
| 49e | A flat surface of inlet portion 40e surrounding top opening 43e of a sample storage well 41e and the air bladder exit port 344e of cartridge 10e |
| 49f | A flat surface of inlet portion 40f surrounding the sample storage well and the air bladder exit port of cartridge 10f |
| 49g | A flat surface of inlet portion 40g surrounding the sample storage well and the air bladder exit port of cartridge 10g |
| 49h | A flat surface of inlet portion 40h surrounding the sample storage well and the air bladder exit port of cartridge 10h |
| 50 | A cap for closing inlet portion 40 of cartridge 10 |
| 50b | A cap for closing inlet portion 40b of cartridge 10b |
| 50c | A cap for closing inlet portion 40c of cartridge 10c |
| 50d | A cap for closing inlet portion 40d of cartridge 10d |
| 50e | A cap for closing inlet portion 40e of cartridge 10e |
| 50f | A cap for closing inlet portion 40f of cartridge 10f |
| 50g | A cap for closing inlet portion 40g of cartridge 10g |
| 50h | A cap for closing inlet portion 40h of cartridge 10h |
| 50j | A cap for closing inlet portion 40j of cartridge 10j |
| 50k | A cap for closing inlet portion 40k of cartridge 10k |
| 50m | A cap for closing inlet portion 40m of cartridge 10m |
| 51 | Top side of cap 50 of cartridge 10 |
| 51b | Top side of cap 50b of cartridge 10b |
| 51e | Top side of cap 50e of cartridge 10e |
| 51f | Top side of cap 50f of cartridge 10f |
| 51g | Top side of cap 50g of cartridge 10g |
| 52 | Underside of cap 50 of cartridge 10 |
| 52b | Underside of cap 50b of cartridge 10b |
| 52e | Underside of cap 50e of cartridge 10e |
| 52f | Underside of cap 50f of cartridge 10f |
| 53 | A sweeping portion of cap 50 of cartridge 10 |
| 53b | A sweeping portion of cap 50b of cartridge 10b |
| 53c | A sweeping portion of cap 50c of cartridge 10c |
| 54 | A trailing portion of cap 50 of cartridge 10 |
| 54b | A trailing portion of cap 50b of cartridge 10b |
| 54c | A trailing portion of cap 50c of cartridge 10c |
| 55 | Cap recess in the underside of cap 50 of cartridge 10 |
| 55b | Cap recess in the underside of cap 50b of cartridge 10b |
| 55c | Cap recess in the underside of cap 50c of cartridge 10c |
| 55d | Cap recess in the underside of cap 50d of cartridge 10d |
| 55e | Channel in body of cartridge 10e for facilitating formation of a closed passage for connecting the air bladder exit port 344e to the sample storage well 41e |
| 55f | Cap recess in the underside 52f of cap 50f of cartridge 10f for facilitating formation of a closed passage for connecting the air bladder exit port 344f to the sample storage well 41f |
| 55g | Cap recess in the underside of cap 50g of cartridge 10g for facilitating formation of a closed passage for connecting the air bladder exit port 344g to the sample storage well 41g |
| 55h | Cap recess in the underside of cap 50h of cartridge 10h for facilitating formation of a closed passage for connecting the air bladder exit port 344h to the sample storage well 41h |
| 55j | Cap recess in the underside of cap 50j of cartridge 10j |
| 55k | Cap recess in the underside of cap 50k of cartridge 10k |
| 55m | Cap recess in the underside of cap 50m of cartridge 10m |
| 56j | Cap breathable plug of cartridge 10j, which functions as a cap vent |
| 56k | Cap breathable plug of cartridge 10k, which functions as a cap vent |
| 56m | Cap breathable plug of cartridge 10m, which functions as a cap vent |
| 57 | A cap sealing ring/washer (referred to as a gasket or seal in some embodiments) in cap 50 of cartridge 10 |
| 57c | A cap sealing gasket in cap 50c of cartridge 10c |
| 57d | A cap sealing gasket in cap 50d of cartridge 10d |
| 57e | A cap sealing gasket in the body of cartridge 10e |

TABLE 1-continued

Description of Structural Features.

| Reference Numerals | Description of Structural Features |
|---|---|
| 57f | A cap sealing gasket in cap 50f of cartridge 10f |
| 57g | A cap sealing gasket in cap 50g of cartridge 10g |
| 57h | A cap sealing gasket in cap 50h of cartridge 10h |
| 58 | A sweeping cap edge disposed at the sweeping portion 53 of cap 50 for skimming off excess sample |
| 58b | A sweeping cap edge disposed at the sweeping portion 53b of cap 50b for skimming off excess sample |
| 58c | A sweeping cap edge disposed at the sweeping portion 53c of cap 50c for skimming off excess sample |
| 58d | A sweeping cap edge disposed at the sweeping portion of cap 50d for skimming off excess sample |
| 59 | A cap handle for facilitating rotation of cap 50 |
| 60 | A pin or hinge for hingedly (or pivotally) attaching the cap 50 to the sample inlet portion 40 and allowing the cap to swing with the cap sealing ring/washer 57 frictionally engaged with the surface 49 (see FIG. 2A) of inlet portion 40. Note: The term pivot is used to describe the pin or shaft 62c used with latch 70c. The attachment mechanism illustrated in FIG. 6F is optionally the same for the two hinged attachments. |
| 60b | A pin in cap 50b for hingedly attaching the cap to the sample inlet portion 40b and allowing the cap to swing with the non-recessed portion of the underside of the cap frictionally engaged with the surface 49b of inlet portion 40b |
| 60c | A pin in cap 50c for hingedly attaching the cap to the sample inlet portion 40c and allowing the cap to swing with the gasket 57c frictionally engaged with the surface 49c of inlet portion 40c |
| 60d | A pin in cap 50d for hingedly attaching the cap to the sample inlet portion 40d and allowing the cap to swing with the gasket 57d frictionally engaged with the surface 49d of inlet portion 40d |
| 60e' and 60e" | Hinges for hingedly attaching cap 50e to the body of cartridge 10e |
| 60f' and 60f" | Hinges for hingedly attaching cap 50f to the body of cartridge 10f |
| 60g | Pin for hingedly attaching cap 50g to body of cartridge 10g |
| 60h' and 60h" | Hinges for hingedly attaching cap 50h to the body of cartridge 10h |
| 60j' and 60j" | Hinges for hingedly attaching cap 50j to the body of cartridge 10j |
| 61 | A pin hole in first housing member for receiving pin 60 |
| 61b | A pin hole for receiving pin 60b |
| 61c | A pin hole for receiving pin 60c |
| 61e' and 61e" | Holes for anchoring hinges 60e' and 60e" for hingedly attaching cap 50e to body of cartridge 10e |
| 61f' and 61f" | Holes for anchoring hinges 60f' and 60f" for hingedly attaching cap 50f to body of cartridge 10f |
| 61g | A pin hole for receiving pin 60g for hingedly attaching cap 50g to body of cartridge 10g |
| 62c | Pivot of latch 70c |
| 63 | Bottom of pin hole 61 |
| 63b | Bottom of pin hole 61b |
| 63c | Bottom of pin hole 61c |
| 64c | Hole for receiving pivot 62c of latch 70c of cartridge 10c |
| 65b | Snap fit lip in pin 60b for locking pin 60b in pinhole 61b |
| 66c | Bottom of pivot hole 64c |
| 67b | Snap fit lip in pinhole 61b for locking pin 60b in pinhole 61b |
| 70 | Cap latch near inlet portion 40 |
| 70b | Cap latch near inlet portion 40b |
| 70c | Cap latch near inlet portion 40c |
| 70g | Cap latch near inlet portion 40g |
| 71 | Pin hole in cap 50 for receiving pin 60 |
| 72 | Cap stop for keeping cartridge 10d in either an unsealed configuration or a sealed configuration |
| 73 | Cap latch recess in cap latch 70 of cartridge 10 |
| 73b | Cap latch recess in cap latch 70b of cartridge 10b |
| 73g | Cap latch recess in cap latch 70g of cartridge 10g, for engaging cap 50g |
| 74e | Cap 50e latch catch for engaging cap latch 75e |
| 74f | Cap 50f latch catch for engaging cap latch 75f |
| 74h | Cap 50h latch catch for engaging cap latch 75h |
| 75e | Cap 50e latch |
| 75f | Cap 50f latch |
| 75h | Cap 50h latch |
| 75j | Cap 50j latch |
| 81 | A sample storage conduit entrance of a cartridge 10 |
| 81b | A sample storage conduit entrance of a cartridge 10b |
| 81c | A sample storage conduit entrance of a cartridge 10c |

TABLE 1-continued

Description of Structural Features.

| Reference Numerals | Description of Structural Features |
|---|---|
| 82 | Hydrophobic insert disposed at the entrance of sample storage conduit 83f for providing means for minimizing blood flow out of the sample storage well, except when the air bladder is squeezed |
| 82h | Hydrophobic insert disposed at the entrance of sample storage conduit 83h for providing means for regulating blood flow out of the sample storage well |
| 82k | Hydrophobic insert disposed at the entrance of sample storage conduit 83k for providing means for regulating blood flow out of the sample storage well |
| 82m | Hydrophobic insert disposed at the entrance of sample storage conduit 83m for providing means for regulating blood flow out of the sample storage well |
| 83 | A sample storage conduit of a cartridge 10 (see FIG. 1G) |
| 83b | A sample storage conduit of a cartridge 10b (see FIG. 5G) |
| 83c | A sample storage conduit of a cartridge 10c (see FIG. 11B) |
| 83d | A sample storage conduit of a cartridge 10c (see FIG. 12D) |
| 83e | A sample storage conduit of a cartridge 10e |
| 83f | A sample storage conduit of a cartridge 10f |
| 83g | A sample storage conduit of a cartridge 10g |
| 83h | A sample storage conduit of a cartridge 10h |
| 83j | A sample storage conduit of a cartridge 10j |
| 83k | A sample storage conduit of a cartridge 10k |
| 83m | A sample storage conduit of a cartridge 10m |
| 84c | Junction of sample storage conduit 83c and capillary break 87c of cartridge 10c (see FIG. 11B) |
| 85 | A sample storage conduit groove of a cartridge 10 |
| 85b | A sample storage conduit groove of a cartridge 10b |
| 85c | A sample storage conduit groove of a cartridge 10c (see FIG. 9H) |
| 86e | Blood shunt for bypassing optical chamber 211e, and providing fluid connection between sample storage well 41e and biosensor conduit 337e |
| 86f | Blood shunt for bypassing optical chamber 211f, and providing fluid connection between sample storage well 41f and biosensor conduit 337f |
| 86g | Blood shunt for bypassing optical chamber 211g, and providing fluid connection between sample storage well 41g and biosensor conduit 337g |
| 86h | Blood shunt for bypassing optical chamber 211h, and providing fluid connection between sample storage well 41h and biosensor conduit 337h |
| 86j | Blood shunt for bypassing optical chamber 211j, and providing fluid connection between sample storage well 41j and biosensor conduit 337j |
| 86k | Blood shunt for bypassing optical chamber 211k, and providing fluid connection between sample storage well 41k and biosensor conduit 337k |
| 86m | Blood shunt for bypassing optical chamber 211m, and providing fluid connection between sample storage well 41m and biosensor conduit 337m |
| 87' | Portion of a capillary break or enlarged cavity in a first housing member of cartridge 10 |
| 87" | Portion of a capillary break or enlarged cavity in a second housing member of cartridge 10 |
| 87 | A capillary break of a cartridge, comprising portions 87', 87", and a gasket cut-out 115 aligned with portions 87' and 87" |
| 87b' | Portion of a capillary break in a first housing member of cartridge 10b |
| 87b" | Portion of a capillary break in a second housing member of cartridge 10b |
| 87b | A capillary break of a cartridge, comprising portions 87b', 87b", and a gasket cut-out 115b aligned with portions 87b' and 87b" |
| 87c | A capillary break of cartridge 10c (see FIG. 11E) |
| 87c' | Portion of a capillary break 87c in a first housing member 20c of cartridge 10c |
| 87c" | Portion of a capillary break 87c in a second housing member 30c of cartridge 10c |
| 88 | A mixing chamber entrance groove of cartridge 10b (see FIG. 5B) |
| 89 | A mixing chamber of a cartridge 10b (see FIG. 5G) |
| 89c | A mixing chamber of a cartridge 10c |
| 89c' | Portion of mixing chamber 89c in a first housing member 20c of cartridge 10c |
| 89c" | Portion of mixing chamber 89c in a second housing member 30c of cartridge 10c |
| 91b | A post capillary break conduit for providing fluid communication between the capillary break 87b and the mixing chamber 89 (see FIG. 5G) |
| 91c | A post capillary break conduit for providing fluid communication between the capillary break 87c and the reagent chamber 209c (see FIG. 11B) |
| 92c | Junction of capillary break 87c and post capillary break conduit 91c (see FIG. 11E) |
| 100 | Double-sided sticky gasket of cartridge 10 |
| 100b | Double-sided sticky gasket of cartridge 10b |
| 100c | Double-sided sticky gasket of cartridge 10c |
| 100e | Double-sided sticky gasket of cartridge 10e |
| 100f | Double-sided sticky gasket of cartridge 10f |
| 100g | Double-sided sticky gasket of cartridge 10g |
| 100h | Double-sided sticky gasket of cartridge 10h |
| 100j | Double-sided sticky gasket of cartridge 10j |
| 100k | Double-sided sticky gasket of cartridge 10k |
| 100m | Double-sided sticky gasket of cartridge 10m |

TABLE 1-continued

Description of Structural Features.

| Reference Numerals | Description of Structural Features |
|---|---|
| 101 | Gasket cut-out 101 positioned to provide fluid connection between the bottom of a sample storage well and a sample storage conduit entrance 81 of cartridge 10 |
| 101b | Gasket cut-out 101b positioned to provide fluid connection between a bottom of a sample storage well and a sample storage conduit entrance of cartridge 10b |
| 101c | Gasket cut-out 101c positioned to provide fluid connection between a bottom of a sample storage well and a sample storage conduit entrance of cartridge 10c |
| 103 | Gasket cut-out 103 positioned to provide fluid connection between an air bladder window and an air bladder cavity |
| 103b | Gasket cut-out 103b positioned to provide fluid connection between air bladder 340b and air bladder duct 343b |
| 105 | Gasket cut-out 105 positioned to provide fluid connection between an air bladder and an air bladder exit port 344 |
| 105b | Gasket cut-out 105 positioned to provide fluid connection between an air bladder duct 343b and an air bladder exit port 344b |
| 107 | Gasket cut-out 107 is an extension of cut out 103, positioned to provide fluid connection between air bladder 340 (see FIG. 3A) and air bladder exit port 344b |
| 109 | Gasket cut-out 109 position to align with pin hole 61 |
| 109b | Gasket cut-out 109b position to align with pin hole 61b |
| 109c | Gasket cut-out 109c position to align with pin hole 61c |
| 115 | Gasket cut-out 115 position to align with capillary break 87 |
| 115b | Gasket cut-out 115b position to align with capillary break 87b |
| 115c | Gasket cut-out 115c position to align with capillary break 87c of cartridge 10c |
| 117 | Gasket cut-out 117 positioned to provide fluid connection between an optical chamber inlet conduit 217 (see FIG. 1G) and an optical chamber overflow conduit 227, and positioned to align with optical windows 213 and 215; in cartridge 10, gasket cut-out 117 defines an optical chamber 211 (see FIG. 1H). |
| 117c | Gasket cut-out 117c positioned to provide fluid connection between an optical chamber inlet conduit 217c and an optical chamber overflow conduit 227c, and positioned to align with optical windows 213c and 215c |
| 117e | Gasket cut-out positioned to align at least partly with at least one of optical windows 213e and 215e |
| 117f | Gasket cut-out positioned to align at least partly with at least one of optical windows 213f and 215f |
| 117g | Gasket cut-out positioned to align at least partly with at least one of optical windows 213g and 215g |
| 117h | Gasket cut-out positioned to align at least partly with at least one of optical windows 213h and 215h |
| 119 | Gasket cut-out 119 positioned to provide fluid connection between the optical chamber overflow conduit 227 and a waste receptacle 231 of cartridge 10 (see FIG. 1H) |
| 119b | Gasket cut-out 119b positioned to provide fluid connection between the distal end of the biosensor conduit 337 and a waste receptacle cavity 231b of cartridge 10b |
| 121 | Gasket cut-out 121 positioned to align with a portion of the biosensor conduit groove 335 and the active area 323 of the biosensor array 330 of cartridge 10b |
| 121e | Gasket cut-out positioned to align with active area of the biosensor array 330 of cartridge 10e |
| 121f | Gasket cut-out positioned to align with active area of the biosensor array 330 of cartridge 10f |
| 121g | Gasket cut-out positioned to align with active area of the biosensor array 330 of cartridge 10g |
| 121h | Gasket cut-out positioned to align with active area of the biosensor array 330 of cartridge 10h |
| 123 | Gasket cut-out 123 positioned to align with a portion of the inlet of the mixing chamber 89 of cartridge 10b (see FIG. 5G) |
| 125 | Gasket cut-out 125 positioned to align with a portion of the outlet of the mixing chamber 89 of cartridge 10b (see FIG. 5G) |
| 127 | Gasket cut-out 127 positioned to align with the reagent chamber 209c of cartridge 10c (see FIG. 11B) |
| 129 | Gasket cut-out 129 positioned to align with the mixing chamber 89c of cartridge 10c (see FIG. 11B) |
| 133 | Gasket cut-out 133 position to align with latch pivot hole 64c of cartridge 10c |
| 207e | Optical chamber entrance in cartridge 10e |
| 207f | Optical chamber entrance in cartridge 10f |
| 207g | Optical chamber entrance in cartridge 10g |
| 209c | A reagent chamber of cartridge 10c (see FIG. 11B) |
| 210c | Conduit for fluidly connecting reagent chamber 209c and mixing chamber 89c (see FIG. 11B) |
| 211 | An optical chamber in cartridge 10 for receiving sample mixed with reagent, and positioned to align with at least a portion of an optical window (see FIG. 1H) |

TABLE 1-continued

Description of Structural Features.

| Reference Numerals | Description of Structural Features |
|---|---|
| 211c | An optical chamber in cartridge 10c for receiving sample mixed with reagent, and positioned to align with at least a portion of an optical window (see FIG. 11C) |
| 211e | An optical chamber in cartridge 10e |
| 211f | An optical chamber in cartridge 10f |
| 211g | An optical chamber in cartridge 10g |
| 211h | An optical chamber in cartridge 10h |
| 211j | An optical chamber in cartridge 10j |
| 211k | An optical chamber in cartridge 10k |
| 211m | An optical chamber in cartridge 10m |
| 212e | Optical chamber exit in cartridge 10e |
| 212f | Optical chamber exit in cartridge 10f |
| 212g | Optical chamber exit in cartridge 10g |
| 213 | A first optical window of cartridge 10 |
| 213c | A first optical window of cartridge 10c |
| 213e | A first optical window of cartridge 10e |
| 213f | A first optical window of cartridge 10f |
| 213g | A first optical window of cartridge 10g |
| 213h | A first optical window of cartridge 10h |
| 213j | A first optical window of cartridge 10j |
| 213k | A first optical window of cartridge 10k |
| 213m | A first optical window of cartridge 10m |
| 215 | A second optical window of cartridge 10 |
| 215c | A second optical window of cartridge 10c |
| 215e | A second optical window of cartridge 10e |
| 215f | A second optical window of cartridge 10f |
| 215g | A second optical window of cartridge 10g |
| 215h | A second optical window of cartridge 10h |
| 215j | A second optical window of cartridge 10j |
| 215k | A second optical window of cartridge 10k |
| 215m | A second optical window of cartridge 10m |
| 217 | Detection chamber Inlet conduit joining capillary break 87 to detection (optical) chamber 211 |
| 217b | Detection chamber Inlet conduit joining mixing chamber 89 to detection chamber (biosensor conduit 337) |
| 217c | Detection chamber Inlet conduit joining mixing chamber 89c and detection (optical) chamber 211c of cartridge 10c |
| 219 | Optical chamber inlet conduit groove of optical chamber inlet conduit 217 of cartridge 10 |
| 226c | Conduit groove of optical chamber overflow conduit of cartridge 10c |
| 227 | Optical chamber overflow conduit of cartridge 10 (see FIGS. 1H and 2A). |
| 227c | Optical chamber overflow conduit of cartridge 10c |
| 227e | Optical chamber overflow conduit of cartridge 10e |
| 227f | Optical chamber overflow conduit of cartridge 10f |
| 227g | Optical chamber overflow conduit of cartridge 10g |
| 227h | Optical chamber overflow conduit of cartridge 10h for receiving sample flowing out of the optical chamber (see FIG. 21H) |
| 227j | Optical chamber overflow conduit of cartridge 10j for receiving sample flowing out of the optical chamber (see FIG. 23D) |
| 227k | Optical chamber overflow conduit of cartridge 10k for receiving sample flowing out of the optical chamber (see FIGS. 25A and 25D) |
| 227m | Optical chamber overflow conduit of cartridge 10m for receiving sample flowing out of the optical chamber (see FIG. 27A) |
| 228h | Detection chamber overflow conduit of cartridge 10h. In this example (see FIG. 21D), conduit 228h is an extension of detection chamber exit 338h and may also function as a waste receptacle for receiving excess fluid. The conduit may comprise more than one loops to increase the excess fluid storage capacity. |
| 228j | Detection chamber overflow conduit of cartridge 10j. In this example (see FIG. 23D), conduit 228j is an extension of detection chamber exit 338j and may also function as a waste receptacle for receiving excess fluid. The conduit may comprise more than one loops to increase the excess fluid storage capacity. In this example the cartridge also comprises a separate waste receptacle 231j for further increasing the excess fluid storage capacity. |
| 228k | Detection chamber overflow conduit of cartridge 10k |
| 228m | Detection chamber overflow conduit of cartridge 10m |
| 229 | Overflow conduit groove of optical chamber 211 of cartridge 10 |
| 231 | A waste receptacle of cartridge 10 for receiving excess fluid |
| 231b | A waste receptacle of cartridge 10b for receiving excess fluid |
| 231e | A waste receptacle of cartridge 10e for receiving excess fluid |
| 231f | A waste receptacle of cartridge 10f for receiving excess fluid |
| 231g | A waste receptacle of cartridge 10g for receiving excess fluid |
| 231j | A waste receptacle of cartridge 10j for receiving excess fluid |
| 231k | A waste receptacle of cartridge 10k for receiving excess fluid |
| 231m | A waste receptacle of cartridge 10m for receiving excess fluid |

TABLE 1-continued

Description of Structural Features.

| Reference Numerals | Description of Structural Features |
|---|---|
| 233 | A vent of cartridge 10 |
| 233b | A vent of cartridge 10b |
| 233c | A vent of cartridge 10c |
| 233e | A vent of cartridge 10e |
| 233f | A vent of cartridge 10f |
| 233g | A vent of cartridge 10g |
| 233h | A vent of cartridge 10h |
| 237c | Crown of cap knob of cap 50c of cartridge 10c |
| 239c | Neck of cap knob of cap 50c of cartridge 10c |
| 241c | Notch in cap 50c for mating with pivot 62c of latch 70c, when cartridge 10c is in a sealed configuration |
| 321 | Biosensor substrate for printing elements of the biosensors and for facilitating thermal contact with an analyzer heating element (see FIG. 5A) |
| 323 | Active area of a biosensor array 330 of cartridge 10b |
| 325 | Biosensor electrical contact of biosensors (see FIG. 5E) |
| 327 | A biosensor receptacle for arranging one or more biosensors in a cartridge in the form of a cut-out ledge in the second housing member 30b, and for exposing the underside of the biosensor(s) to facilitate heating (see FIG. 5A) |
| 330 | A biosensor array of cartridges 10b, 10e, 10f, 10g, 10h, 10j and 10k comprising one or more biosensors |
| 333 | Proximal end of a biosensor conduit groove of cartridge 10b |
| 335 | Distal end of a biosensor conduit groove of cartridge 10b |
| 336e | Biosensor chamber entrance, defining a location close to the proximal end of the biosensor chamber but outside the biosensor chamber of cartridge 10e |
| 336f | Biosensor chamber entrance, defining a location close to the proximal end of the biosensor chamber but outside the biosensor chamber of cartridge 10f |
| 336g | Biosensor chamber entrance, defining a location close to the proximal end of the biosensor chamber but outside the biosensor chamber of cartridge 10g |
| 336h | Biosensor chamber entrance, defining a location between the proximal end of the biosensor chamber and the directional valve of cartridge 10h |
| 336j | Biosensor chamber entrance, defining a location between the proximal end of the biosensor chamber and the optical chamber overflow conduit 227j of cartridge 10j |
| 336k | Biosensor chamber entrance, defining a location between the proximal end of the biosensor chamber and the directional valve of cartridge 10k |
| 336m | Biosensor chamber entrance, defining a location between the proximal end of the biosensor chamber and the directional valve of cartridge 10m |
| 337 | A biosensor conduit of cartridge 10b (see FIG. 5G) |
| 337e | A biosensor conduit or chamber of cartridge 10e |
| 337f | A biosensor conduit or chamber of cartridge 10f |
| 337g | A biosensor conduit or chamber of cartridge 10g |
| 337h | A biosensor conduit or chamber of cartridge 10h |
| 337j | A biosensor conduit or chamber of cartridge 10j |
| 337k | A biosensor conduit or chamber of cartridge 10k |
| 337m | A biosensor conduit or chamber of cartridge 10m |
| 338e | Biosensor chamber exit, defining a location close to the distal end of the biosensor chamber but outside the biosensor chamber of cartridge 10e |
| 338f | Biosensor chamber exit, defining a location close to the distal end of the biosensor chamber but outside the biosensor chamber of cartridge 10f |
| 338g | Biosensor chamber exit, defining a location close to the distal end of the biosensor chamber but outside the biosensor chamber of cartridge 10g |
| 338h | Biosensor chamber exit, defining a location close to the distal end of the biosensor chamber but outside the biosensor chamber of cartridge 10h |
| 338j | Biosensor chamber exit, defining a location close to the distal end of the biosensor chamber but outside the biosensor chamber of cartridge 10j |
| 338k | Biosensor chamber exit, defining a location close to the distal end of the biosensor chamber but outside the biosensor chamber of cartridge 10k |
| 338m | Biosensor chamber exit, defining a location close to the distal end of the biosensor chamber but outside the biosensor chamber of cartridge 10m |
| 339j | Cartridge exit, an inner portion of cartridge exit duct 390j of cartridge 10j, for establishing operative communication with a vacuum pump |
| 339k | Cartridge exit, a portion of cartridge exit duct 390k of cartridge 10k, for establishing operative communication with a vacuum pump |
| 339m | Cartridge exit, a portion of cartridge exit duct 390m of cartridge 10m, for establishing operative communication with a vacuum pump |
| 340 | An air bladder of cartridge 10 |
| 340b | An air bladder of cartridge 10b |
| 340e | An air bladder of cartridge 10e |
| 340f | An air bladder of cartridge 10f |
| 340g | An air bladder of cartridge 10g |
| 340h | An air bladder of cartridge 10h |
| 341 | An air bladder window of an air bladder 340 |
| 341b | An air bladder window of an air bladder 340b |
| 341c | An air bladder window of an air bladder 340c |
| 341e | An air bladder window of an air bladder 340e |

TABLE 1-continued

Description of Structural Features.

| Reference Numerals | Description of Structural Features |
|---|---|
| 341f | An air bladder window of an air bladder 340f |
| 341g | An air bladder window of an air bladder 340g |
| 341h | An air bladder window of an air bladder 340h |
| 342 | A groove in member 30b for defining air bladder duct 343b |
| 343b | An air bladder duct for providing fluid connection between an air bladder 340b and an air bladder exit port 344b |
| 343h | An air bladder duct for providing fluid connection between an air bladder 340h and an air bladder exit port 344h |
| 344 | An air bladder exit port of a sample inlet portion 40 of cartridge 10 |
| 344b | An air bladder exit port of a sample inlet portion 40b of cartridge 10b |
| 344c | An air bladder exit port of a sample inlet portion 40c of cartridge 10c |
| 344e | An air bladder exit port of a sample inlet portion 40e of cartridge 10e |
| 344f | An air bladder exit port of a sample inlet portion 40f of cartridge 10f |
| 344g | An air bladder exit port of a sample inlet portion 40g of cartridge 10g |
| 344h | Air bladder exit port of cartridge 10h |
| 345 | Flexible member of a cartridge for covering air bladder window 341 of cartridge 10 for facilitating operation of the air bladder 340 |
| 345b | Flexible member of a cartridge for covering air bladder window 341b of cartridge 10b for facilitating operation of the air bladder 340b |
| 345c | Flexible member of a cartridge for covering air bladder window 341c of cartridge 10c for facilitating operation of the air bladder 340c |
| 345e | Flexible member of air bladder 340e |
| 345f | Flexible member of air bladder 340f |
| 345g | Flexible member of air bladder 340g |
| 346c | Air bladder duct for providing fluid connection between an air bladder 340c and an air bladder exit port 344c (see FIG. 11E) |
| 346e | Air bladder duct for providing fluid connection between an air bladder 340e and an air bladder exit port 344e |
| 346f | Air bladder duct for providing fluid connection between an air bladder 340f and an air bladder exit port 344f |
| 346g | Air bladder duct for providing fluid connection between an air bladder 340g and an air bladder exit port 344g |
| 346h | Air bladder duct for providing fluid connection between an air bladder 340h and an air bladder exit port 344h |
| 347 | Recess for nesting flexible member 345, disposed at the surface of first housing member 20 of cartridge 10 |
| 347b | Recess for nesting flexible member 345b, disposed at the surface of first housing member 20b of cartridge 10b |
| 351c | Bottom cover for covering sample storage conduit 83c of cartridge 10c |
| 353j | Vacuum sealing member installed in cartridge exit duct 390j in cartridge 10j, for frictionally engaging the outer surface of a vacuum hollow needle. |
| 353k | Vacuum sealing member installed in cartridge exit duct 390k in cartridge 10k, for frictionally engaging the outer surface of a vacuum hollow needle. |
| 353m | Vacuum sealing member installed in cartridge exit duct 390m in cartridge 10m, for frictionally engaging the outer surface of a vacuum hollow needle. |
| 354k | Calibration sealing member in the calibration duct 391k in cartridge 10k, for frictionally engaging the outer surface of an analyzer calibration fluid dispensing needle. |
| 354m | Calibration sealing member in the calibration duct 391m in cartridge 10m, for frictionally engaging the outer surface of an analyzer calibration fluid dispensing needle. |
| 355h | Calibration fluid pouch for providing calibration fluid for calibrating one or more biosensors of cartridge 10h |
| 356j | Exit breathable plug |
| 356k | Exit breathable plug |
| 356m | Exit breathable plug |
| 357h | Compressible support for calibration fluid pouch 355h |
| 361h | Spike for rupturing calibration fluid pouch 355h of cartridge 10h (see FIGS. 20A, 21C and 21H) |
| 363h | Hole in spike 361h for draining calibration fluid from the calibration fluid pouch 355h of cartridge 10h (see FIG. 21H) |
| 364h | Duct for channeling calibration fluid from the calibration fluid spike hole 363h to duct 365h of cartridge 10h (see FIGS. 21E and 21H) |
| 365h | Duct for channeling calibration fluid from duct 364h to biosensor chamber 337h (via junction 367h and subsequently biosensor chamber entrance 336h) of cartridge 10h (see FIGS. 21E and 21H) |
| 367h | Junction where the duct 365h intersects with the biosensor chamber entrance 336h of cartridge 10h (see FIG. 21H). |
| 368h | Laminate for covering calibration fluid duct 364h and hole 363h in spike 361h of cartridge 10h (see FIGS. 21E and 21H) |
| 369k | Laminate for covering sample duct 385k and retaining spring 383k of cartridge 10k |
| 369m | Laminate for covering sample duct 385m of cartridge 10m |
| 371 | Elastomeric flap of a directional valve comprising a larger section 371 "for installation in cavity 372, and a smaller section 371" that is flappable for |

TABLE 1-continued

Description of Structural Features.

| Reference Numerals | Description of Structural Features |
|---|---|
| | closing off the blood passage when calibration fluid is being delivered to the biosensors, and for closing off the calibration fluid passage when blood is being delivered to the biosensor chamber of cartridge 10h (see FIGS. 20A, 20F and 21E). |
| 372 | Cavity in second housing member 30h for anchoring elastomeric flap 371 of cartridge 10h (see FIGS. 20A and 20D) |
| 375h | Recess in bottom of second housing member 30h of cartridge 10h for heating blood with heating pad installed in an analyzer |
| 375j | Recess in bottom of part 30j of cartridge 10j for heating blood with heating pad, installed in an analyzer |
| 376k | Elements of directional valve of cartridge 10k, comprising a ball 377k, a stem 379k attached to the ball, an O-ring 381k for sealing the valve at the stem during movement, and a spring 383k for keeping the ball in the up position |
| 376m | Elements of directional valve of cartridge 10m, comprising a ball, a stem attached to the ball, and a diaphragm attached to the stem |
| 377k | Ball of elements of directional valve 376k of cartridge 10k |
| 377m | Ball of elements of directional valve 376m of cartridge 10m |
| 378m | Diaphragm of elements of directional valve 376m of cartridge 10m |
| 379k | Stem attached to ball 377k of elements of directional valve 376k of cartridge 10k |
| 381k | O-ring of elements of directional valve 376k of cartridge 10k |
| 383k | Spring of elements of directional valve 376k of cartridge 10k |
| 385k | Sample duct in blood flow path of cartridge 10k (see FIGS. 24C, 256 and 25E, also FIGS. 266 and 26D) |
| 387k | Junction of blood and calibration fluid flow paths of cartridge 10k |
| 387m | Junction of blood and calibration fluid flow paths of cartridge 10m |
| 388k | Bottom seat in cartridge body for mating with ball 377k when the ball is in a down position, for closing off sample duct 385k |
| 390j | Cartridge exit duct for housing vacuum sealing member 353j |
| 390k | Cartridge exit duct for housing vacuum sealing member 353k |
| 390m | Cartridge exit duct for housing vacuum sealing member 353k |
| 391k | Calibration duct in cartridge 10k for housing calibration sealing member 354k |
| 391m | Calibration duct in cartridge 10m for housing calibration sealing member 354m |
| 393k | Internal segment of the calibration duct in cartridge 10k for receiving external calibration fluid stored in an analyzer used to measure one or more properties of a blood sample |
| 393m | Internal segment of the calibration duct in cartridge 10m for receiving external calibration fluid stored in an analyzer used to measure one or more properties of a blood sample |
| 441j | Sample storage well insert of cartridge 10j |
| 443j | Hole in cartridge 10j for accommodating sample storage well insert 441j |

Shown in FIG. 1A is an exploded view of an example of a disposable cartridge 10 for measuring one or more properties of a sample, the cartridge having a rapid sample metering system. From top to bottom, the components are described. Pin 60 is used to hingedly (pivotally) attach cap 50 to the cartridge, via pin hole 61 shown in the first housing member 20; the bottom of the pin hole 61 is shown as 63 in the second housing member 30. Flexible member 345 nests in a recess 347 in the first housing member 20 and is used to seal off the air bladder window 341. An optional cap sealing ring, or washer 57, may be attached to the underside of the cap 50. In some embodiments, the sealing ring/washer is referred to as a gasket, which may be made from several different materials known to a person skilled in the art. PTFE (Polytetrafluoroethylene, also known as Teflon) is a good example of gasket material. An advantage of PTFE in this application is that it has a very low surface energy (also described as a hydrophobic material or non-wettabale material) and can pass easily over sliding surface 49 of inlet portion 40 (see FIG. 2A), without dragging the blood sample as the seal 57 moves along the surface of inlet portion 40.

Also shown in the first housing member 20 is the first optical window 213, an air bladder exit port 344, the top portion 43 of a sample storage well 41 (see FIG. 1G), a cap latch 70, and the sample inlet portion 40. Sample inlet portion 40 comprises sample storage well 41 within top portion 43, air bladder exit port 344, pin hole 61, and sliding surface 49 that surrounds the top portion 43 of the sample storage well 41 and the air bladder exit port 344. Elements 40, (49, 344, 43) and 70 of cartridge 10 interact with the cap 50 as described in more detail below. Some embodiments of the cartridge described herein provide a good seal between the cap 50 and the sample inlet portion 40, without a cap latch 70, depending on the robustness of the hinged attachment of the cap. For example, the fourth embodiment of a cartridge (10d; see FIGS. 12A-12D) comprises a hinged or pivotal attachment of the cap 50d with no cap latch. Without a cap latch, greater amount of space is provided at the sample storage well 41, for accommodating the heel of a baby or a large adult finger. The provision of space at the sample storage well 41 is further described below, with reference to, for example, the fifth, sixth and seventh embodiments of the invention.

Still referring to FIG. 1A, there is shown a double-sided sticky gasket 100, comprising several gasket cut-outs, including:

cut-out 101, positioned to provide fluid connection between the bottom of a sample storage well and a sample storage conduit entrance 81 of cartridge 10;

cut-out 109 position to align with pin hole 61;

cut-outs 105, 107 and 103 are positioned to provide fluid connection between an air bladder cavity 340 (FIG. 3A) and air bladder exit port 344;

cut-out 115 position to align with capillary break or enlarged cavity 87;

cut-out 117 positioned to provide fluid connection between an optical chamber inlet conduit 217 (see FIG. 1G) and an optical chamber overflow conduit 227 (FIG. 1H), and positioned to align with optical windows 213 and 215 (FIG. 1H), in cartridge 10; cut-out 117 defines an optical chamber 211 (see FIG. 1H);

cut-out 119 positioned to provide fluid connection between the optical chamber overflow conduit 227 (FIG. 1H) and a waste receptacle 231 of cartridge 10.

Below gasket 100 is the second housing member 30, showing the following elements: a sample storage conduit entrance 81; a sample storage conduit groove 85 that defines the sample storage conduit 83 (FIG. 1G); the second portion 87" of capillary break 87 (see FIG. 1F); and a waste receptacle cavity 231.

The assembled cartridge body, comprising the first housing member 20, the sticky gasket 100, and the second housing member 30 may be made of a clear polymeric material, a clear plastic, a material that is transparent to a wavelength of electromagnetic radiation used to interrogate the sample, or a combination thereof. A person having ordinary skill in the art should understand that the cartridge construction is not limited to having a double-sided sticky gasket sandwiched by a first and a second housing member. This model is useful at least for illustrating the internal structural features or the cartridge.

Shown in FIG. 1B (view in conjunction with FIG. 2A) is a bottom view of the first housing member 20 of the cartridge shown in FIG. 1A showing the optical inlet conduit groove 219 that defines the optical chamber inlet conduit 217 when housing member 20 is attached to sticky gasket 100. Optical chamber inlet conduit 217 joins in fluid communication, the capillary break 87 with the optical chamber 211. Overflow conduit groove 229 defines the overflow conduit 227 (when housing member 20 is attached to sticky gasket 100) that fluidly connects the optical chamber 211 with the waste receptacle cavity 231 in the assemble cartridge. Also shown in FIG. 1B is a portion of the cartridge defining a bottom opening 45 of sample storage well 41, pin hole 61 and air bladder exit port 344. Shown in FIG. 1C is the bottom view of the first housing member 20 shown in FIG. 1B, overlaid by, and in alignment with, gasket 100 shown in FIG. 1A. Shown in FIG. 1D is a top view of the second housing member 30 of the cartridge shown in FIG. 1A. Shown in FIG. 1E is a top view of the second housing member 30 shown in FIG. 1D, overlaid by, and in alignment with the gasket 100 shown in FIG. 1A.

Shown in FIG. 1F is a top view of the cartridge 10 shown in FIG. 1A, with the cap 50 in a fully closed position. It will be shown later for cartridge embodiments that use negative pressure for regulating blood flow, that a cap in a fully closed position does not necessarily imply that the closed cap puts the cartridge in a sealed configuration. Illustrated in FIG. 1G is an enlarged cross-sectional view through the cartridge shown in FIG. 1F along line G-G, showing the sample storage well 41, the sample storage conduit entrance 81, the sample storage conduit 83, the sections 87' and 87" of the capillary break or enlarged cavity 87 (see hidden view in FIG. 1F), inlet conduit 217 of optical chamber 211 (see FIG. 1H), and cap handle 59. Shown in FIG. 1H is a second enlarged cross-sectional view through the cartridge shown in FIG. 1F along line H-H, showing an optical chamber 211 (defined by cut-out 117 of the double-sided sticky gasket 100), a first optical window 213, a second optical window 215, an optical chamber overflow conduit 227, a waste receptacle 231 and a vent 233. The optical chamber 211 is a non-limiting example of a detection chamber. Shown in FIG. 1J is a third cross-sectional view through the cartridge shown in FIG. 1F along line J-J, showing the sample storage conduit entrance 81, mating with the bottom opening 45 of the sample storage well 41. This mating aspect is better illustrated in FIG. 5H, regarding cartridge 10b and therefore, in some embodiments, the bottom opening 45 and the sample storage conduit entrance 81 are shown as a single structure.

The fifth, sixth and seventh embodiments of the disposable cartridge provide additional space at the cartridge inlet, in order to accommodate larger fingers and a baby's heel, when these body parts are used to provide the blood sample. Furthermore, the fifth, sixth and seventh embodiments described herein, permit the option to choose from a larger selection of materials, for example plastics, for manufacturing the cartridges.

Embodiments one to four require blood storage conduits that possess sufficient wetting ability (or wettability, or hydrophilicity) to draw the blood sample by capillary action, up to an enlarged section sometimes referred to as a capillary break, which stops blood flow by capillary action (i.e. the capillary action created in the enlarged section is not sufficient to draw the blood into the section). Wettability studies usually involve the measurement of contact angles, which indicates the degree of wetting when a solid and liquid interact.

For example, Table 2 lists contact angles, the angles between the plastic surface and the surface of a water drop on the plastic surface. The smaller the contact angle, the more wettable is the plastic. By way of illustration, a common example of a non-wettable or hydrophobic surface is Teflon (also known as Polytetrafluoroethylene [PTFE]), which has a contact angle of 109.2 (see Table 2). It is well known that water "beads" on a Teflon surface, accounting for the large contact angle; it is also well known that water "spreads" over a clean glass surface accounting for a small contact angle.

Table 2 provides a selection of plastics for manufacturing the cartridges, with compromises between wetting ability and optical clarity, which must be considered regarding cartridge functionality and cartridge manufacture. Other types of polymers can be blended to enhance or decrease the wettability of the blended polymer. A commonly used blended polymer is PETG, which is used to make plastic capillary tubes for collecting capillary blood. PETG has mostly replaced glass as an alternative to glass for safety concerns, for making capillary tubes used to collect capillary blood from babies. The manufacturer of PETG does not provide details of the PETG composition; PETG is a blend of PET (polyethylene terephthalate) and PEG (polyethylene glycol). PET has a contact angle of 72.5, and based on the inventor's experience, PET does not provide sufficient capillary action to draw blood into a disposable cartridge. While the contact angle of commercial PETG is not available, it is possible that other additives e.g., polystyrene, may be added to provide the required wettability (Kolahchi, A. R., AIP Conference Proceedings 1664, 030001, 2015). Other treatments, for example, plasma surface treatment and alteration of surface roughness can also be used to modify surface wettability.

TABLE 2

(obtained from DIVERSIFIED Enterprises, 101 Mulberry St., Suite 2, Claremont, NH 03743 U.S.A.)

| Polymer Names and Acronyms Commonly Used | Contact Angle |
| --- | --- |
| Polyvinyl alcohol (PVOH) | 51 |
| Polyvinyl acetate (PVA) | 60.6 |
| Nylon 6 (polycaprolactum, aramid 6) | 62.6 |
| Polyethylene oxide (PEO, PEG, polyethylene glycol) | 63 |
| Nylon 6,6 | 68.3 |
| Nylon 7,7 | 70 |
| Polysulfone (PSU) | 70.5 |
| Polymethyl methacrylate (PMMA, acrylic, plexiglas) | 70.9 |
| Nylon 12 | 72.4 |
| Polyethylene terephthalate (PET) | 72.5 |
| Epoxies | 76.3 |
| Polyoxymethylene (POM, polyacetal, polymethylene oxide) | 76.8 |
| Polyvinylidene chloride (PVDC, Saran) | 80 |
| Polyphenylene sulfide (PPS) | 80.3 |
| Acrylonitrile butadiene styrene (ABS) | 80.9 |
| Nylon 11 | 82 |
| Polycarbonate (PC) | 82 |
| Polyvinyl fluoride (PVF) | 84.5 |
| Polyvinyl chloride (PVC) | 85.6 |
| Nylon 8,8 | 86 |
| Nylon 9,9 | 86 |
| Polystyrene (PS) | 87.4 |
| Polyvinylidene fluoride (PVDF) | 89 |
| Poly n-butyl methacrylate (PnBMA) | 91 |
| Polytrifluoroethylene | 92 |
| Nylon 10,10 | 94 |
| Polybutadiene | 96 |
| Polyethylene (PE) | 96 |
| Polychlorotrifluoroethylene (PCTFE) | 99.3 |
| Polypropylene (PP) | 102.1 |
| Polydimethylsiloxane (PDMS) | 107.2 |
| Poly t-butyl methacrylate (PtBMA) | 108.1 |
| Fluorinated ethylene propylene (FEP) | 108.5 |
| Hexatriacontane | 108.5 |
| Paraffin | 108.9 |
| Polytetrafluoroethylene (PTFE) | 109.2 |
| Poly(hexafluoropropylene) | 112 |
| Polyisobutylene (PIB, butyl rubber) | 112.1 |

The disposable cartridge described herein may comprise an optical chamber, which is preferably made of transparent plastic. Some very transparent plastics, for example Polymethyl methacrylate (PMMA, plexiglass) and PET, can be injection molded, but may not be sufficiently wettable for the purpose of drawing blood by capillary action. In the fifth to seventh embodiments of the cartridge, the cartridge can function without relying on capillary action to draw the blood into the optical chambers of the cartridges. When capillary action is not relied upon, the positive air pressure from an air bladder is used to push the blood into the optical chamber in a regulated manner. Other similar embodiments use a combination of capillary action and positive air pressure from an air bladder, to respectively draw the blood into the optical chamber and push the blood out of the optical chamber, in a regulated manner. The different features described herein, for example the use of an air bladder, therefore provides more options for manufacturing the cartridges. Examples of cartridges (10j, 10k and 10m illustrated collectively in FIGS. 22A-27K) that use negative pressure to draw the blood into the detection chamber are also described below.

Shown in FIG. 2A is a top view of the cartridge 10 shown collectively in FIGS. 1A-1J, with the cap 50 and pin 60 removed to indicate the arrangement of components 61 (pin hole for receiving pin 60), 344 (air bladder exit port of sample inlet portion 40), 43 (top opening of sample storage well 41) and 47 (a sample overflow well). Element 47 may be considered as an element of the of sample inlet portion 40, but some cartridges, for example cartridge 10c, do not include a sample overflow well. Shown in FIG. 2B is a top view of the cartridge 10 shown collectively in FIGS. 1A-1J, with the cap 50 in a position indicating an unsealed configuration of the cartridge. In the unsealed configuration the cap 70 may rest against cap latch 70 as shown in FIG. 2A, and the cap latch may act as a cap stop to define the unsealed configuration. Shown in FIG. 2C is a top view of the cartridge 10 shown collectively in FIGS. 1A-1J, with the cap 50 in a position indicating a partly open configuration of the cartridge. Shown in FIG. 2D is a top view of the cartridge 10 shown collectively in FIGS. 1A-1J, with the cap 50 in a position indicating a sealed configuration of the cartridge. FIGS. 2B-2D illustrate how, by moving the position of cap 50, the cartridge is adjustable between an unsealed and a sealed configuration. In the sealed configuration shown in FIG. 2D, the cap 50 is engaged with cap latch 70, and the cap latch is acting as a cap stop to define the sealed configuration.

Referring to FIGS. 3A-3D are perspective views of the cartridge 10 shown in FIGS. 2A and 2D, providing more details of the sample inlet portion 40 and its association with the cap 50. Shown in FIG. 3A is a top perspective view of the cartridge 10 shown in FIG. 2A, with air bladder 340 open and the cap 50 removed. Shown in FIG. 3B is a detailed view of detail B of the cartridge shown in FIG. 3A, and indicates the arrangement of components 344, 61, 43, 47, and the cap latch recess 73 of cap latch 70. Shown in FIG. 3C is a top perspective view of the cartridge 10 with a flexible member 345 sealing off the air bladder window 341 (FIG. 1A) in order to define the air bladder 340, and cap 50 positioned over sample inlet portion 40 whereby the cartridge is adjusted in a sealed configuration. Shown in FIG. 3D is a detailed view of detail D of the cartridge shown in FIG. 3C. An outer periphery of cap 50 is shown to be engaged with cap latch recess 73 of cap latch 70. In this example, the cap latch recess 73 is operating as a latch to retain cap 50 in a closed position where the cartridge is in a sealed configuration. Also shown in FIG. 3D is cap handle 59, that is used to move cap 50 pivotally about pin 60.

The details of the cap 50 are illustrated in FIGS. 4A-4G. Shown in FIG. 4A is a top view of the cap 50 shown in FIG. 3D, showing pin hole 71 in cap 50 for receiving pin 60, the top side 51 of the cap 50, and a cap handle 59 for facilitating rotation of cap 50. Also shown are a sweeping portion 53 of cap 50 and a trailing portion 54 of cap 50, in the context of a counterclockwise rotation of the cap 50 about the pin 60, when the cartridge is adjusted from an unsealed configuration (see FIG. 2B) to a sealed configuration (see FIG. 2D). Shown in FIG. 4B is a top perspective view of the cap 50 shown in FIG. 4A. Shown in FIG. 4C is a front view of the cap 50 shown in FIG. 4A. Shown in FIG. 4D is a right side view of the cap 50 shown in FIG. 4A, indicating the underside 52 of cap 50. Shown in FIG. 4E is a bottom view of the cap 50 shown in FIG. 4A, showing a sweeping cap edge 58 disposed at the sweeping portion 53 of cap 50 for skimming off excess sample, and the cap recess 55. A flat surface surrounds the cap recess 55, the flat surface may comprise, for example, a sealing ring 57. In this example, the sweeping cap edge 58 is the edge of the cap sealing ring 57. Shown in FIG. 4F is a bottom perspective view of the cap 50 shown in FIG. 4E. Shown in FIG. 4G is a cross-sectional view through the cap 50 shown in FIG. 4E along line G-G, showing the top side 51 of cap 50, the cap recess 55, and the cap sealing ring 57.

Shown in FIG. 5A is an exploded view of the disposable cartridge 10b for measuring one or more properties of a sample, the cartridge having a rapid sample metering system, according to a second embodiment of the cartridge. This embodiment is similar to the first embodiment of the cartridge 10, and illustrated collectively in FIGS. 1A-4G, and accordingly, elements common to them share common reference numerals. For some elements, the letter "b" is appended to the end of the reference numerals, in order to indicate that the elements are part of the second embodiment of the cartridge. A first difference between the first (10; FIGS. 1A-4G) and second (10b; FIGS. 5A-8G) embodiments of the cartridge is that the shape of the cap 50 is circular and the shape of cap 50b is elliptical. It should be understood that these are examples of preferred embodiments, and the shape is not limited to being circular or elliptical. Cartridge 10g (see FIGS. 18A-19H) for example, provides a different, irregular, cap shape. Another non-limiting example is an oval shape that is not elliptical. An advantage of an ellipse, having a major radius and a minor radius, is that it is equivalent to a circle having a radius equal to the major radius of the ellipse, in the context of space between the latch 70b and the pin hole 61b (see FIGS. 5A and 6A), whereby the pin hole 61b is located at one end of the major axis of the ellipse. The larger space, illustrated in FIG. 6B (compare with illustration in FIG. 2B), is useful for accommodating larger fingers, if blood is obtained from a finger prick. Cartridges 10e, 10f and 10g (see FIGS. 14A-19H) provide even more space for accommodating even larger body parts. A second difference, between the first (10; FIGS. 1A-4G) and second (10b) embodiments of the cartridge, is that the pin 60b is an integral part of the cap 50b, as illustrated collectively in FIGS. 8A-8G. A third difference is that cartridge 10b comprises a mixing chamber 89 (see FIG. 5G), for mixing sample and one or more reagents. A fourth difference is that the detection system in the first embodiment of the cartridge is optical or spectrophotometric, whereas the detection system in the second embodiment is electrochemical or biosensors. A person of ordinary skill will appreciate that other embodiments of the cartridge can have either, both of the aforementioned detection systems, some other detection system, or any combination thereof. The fifth, sixth and seventh embodiments are examples of cartridges having two different detection systems. Other minor differences between the various disposable cartridges described herein will become obvious by following the reference numerals and the corresponding description of structural features provided in Table 1.

Shown in FIG. 5B is a bottom view of the first housing member 20b of the cartridge shown in FIG. 5A. Shown in FIG. 5C is the bottom view of the first housing member 20b shown in FIG. 5B, overlaid by and in alignment with the gasket 100b shown in FIG. 5A. Shown in FIG. 5D is a top view of the second housing member 30b of the cartridge shown in FIG. 5A. Shown in FIG. 5E is the top view of the second housing member 30b shown in FIG. 5D, overlaid by and in alignment with the gasket 100b shown in FIG. 5A, and with the biosensor array 330 installed.

Figure 5F:
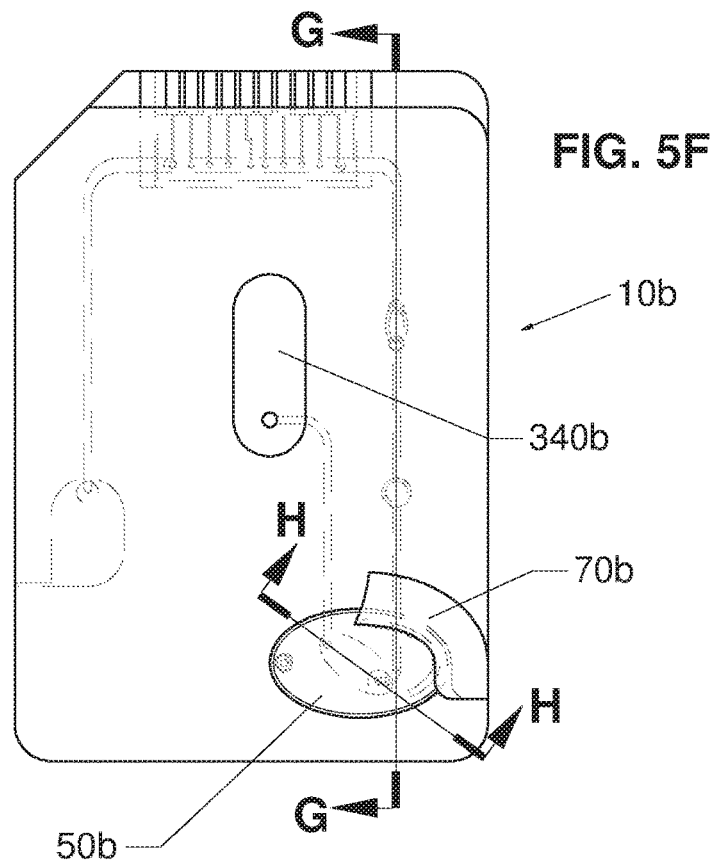
FIG. 5F is a top view of the cartridge 10b shown in FIG. 5A, with the cap 50b in a fully closed position, and air bladder 340b open.
Figure 5H:
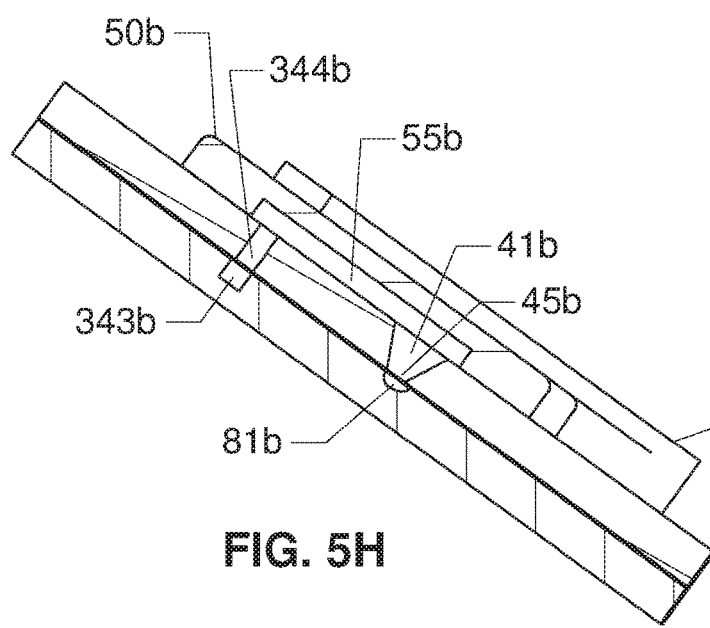
FIG. 5H is an enlarged second cross-sectional view through the cartridge 10b shown in FIG. 5F along line H-H.
Figure 5G:
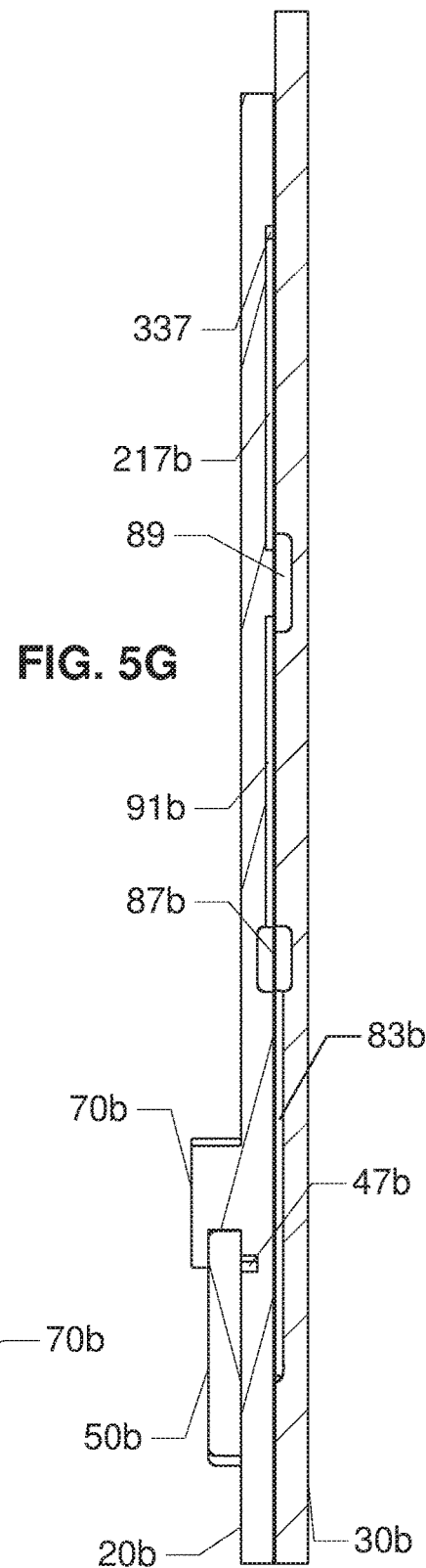
FIG. 5G is an enlarged first cross-sectional view through the cartridge 10b shown in FIG. 5F along line G-G.

Shown in FIG. 5F is a top view of the cartridge 10b shown in FIG. 5A, with the cartridge in a sealed configuration, and with the air bladder laminate 345b hidden, in order to view the air bladder 340b. Shown in FIG. 5G is an enlarged first cross-sectional view through the cartridge 10b shown in FIG. 5F along line G-G. Shown in FIG. 5H is an enlarged second cross-sectional view through the cartridge 10b shown in FIG. 5F along line H-H, illustrating the fluid connection between the air bladder duct 343b and the sample well 41b, via the air bladder exit port 344b and the cap recess 55b. The arrangement of the bottom portion 45b of the sample storage well 41b with the sample storage conduit entrance 81b, is also illustrated.

Shown in FIG. 6A is a top view of the cartridge 10b shown collectively in FIGS. 5A-5H, with the cap 50b hidden. Shown in FIG. 6B is a top view of the cartridge 10b shown collectively in FIGS. 5A-5H, with the cartridge in an unsealed configuration. Shown in FIG. 6C is a top view of the cartridge 10b shown in FIG. 6B, with the cap 50b in a partially open position. Shown in FIG. 6D is a top view of the cartridge 10b shown collectively in FIGS. 6B and 6C, with the cartridge in a sealed configuration. Shown in FIG. 6E is a cross-sectional view of cartridge 10b shown in FIG. 6D along line E-E. Shown in FIG. 6F is a detailed view of detail F of cartridge 10b shown in FIG. 6E, showing a snap-fit mechanism for engaging the cap 50b in the cartridge 10b shown collectively in FIGS. 6B-6D. Description of the structural features is provided in Table 1.

Shown in FIG. 7A is a perspective view of the cartridge 10b shown in FIG. 6A. Shown in FIG. 7B is a detailed view of detail B of the cartridge shown in FIG. 7A, showing details of the sample inlet portion 40b. Shown in FIG. 7C is a perspective view of the cartridge 10b shown in FIG. 6D. Shown in FIG. 7D is a detailed view of detail D of the cartridge shown in FIG. 7C. Description of the structural features is provided in Table 1.

Shown in FIG. 8A is a top view of the cap 50b shown in FIGS. 7C-7D, showing a sweeping portion 53b of cap 50b and trailing portion 54b of cap 50b, in the context of counterclockwise rotation of the cap 50b about the pin 60b, when the cartridge is adjusted from an unsealed configuration (see FIG. 6B) to a sealed configuration (see FIG. 6D). Shown in FIG. 8B is a perspective view of the cap 50b shown in FIG. 8A. Shown in FIG. 8C is a front view of the cap 50b shown in FIG. 8A, showing the top side 51b, the underside 52b, the pin 60b and a snap fit lip 65b for locking pin 60b in pinhole 61b. Shown in FIG. 8D is a right side view of the cap 50b shown in FIG. 8A. Shown in FIG. 8E is a bottom view of the cap 50b shown in FIG. 8A, showing a sweeping cap edge 58b disposed at the sweeping portion 53b of cap 50 for skimming off excess sample, and the cap recess 55b. In this embodiment of cap 50b, there is no gasket and the cap is made of suitable material that can provide a sealed configuration of the cartridge, making a gasket optional. In some embodiments, for example cartridge 10e, the gasket 57e is installed in the first housing member 20e of the cartridge 10e (see FIGS. 15B and 15H). Shown in FIG. 8F is a perspective view of the cap 50b shown in FIG. 8E. Shown in FIG. 8G is a cross-sectional view through the cap 50b shown in FIG. 8E along line G-G, showing the cap recess 55b and the pin snap fit lip 65b. The means provided for hingedly attaching the cap are examples only, and other means for hingedly attaching the cap to the body of the cartridge are considered to be within the scope of the invention. The first, second, third, fourth and seventh embodiments are examples of cartridges having a cap hingedly attached to the cartridge body, whereby the cap swings in a horizontal plane (i.e., the plane defined by the flat surface surrounding the sample storage well and the air bladder exit port, or a plane defined by the movement of the cartridge in and out of the analyzer cartridge receptor); the fifth, sixth, eighth, ninth, tenth and eleventh embodiments are examples of cartridges having a cap hingedly attached to the cartridge body, whereby the cap swings in a vertical plane substantially orthogonal to a plane defined by a surface surrounding the hinge.

Overview of Cartridge (Cartridge 10b Described as a Non-Limiting Example)

Measurement of any property of a liquid sample, for example glucose concentration or prothrombin time in blood, can be considered as non-limiting examples for illustrating the use of the cartridge. In this illustration, cartridge 10b will be used as a non-limiting example (see FIGS. 5A-8G). In general terms, the present disclosure provides a disposable cartridge for metering a sample for measuring one or more properties of the sample, the cartridge comprising:

1) a housing comprising a first housing member 20b and a second housing member 30b, bonded together by a double-sided sticky gasket 100b;

2) a cap 50b (FIGS. 4A-4F) having a top side 51b, an underside 52b, a sweeping cap edge 58b for skimming off excess sample, and a cap recess 55b in the underside 52b of the cap for creating a closed air passage illustrated in FIG. 5H;

3) a pin 60b for hingedly or pivotally attaching the cap 50b to an inlet portion 40b of the cartridge via pin hole 61b. The sample inlet portion 40b comprises elements of the cartridge that interact with the cap 50b, and may comprise:
 a) a top opening 43b of a sample storage well 41b for receiving the sample;
 b) the sample storage well 41b for storing a portion of the sample;
 c) a sliding surface 49b (see FIGS. 6A and 6B) for frictionally engaging the cap 50b;
 d) a hole 61b for receiving the pin 60b for hingedly attaching the cap 50b to the sample inlet portion 40b;
 e) a sample overflow well 47b for receiving the excess sample during the period of closing the cap 50b; in some examples of the cartridge, for example, cartridges 10c and 10d, the sample overflow well 47b is optional. With respect to cartridge 10c, the sweeping portion 53c of the cap 50c (see FIG. 10A) comprises a groove 48c disposed in the underside of the cap in front of the sweeping edge 58c (see FIG. 10F), for holding excess sample;
 f) a cap latch 70b, for facilitating a sealed configuration of the cartridge when a portion of the cap 50b is engaged with cap latch recess 73b; and
 g) an air bladder exit port 344b in fluid communication with an air bladder 340b.

4) the air bladder 340b for providing pressurized air to the air bladder exit port 344b;

5) a capillary break 87b (see FIG. 5G) for stopping sample flow, the flow being facilitated by capillary action;

6) a post capillary break conduit 91b providing fluid communication between the capillary break 87b and a mixing chamber 89 (see FIG. 5G);

7) a detection chamber (a conduit 337 over the active area 323, shown in FIGS. 5G and 5E respectively) comprising one or more biosensors of a biosensor array 330; in the case of cartridge 10, the detection chamber is the optical chamber 211 (see FIG. 1H) for generating one or more signals used to determine or calculate one or more properties of the sample;

8) a waste receptacle cavity 231b (see FIGS. 5A and 5D) for receiving fluid flowing beyond the detection chamber via the distal end of biosensor conduit groove 335 (see FIG. 5B) and gasket cut out 119b (see FIG. 5A); and 9) a vent 233b (see FIG. 5D) for relieving pressure in the waste receptacle cavity 231b.

Figure 17H:
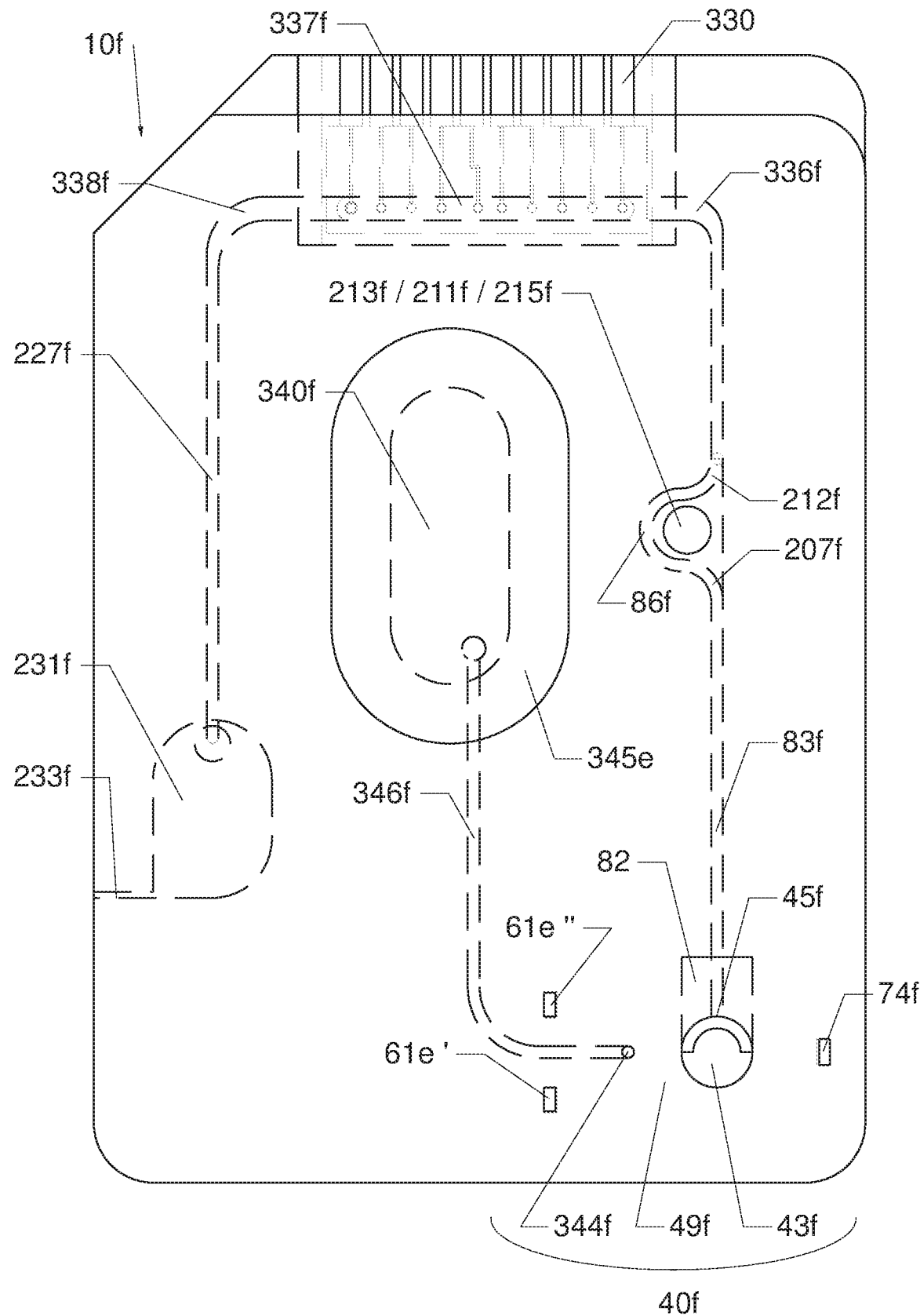
FIG. 17H is a top view of the cartridge 10f, with the cap hidden.

Another non-limiting example of a sample inlet portion is provided with reference to cartridge 10f illustrated in FIGS. 16A-17H. It should be appreciated that a sample inlet portion 40f does not define a particular structure of a cartridge, and the intent of the description of an inlet portion is to describe some elements of the cartridge that interact with the cap. Therefore, some drawings, e.g. FIG. 17H, illustrate the inlet portion 40f as comprising elements 43f (top opening of a sample storage well 41f of cartridge 10f), 344f (an air bladder exit port of a sample inlet portion 40f of cartridge 10f), and 49f (a flat surface surrounding the sample storage well and the air bladder exit port of cartridge 344f of 10f). In other words, the description of the inlet portion for one cartridge may be different from the description of the inlet portion of another cartridge.

The cartridge may be pre-loaded with one or more dry reagents deposited at one or more points before the detection chamber 323 (FIG. 5E; or for cartridge 10, the optical window defined by 213/211/215, FIG. 1H; or for cartridge 10c, the optical window defined by 213c/211c/215c, FIG. 11C). Cartridge 10b comprises an optional mixing chamber 89, and a post capillary break conduit 91b, which defines the conduit between the capillary break 87b and the mixing chamber 89, illustrated in FIG. 5G. In some cartridge embodiments, the one or more reagent is deposited in the mixing chamber 89. Dry thromboplastin is an example of a reagent, which is used for measuring prothrombin time (PT) usually reported as PT-INR (PT-International Normalized Ratio), and dry celite or kaolin are examples of a reagent used for measuring activated clotting time (ACT).

The cartridge is adjustable between an unsealed configuration and a sealed configuration. In the unsealed configuration illustrated in FIG. 6B, the top opening 43b of sample storage well 41b is configured to receive the sample, and the air bladder exit port 344b (view in conjunction with FIG. 6A) is optionally covered by the cap 50b. In the sealed configuration illustrated in FIGS. 5F and 5H, the cap recess 55b facilitates provision of a closed air passage connecting the air bladder exit port 344b and the sample storage well 41b for transferring pressurized air from the air bladder exit port 344b to the sample storage well 41b. As the cartridge is adjusted from the unsealed configuration to the sealed configuration (an intermediate configuration is illustrated in FIG. 6C), the sweeping cap edge 58b skims off excess sample above the top opening 43b (see FIG. 6C in conjunction with FIG. 5H) of the sample storage well 41b. The volume of sample in the cartridge in the sealed configuration is equivalent to the volume measured from the top opening 43b of the sample storage well 41b to the capillary break 87b (FIG. 5G). The sample storage well 41b also comprises a bottom opening 45b of the sample storage well 41b. In this example, the top 43b is substantially larger than the bottom 45b, as illustrated in FIG. 5H. Having a larger top opening 43b may assist in transferring a drop of blood from a body part, for example a finger, to the sample storage well 41b. In the case of a small infant, a heel is a preferred body part. The size of the smaller bottom opening 45b is preferably similar to the size of the sample storage conduit entrance 81b, for facilitating blood flow by capillary action. In some embodiments, bottom opening 45b and the sample storage conduit entrance 81b coincide, for example as shown in FIG. 5H (for cartridge 10b), and for example FIGS. 17G and 17H regarding cartridge 10f; only bottom opening 45f is shown. For a person having ordinary skill in the art, it should be understood that the bottom opening (element 45) of the sample storage well and the sample storage conduit entrance (element 81) may refer to the same structure.

Once the cartridge is in the sealed configuration, the cartridge is ready to be inserted into a slot or receptor of an analyzer. The analyzer detection system comprises one or more of, optical, spectrophotometric, fluorescence, chemiluminescence, electrochemical, biosensor, amperometric, potentiometric or conductimetric technology. However, these are just examples and other detection systems are considered to be within the scope of the present invention. These detection systems are known to a person skilled in the art and for the sake of brevity, will not be discussed here.

In the case of spectrophotometric or optical measurement, an embodiment of an analyzer comprises a source of electromagnetic radiation (EMR) and one or more photodetectors for measuring the EMR reflected from the optical chamber or transmitted through the optical chamber. In some embodiments of the analyzer, more than one photodetector are arranged as a linear diode array in a spectrometer, the spectrometer also comprising a transmission or reflection grating for dispersing the reflected EMR or transmitted EMR, into component wavelengths. Therefore, the analyzer optionally provides optical measurement at one or more wavelengths.

Another feature of the cartridge is the flexible member 345$b$ of the cartridge 10$b$. This flexible member 345$b$ may be depressed to generate pressurized air for mixing the sample with one or more dry reagent, and for advancing the sample towards the detection chamber in a regulated manner. This is facilitated by the fluid connection between an air bladder exit port 344$b$ and a sample well 41$b$, via a cap recess 55$b$, illustrated in FIG. 5H. The flexible member may also be repeatedly depressed and released causing the blood to move forward and backward, in order to dissolve the one or more dry reagent in the blood sample, and provide better mixing of sample and reagent. In other embodiments, for example cartridge 10$e$, the recess 55$e$ (see FIGS. 15G and 15H), is in the cartridge body instead of the cap 51$e$. In each case a closed passage connecting an air bladder and a sample storage well is formed when the cartridge is adjusted from an unsealed to a sealed configuration.

A method for measuring a property of a blood sample comprises some or all of the following steps, not necessarily in the sequence given. One step is providing a cartridge (for example, one shown as 10, 10$b$, 10$c$ or 10$d$) and an analyzer comprising a slot or receptor for receiving a cartridge, the cartridge comprising one or more dry reagent deposited at one or more points between the sample storage well and the detection chamber. Cartridge 10$b$ comprises an optional mixing chamber 89, and a post capillary break conduit 91$b$ that defines the conduit between the capillary break 87$b$ and the mixing chamber 89, illustrated in FIG. 5G. In some cartridge embodiments, the one or more reagents are deposited in the mixing chamber 89. Dry thromboplastin is an example of a reagent, which is used for measuring prothrombin time (PT) usually reported as PT-INR (PT-International Normalized Ratio), and dry celite or kaolin are examples of reagents used for measuring activated clotting time (ACT). It should be understood that PT-INR and ACT are just examples of properties of a blood sample, and the present invention is not limited in any way to the properties explicitly mentioned. Other examples of blood coagulation properties include partial thromboplastin time (PTT) and activated partial thromboplastin time (aPTT or APTT); PTT/aPTT are similar to ACT, except plasma is usually used in the laboratory to measure PTT/aPTT and whole blood is usually used to measure ACT in POCT. Another useful POCT that can be performed is thrombin time (TT) or thrombin clotting time. The thrombin time evaluates that part of the hemostatic process where soluble fibrinogen is changed into fibrin threads. In the laboratory, TT measures the time required for a fibrin clot to form following the addition of a standard amount of thrombin to plasma. The inventor is not aware of any POCT that measures TT using whole blood. Preferably, the detection system is for measuring TT is optical, as illustrated in cartridge 10$c$. TT is affected by the level and/or function of fibrinogen and the presence of inhibitors (e.g., heparin, fibrinogen/fibrin degradation products, direct thrombin inhibitor). With the addition of thrombin as the reagent, the thrombin time bypasses the rest of the coagulation factors and focuses on the function of fibrinogen. It should also be understood that the properties are not limited to blood coagulation properties, and include, for example without being limited in any way, hormones, drugs, enzymes, proteins, carbohydrates, lipids, amino acids and metabolites of the aforementioned.

In another step, the cartridge is placed flat on a table, and the cap 50$b$ is rotated in a clockwise direction until the cap 50$b$ hits the latch 70$b$, adjusting the cartridge 10$b$ to the unsealed configuration, as illustrated in FIG. 6B. It should be noted that in the fully unsealed configuration, the cap 50$b$ creates maximum opening of the top 43$b$ of the sample storage well 41$b$, and at the same time, the cap 50$b$ covers the air bladder exit port 344$b$, thereby mitigating flow of blood into the air bladder exit port 344$b$.

In another step, a blood sample is allowed to touch the top opening 43$b$ of the sample storage well 41$b$. The blood is drawn into the sample storage well 41$b$ and into the sample storage conduit 83$b$, up to the capillary break 87$b$ (see FIG. 5G). Slightly excess blood is applied so that the blood sample bulges above the top opening 43$b$ of the sample storage well 41$b$. For example, a finger of the patient may be pricked, and after a drop of blood is allowed to develop on the finger, following best practice procedures, a sample of the blood is introduced to the top opening 43$b$ as described above.

In another step, the cap 50$b$ is rotated counterclockwise into the recess 73$b$ of the cap latch 70$b$, as illustrated in FIG. 6D. Details of the sample inlet portion 40$b$ and its association with cap 50$b$ are illustrated collectively in FIGS. 7A-7D. During the cap movement, the sweeping cap edge 58$b$ (see FIGS. 8E and 8F) skims off excess blood, which is dumped into the sample overflow well 47$b$. The volume of the metered blood is the sum of the volume of the sample storage well 41$b$ and the volume of the sample storage conduit 83$b$. When the cap 50$b$ is fully inserted into cap latch recess 73$b$, the cartridge in the sealed configuration. A person of ordinary skill in the art should appreciate that an overflow well like 47$b$ is useful for keeping all the blood in a contained system to avoid blood contamination of the analyzer, but it is not essential for the function of the cartridge or the metering system described herein.

In another step, the cartridge in the sealed configuration is inserted in the slot or receptor of the analyzer (not shown). The steps following cartridge insertion may be performed by the analyzer automatically, and includes depression of the flexible member 345$b$. The flexible member 345$b$ can also be repeatedly depressed and released causing the blood to move forward and backward, in order to dissolve the dry one or more reagent in the blood sample. Depression or (repeated depression followed by release) of the flexible member 345$b$ may be performed by a small stepper motor mounted on the receptor of the analyzer, but other means may be used that is known by a person skilled in the art. In the case of cartridge 10$b$, which comprises an optional mixing chamber 89, the turbulence created as the blood sample flows into the mixing chamber 89 is sufficient to dissolve the one or more reagent, depending on the nature of the one or more reagent. It is known that some lyophilized reagents in relatively small quantities will dissolve almost immediately after the blood sample makes contact with the lyophilized substance, for example thromboplastin, used for measuring prothrombin time. It is also known that some reagents can be coated on the walls of a conduit, and more mixing may be required to dissolve the reagents from the conduit walls.

In the case of cartridge 10, which has an optical detection chamber, another step is to apply a pre-developed calibration algorithm (see for example, U.S. Pat. No. 6,651,015 to Samsoondar, which is incorporated herein by reference). Hematocrit may be measured using optical measurement of the unclotted or clotted blood at one or more wavelengths, and the hematocrit measurement may be used to correct the PT-INR for the patient's hematocrit.

Overview of Cartridges (Cartridges 10c and 10d as Non-Limiting Examples)

Disposable cartridges 10c and 10d for measuring one or more properties of a sample, the cartridges having rapid sample metering systems, will now be described (See FIGS. 9A to 13B). The detection system is optical, but other embodiments of similar cartridges may use different detection systems.

Shown in FIG. 9A is an exploded view of the disposable cartridge 10c for measuring one or more properties of a sample, the cartridge having a rapid sample metering system, according to a third embodiment of the cartridge. This embodiment is similar to cartridge 10b and the major differences are as follows: a) The detection system is optical instead of electrochemical; b) The latch 70c is a pivotal latch having a pivot 62c, instead of a stationary latch 70b illustrated collectively in FIGS. 7A to 7D; c) The sample storage conduit 83c is disposed at the bottom of the second housing member 30c, defined by a groove 85c and a bottom cover 351c (see FIGS. 9H and 11B); and d) The cap 50c is designed differently and discussed in greater detail later. Other differences will become apparent as the other drawings are described and viewed in conjunction with description of structural features provided in Table 1.

Shown in FIG. 9B is a bottom view of the first housing member 20c of the cartridge shown in FIG. 9A. Shown in FIG. 9C is the bottom view of the first housing member 20c shown in FIG. 9B, overlaid by and in alignment with the gasket 100c shown in FIG. 9A. Shown in FIG. 9D is a top view of the second housing member 30c of the cartridge shown in FIG. 9A. Shown in FIG. 9E is the top view of the second housing member 30c shown in FIG. 9D, overlaid by and in alignment with the gasket 100c shown in FIG. 9A.

Figure 9F:
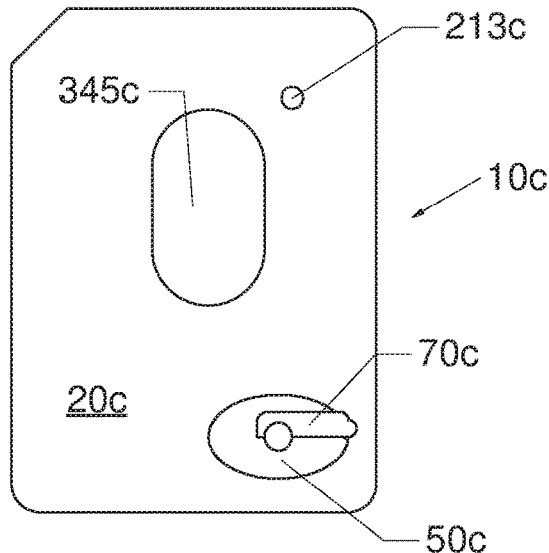
FIG. 9F is a top view of the cartridge 10c shown in FIG. 9A, with the cap 50c in a fully closed and latched position, showing the upper surface.
Figure 9J:
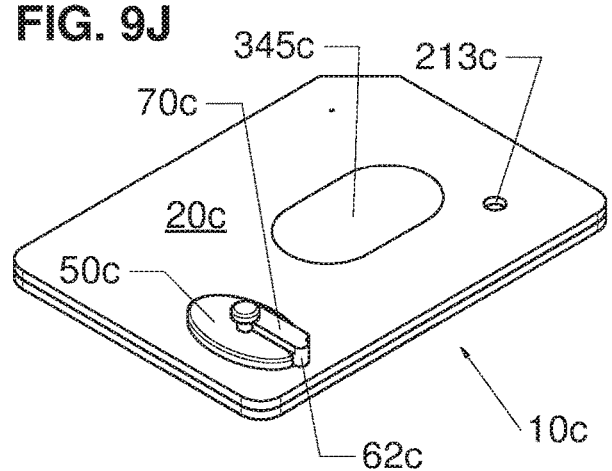
FIG. 9J is a perspective view of the cartridge 10c shown in FIG. 9F, showing the top or upper surface.
Figure 9G:
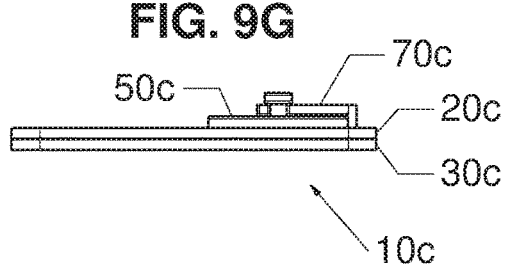
FIG. 9G is a front view of the cartridge 10c shown in FIG. 9F.
Figure 9K:
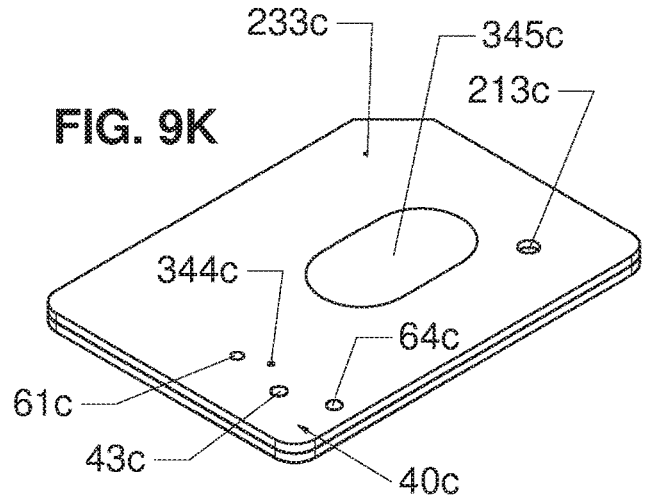
FIG. 9K is the perspective top view of the cartridge 10c shown in FIG. 9J. with the cap 50c and latch 70c removed.
Figure 9H:
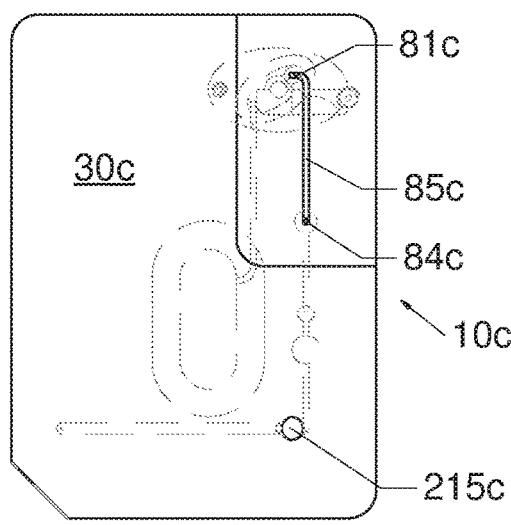
FIG. 9H is a bottom view of the cartridge 10c shown in FIG. 9F, with bottom cover 351c removed to expose the sample storage conduit groove 85c set in the lower surface.
Figure 9L:
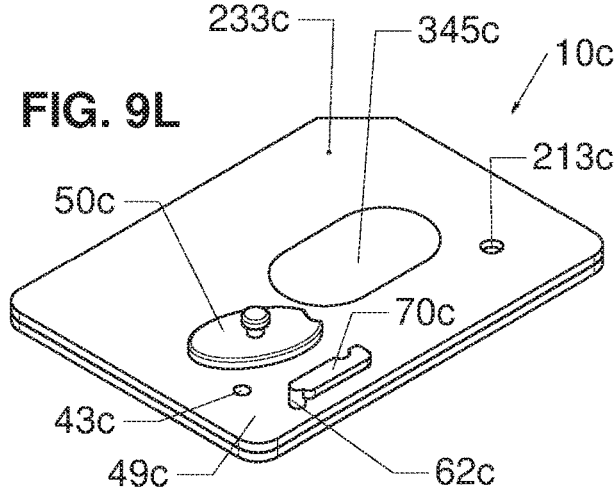
FIG. 9L is a top view of the cartridge 10c shown in FIG. 9A, with the cap 50c in a fully open position, showing the upper surface.

Shown in FIG. 9F is a top view of the cartridge 10c shown in FIG. 9A, with the cartridge 10c in a sealed configuration and latch 70c engaged with the cap 50c. Shown in FIG. 9G is a front view of the cartridge 10c shown in FIG. 9F. Shown in FIG. 9H is a bottom view of the cartridge 10c shown in FIG. 9F, with bottom cover 351c (see FIG. 9A) removed to expose sample storage conduit entrance 81c, the sample storage conduit groove 85c, and the junction 84c of sample storage conduit 83c and capillary break 87c (see FIG. 11B). Shown in FIG. 9J is a perspective view of the cartridge 10c shown in FIG. 9F. Shown in FIG. 9K is the perspective view of the cartridge 10c shown in FIG. 9J. with the cap 50c and latch 70c hidden in order to view the sample inlet portion 40c. Shown in FIG. 9L is a top view of the cartridge 10c shown in FIG. 9A, with the cartridge in an unsealed configuration. Latch 70c is shown swiveled clockwise about 90 degrees from its position shown in FIG. 9F where the cartridge is shown in a sealed configuration.

Figure 10A:
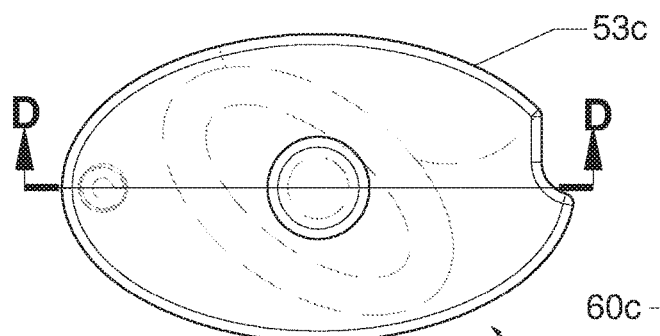
FIG. 10A is a top view of the cap 50c shown in FIGS. 9A, 9F, 9J and 9L.
Figure 10E:
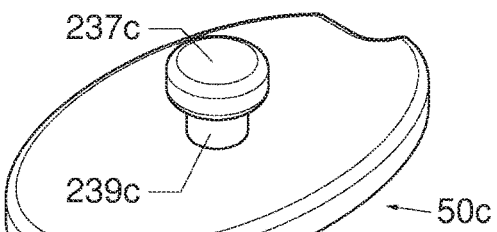
FIG. 10E is a perspective top view of the cap 50c shown in FIG. 10A.
Figure 10B:
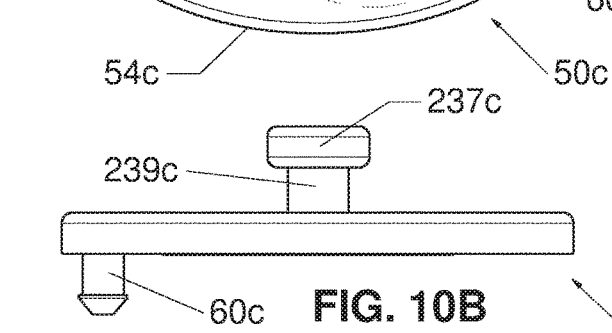
FIG. 10B is a front view of the cap 50c shown in FIG. 10A.

Illustrated collectively in FIGS. 10A-10H are details of the cap 50c. Shown in FIG. 10A is a top view of the cap 50c shown in FIGS. 9A, 9F, 9J and 9L, showing a sweeping portion 53c and a trailing portion 54c of cap 50c. Shown in FIG. 10B is a front view of the cap 50c shown in FIG. 10A, showing a pin 60c for hingedly attaching the cap to the sample inlet portion 40c and allowing the cap to swing with the gasket 57c (installed in cap 50c) frictionally engaged with the sliding surface 49c of inlet portion 40c. Also shown is a crown 237c and a neck 239c of a cap knob of cap 50c, the neck 239c used for engaging the latch 70c and the crown 237c used for handling the cap 50c.

Figure 10F:
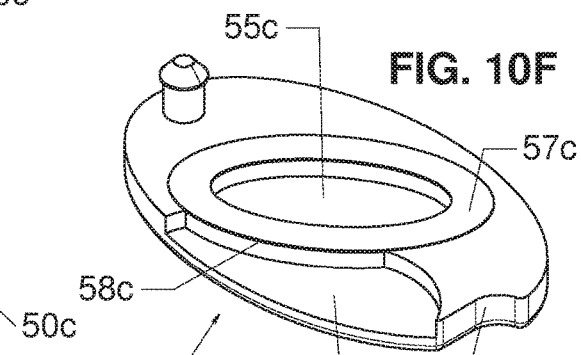
FIG. 10F is a perspective bottom view of the cap 50c shown in FIG. 10C.
Figure 10C:
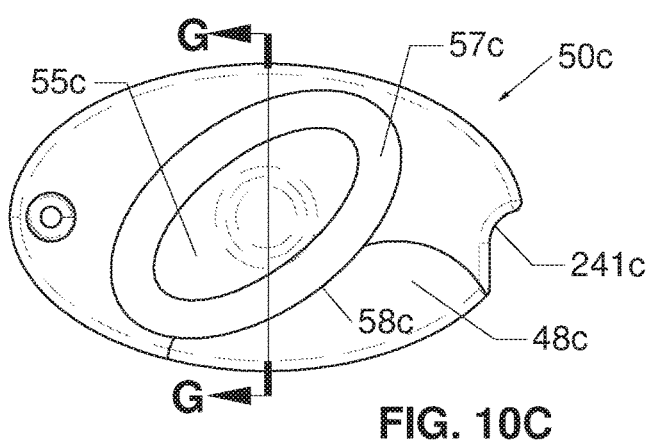
FIG. 10C is a bottom view of the cap 50c shown in FIG. 10A.
Figure 10G:
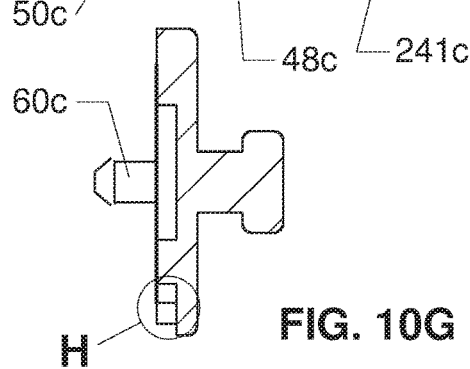
FIG. 10G is a cross-sectional view through the cap 50c shown in FIG. 10C along line G-G.
Figure 10D:
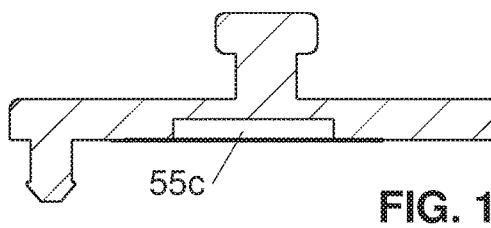
FIG. 10D is a cross-sectional view through the cap 50c shown in FIG. 10A along line D-D.
Figure 10H:
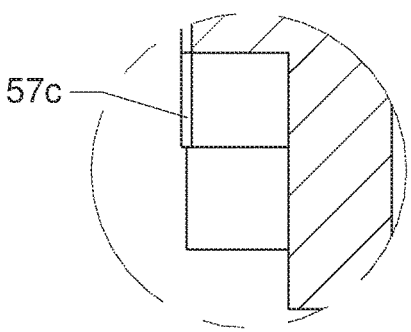
FIG. 10H is a detailed view of detail H of the cap 50c shown in FIG. 10G.

Shown in FIG. 10C is a bottom view of the cap 50c shown in FIG. 10A, showing a cap recess 55c, the gasket 57c, a groove 48c disposed at the underside and at the sweeping portion 53c of the cap 50c, for storing excess sample. Also shown is a sweeping cap edge 58c disposed at the sweeping portion 53c of cap 50c for skimming off excess sample, and a notch 241c in cap 50c for mating with pivot 62c of latch 70c, when cartridge 10c is in a sealed configuration. Shown in FIG. 10D is a cross-sectional view through the cap 50c shown in FIG. 10A along line D-D. Shown in FIG. 10E is a perspective view of the cap 50c shown in FIG. 10A. Shown in FIG. 10F is a perspective view of the cap 50c shown in FIG. 10C. Shown in FIG. 10G is a cross-sectional view through the cap 50c shown in FIG. 10C along line G-G. Shown in FIG. 10H is a detailed view of detail H of the cap 50c shown in FIG. 10G, showing the gasket 57c slighted elevated above the rest of the underside of the cap for creating the sweeping cap edge 58c.

Shown in FIG. 11A is a top view of the cartridge 10c (similar to the view shown in FIG. 9F) with the cartridge in a sealed configuration, for illustrating the internal structure. Shown in FIG. 11B is a first enlarged cross-sectional view through the cartridge 10c shown in FIG. 11A along line B-B. It should be noted that sufficient clearance between the crown 237c of the cap knob and the latch 70c is provided, and latch 70c is in contact with the cap 50c, in order for the latch 70c to apply downward force on the cap 50c, when the cartridge in a sealed configuration. Also shown in FIG. 11B is the separate reagent chamber 209c and mixing chamber 89c. The perspective and top view of the reagent chamber 209c and the portion 89c" of mixing chamber 89c in a second housing member 30c, are shown in FIG. 9A and FIG. 9D respectively. The volume of the mixing chamber is substantially larger than the volume of the reagent chamber, and the two chambers are fluidly connected by a narrow conduit 210c. After the sample fills the reagent chamber 209c containing the dry reagent, the reagent and sample are mixed more thoroughly by turbulence, after the partially mixed sample and reagent are ejected into the larger mixing chamber 89c. Shown in FIG. 11C is a second enlarged cross-sectional view through the cartridge 10c shown in FIG. 11A along line C-C, showing the optical chamber 211c, having an overflow conduit 227c, and a vent 233c for relieving pressure in the chambers and therefore allowing flow. Shown in FIG. 11D is a third enlarged cross-sectional view through the cartridge 10c shown in FIG. 11A along line D-D. Shown in FIG. 11E is a fourth enlarged cross-sectional view through the cartridge 10c shown in FIG. 11A along line E-E. By way of example, latch 70c is engaged with cartridge 10c in a similar manner as illustrated in FIG. 6F, for the engagement of cap 50b with cartridge 10b.

Figure 12A:
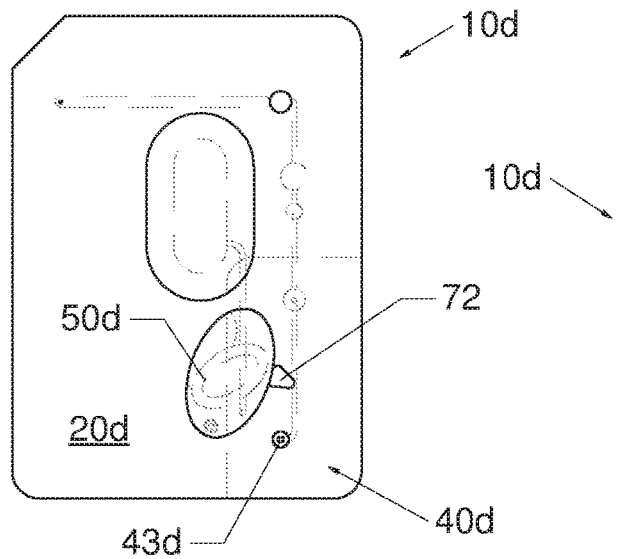
FIG. 12A is top view of the disposable cartridge 10d for measuring a property of a sample, the cartridge having a rapid sample metering system, according to a fourth embodiment of the cartridge, in a fully open position.
Figure 12B:
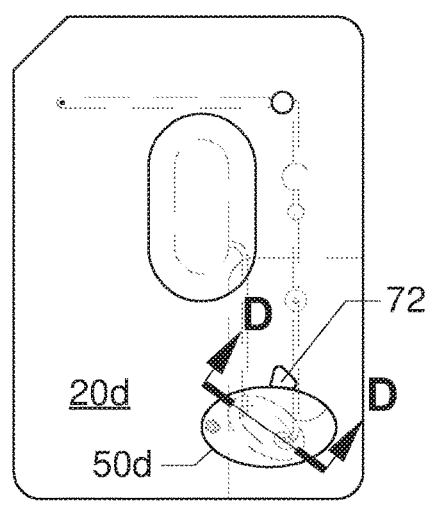
FIG. 12B is top view of the disposable cartridge 10d shown in FIG. 12A, but in a fully closed position.
Figure 12C:
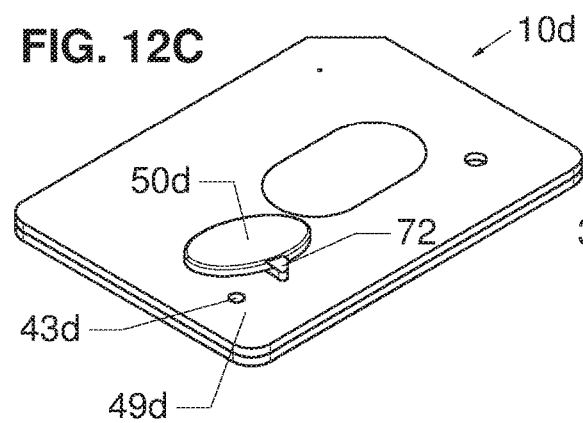
FIG. 12C is perspective top view of the disposable cartridge 10d shown in FIG. 12A (in a fully open position)

Shown in FIG. 12A is top view of the disposable cartridge 10d for measuring one or more properties of a sample, the cartridge having a rapid sample metering system, according to a fourth embodiment of the cartridge, in an unsealed configuration. Cartridge 10d is like cartridge 10c illustrated collectively in FIGS. 9A-9L and FIGS. 11A-11E. The major differences are: a) The cap 50d does not have a knob (239c and 237C) or a notch 241c; b) The cartridge 10c does not have a latch 70c; and c) The cartridge 10d comprises a cap stop 72 for keeping cartridge 10d in either an unsealed configuration or a sealed configuration. Shown in FIG. 12B is top view of the disposable cartridge 10d shown in FIG. 12A, but in a sealed configuration. Shown in FIG. 12C is perspective view of the disposable cartridge 10d shown in FIG. 12A (in an unsealed configuration).

Figure 12D:
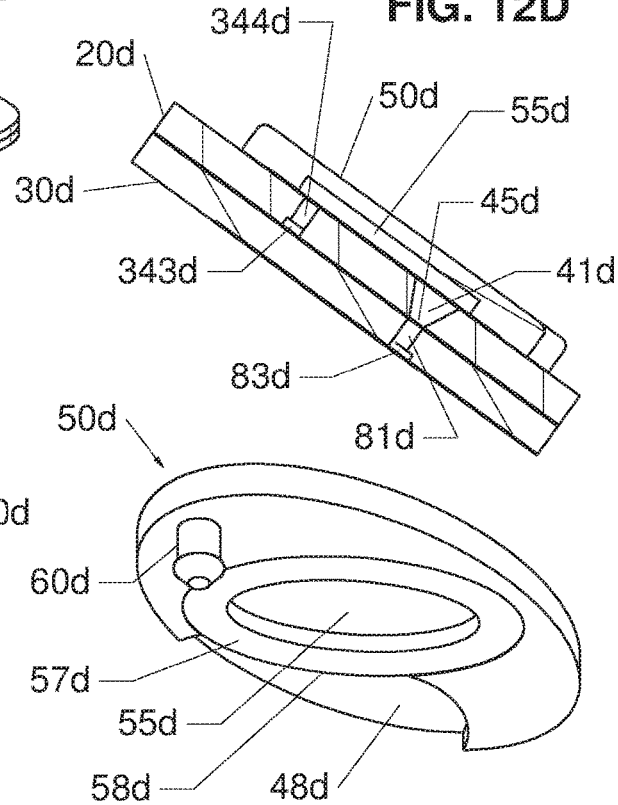
FIG. 12D is an enlarged cross-sectional view through the cartridge 10d shown in FIG. 12B along line D-D.

Shown in FIG. 12D is an enlarged cross-sectional view through the cartridge 10d shown in FIG. 12B along line D-D, showing the cap recess 55d providing a closed air passage connecting the air bladder exit port 344d and the sample storage well 41d for communicating the pressurized air from the air bladder exit port to the sample storage well for urging the sample into the reagent chamber (See 209c in FIG. 11B for cartridge 10c), the mixing chamber (See 89c in FIG. 11B for cartridge 10c), and the optical chamber (See 211c in FIG. 11C for cartridge 10c), in that order.

Figure 13A:
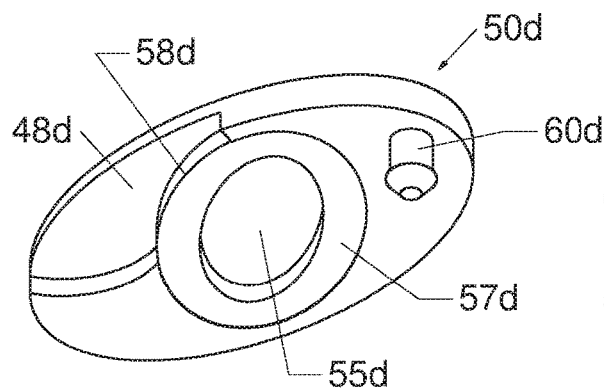
FIG. 13A is a first perspective bottom view of the cap 50d shown in FIG. 12A, showing the underside.
Figure 13B:
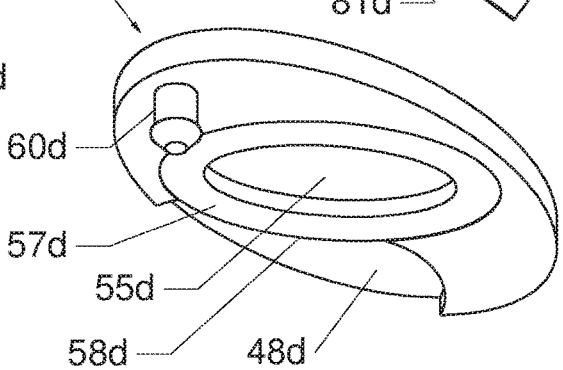
FIG. 13B, is a second perspective bottom view of the cap 50d shown in FIG. 12A, showing the underside.

Shown in FIG. 13A is a first perspective view of the cap 50d shown in FIG. 12A, showing the underside, and shown in FIG. 13B is a second perspective view of the cap 50d shown in FIG. 12A, showing the underside.

Sample Measurement

The following is a brief description of a system for metering a sample and measuring one or more properties of the sample, using one of the cartridges previously described explicitly or implicitly. The system further comprises an analyzer. The analyzer comprises: a) a receptor for receiving the cartridge; b) one or more processors for controlling the analyzer and calculating the one or more properties of the blood sample from the one or more signals received by the one or more detectors; c) means for activating the air bladder; and d) one or more detectors for receiving one or more signals from the detection chamber and sending the one or more signals to the one or more processors for transforming the one or more signals into the one or more properties of the sample.

The following is a description of a method for measuring one or more properties of a blood sample, using one of the cartridges previously described explicitly or implicitly. The method comprises some or all of the following steps, not necessarily in the sequence given: a) providing the cartridge in an unsealed configuration; b) providing an analyzer comprising: 1) a receptor for receiving the cartridge; 2) one or more processors for controlling the analyzer; 3) means for activating the air bladder; and 4) one or more detectors for receiving the one or more signals from the detection chamber and sending the one or more signals to the one or more processors for transforming the one or more signals into the one or more properties of the sample; c) obtaining a blood sample by pricking a body part and depositing the blood sample into the sample storage well, or depositing blood from a syringe into the sample storage well; d) rotating the cartridge cap about the pin and skimming off excess blood; e) arranging the cartridge in a sealed configuration, wherein the cap recess facilitates provision of a closed air passage connecting the air bladder exit port and the sample storage well for communicating pressurized air from the air bladder exit port to the sample storage well for urging the blood towards the detection chamber; f) inserting the sealed cartridge into the analyzer receptor; g) activating the air bladder for providing the pressurized air; h) dissolving the one or more reagents into the blood; i) urging the mixture of blood and the one or more reagents into the detection chamber; and j) measuring the one or more properties of the blood sample.

Some methods for measuring one or more properties of a blood sample, for example prothrombin time (or activated clotting time), further comprise: a) providing a cartridge further comprising an optical chamber; b) providing an analyzer further comprising a source of electromagnetic radiation and a detector for collecting electromagnetic radiation transmitted through the unclotted or clotted blood in the optical chamber or reflected from the unclotted or clotted blood in the optical chamber; c) applying a pre-determined calibration algorithm to the collected electromagnetic radiation to measure hematocrit of the blood sample to produce a hematocrit measurement; and d) using the hematocrit measurement to correct the property of the blood sample, for example prothrombin time (or activated clotting time), for the actual plasma volume in the blood sample.

Overview of Cartridges (Cartridges 10e, 10f and 10g as Non-Limiting Examples)

Described next are the fifth, sixth and seventh embodiments of a disposable cartridge (see FIGS. 14A-19H). These embodiments provide more space at the cartridge inlet and free from obstruction, in order to accommodate larger fingers and a baby's heel, when these body parts are used to provide the blood sample. Another advantage of the fifth, sixth and seventh embodiments is the option to choose from a larger selection of plastics for manufacturing the cartridges. As previously mentioned, an aspect of the present invention is an optical chamber, which is preferably made of transparent plastic and is easily manufactured by for example, injection molding. Some very transparent plastics, for example Polymethyl methacrylate (PMMA, plexiglass) and PET, are advantageous in terms of optical clarity and can be injection molded but may not be sufficiently wettable for the purpose of drawing blood into the optical chamber by capillary action. The fifth, sixth and seventh embodiments of a cartridge as illustrated, can optionally function without relying on capillary action to draw the blood into the optical chambers of the cartridges. Also described is another system for hingedly connecting caps 50e and 50f to the bodies of cartridges 10e and 10f respectively, in which like the previous embodiments, a closed passage is provided for connecting the air bladder exit port to the sample storage well for communicating the pressurized air from the air bladder exit port to the sample storage well. When the air bladder is squeezed, metered blood is urged from the sample storage well, and the volume of blood urged is determined by the extent to which the air bladder is squeezed. Although the cartridges provide a combination of an optical chamber and a biosensor chamber, some embodiments comprise a cap hinged like 50e or 50f, and one of an optical chamber and a biosensor chamber comprising one or more biosensors.

Shown in FIG. 14A is an exploded top view of the disposable cartridge 10e, with cap 50e in an open configuration, for measuring a property of a sample, according to a fifth embodiment of the cartridge. The underside 52e of the cap 50e is shown as a flat surface having no recess, unlike cap 50b of cartridge 10b, which has a recess 55b (see FIGS. 5H, 8F and 8G). Instead of a recess in the cap, channel 55e in the cartridge body is used to facilitate formation of a closed passage for connecting the air bladder exit port 344e to the sample storage well 41e (see FIGS. 15G and 15H). Also, the gasket 57e is installed in the first housing member 20e (see FIGS. 15B and 15H), unlike gasket 57c, which is installed in the cap 50c of cartridge 10c (see FIGS. 10C and 10H). Another difference in cartridge 10e is the system used for hingedly connecting the cap 50e to the body of cartridge 10e.

Shown in FIG. 14B is a bottom view of the first housing member 20e of the cartridge shown in FIG. 14A. Shown in FIG. 14C is the bottom view of the first housing member 20e of the cartridge shown in FIG. 14B, overlaid by and in alignment with the gasket 100e shown in FIG. 14A. Shown in FIG. 14D is a top view of the second housing member 30e of the cartridge shown in FIG. 14A. Shown in FIG. 14E is the top view of the second housing member 30e shown in FIG. 14D, overlaid by and in alignment with the gasket 100e shown in FIG. 14A.

Figure 15H:
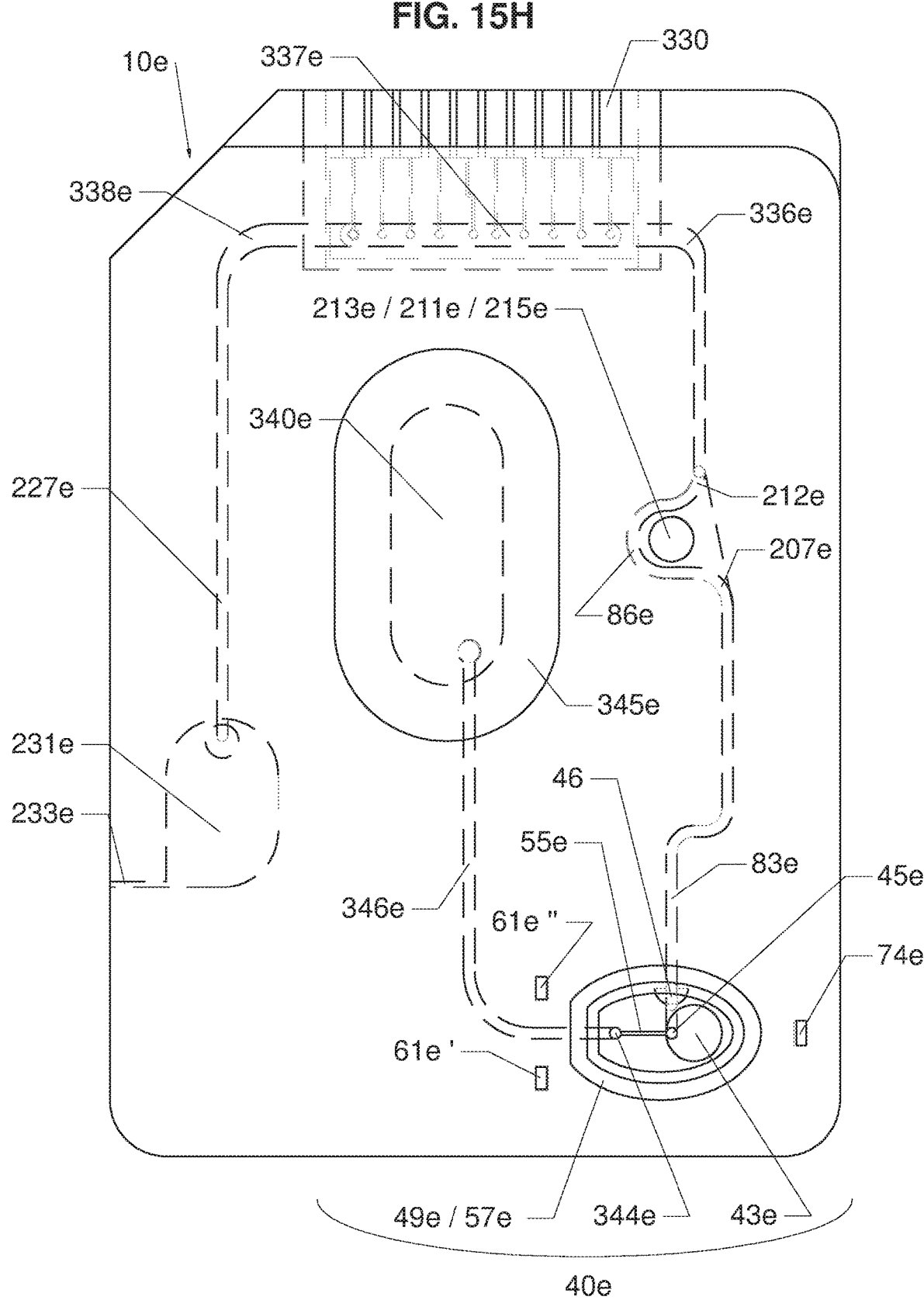
FIG. 15H is a top view of the cartridge 10e, with the cap hidden.

Shown in FIGS. 15A and 15B are perspective top views of the cartridge 10e in a closed and an open configuration, respectively, facilitated by hinges 60e' and 60e". Shown in FIG. 15C is a top view of the cartridge 10e in a closed configuration. Shown in FIG. 15D is a first cross-sectional view through the cartridge 10e shown in FIG. 15C along line D-D. Shown in FIG. 15E is a detailed view of detail E of the cartridge shown in FIG. 15D. Depending on the wetting ability (discussed previously in the context of contact angles, provided in Table 2) of the sample storage conduit 83e (FIGS. 15E and 15H), enlarge cavity 46 near the bottom opening 45e of sample storage well 41e of cartridge 10e provides an optional example of a means for mitigating, modifying or minimizing blood flow out of the sample storage well 41e, except when the air bladder 340e (see FIG. 15H) is squeezed. In other examples, an enlarged cavity may be disposed around either optical chamber entrance 207e or optical chamber exit 212e (see FIG. 15H). The enlarged cavity disposed at the optical chamber entrance may prevent blood from flowing into the optical chamber, except when the air bladder is squeezed. In some embodiments that have a sample storage conduit 83e with sufficient wetting ability, the enlarged cavity 46 may be disposed near the exit of the optical chamber 211e, and blood flow by capillary action is allowed to proceed into the optical chamber 211e and stop at the enlarged cavity, so that no blood enters the biosensor chamber 337e. In embodiments where the enlarged cavity is disposed near the exit of the optical chamber 211e (described in U.S. Pat. No. 9,470,673 and CA Pat. No. 2,978,737 to Samsoondar, which are incorporated herein by reference), the cartridges also comprise a biosensor chamber (e.g., 337e in FIG. 15H), and the cartridge optionally comprises biosensor calibration means (described in U.S. Pat. No. 9,470,673, CA Pat. No. 2,978,737 and U.S. Pat. No. 5,096,669, which are incorporated herein by reference). In embodiments having biosensor calibration means, blood is only allowed to enter the biosensor chamber 337e (see FIG. 15H) after the biosensors are calibrated, therefore the blood must be metered up to a safe distance from the biosensor chamber. Some embodiments may comprise an enlarge cavity (see 46 in FIG. 15E, for example) disposed at a point between the optical chamber exit 212e and the biosensor entrance 336e, depending on the location of the calibration fluid entry point, whereby the calibration fluid may come from a calibration fluid pouch installed in the cartridge as described in U.S. Pat. No. 9,470,673 and CA Pat. No. 2,978,737, or the calibration fluid may come from a fluid pack installed in the analyzer as described in U.S. Pat. No. 9,901,928 to Lin et al and described in greater detail later. The enlarged cavity 46 may be used to minimize, mitigate, or modify blood flow out of the sample storage well. Other know means for calibrating biosensors that require calibration, are considered to be within the scope of the present invention. If calibration fluid comes from a fluid pack installed in the analyzer, the cartridge may comprise an inlet port for receiving the calibration fluid, for example without any limitations, inlet ports described in U.S. Pat. No. 9,901,928 to Lin et al. Other non-limiting examples are provided below, in the description of cartridges 10k and 10m (See FIGS. 24A to 27K). After calibration of the biosensors, pressurized air from the air bladder 340e is used to regulate the flow of blood out of the optical chamber and into the biosensor chamber 337e, the blood displacing the calibration fluid in the biosensor chamber and forcing the calibration fluid out into the waste receptacle 231e (see FIG. 15H). Preferably, the blood must travel to a point between the biosensor chamber exit 338e of the biosensor chamber 337e and the vent 233e to ensure that all the sensors in the biosensor chamber 337e are covered with blood. Although calibration means are not illustrated in any of the cartridge embodiments 10e, 10f or 10g, optional calibration means are considered to be optional, and discussed in greater detail below. Requirement of biosensor calibration depends on the property of the blood sample measured, and the accuracy goal of the property measurement. Examples of blood properties are electrolytes, blood gases and pH measured in the biosensor chamber, and CO-oximetry and bilirubin measured in the optical chamber.

Shown in FIG. 15F is a cross-sectional view through the cartridge 10e shown in FIG. 15C along line F-F. Shown in FIG. 15G is a detailed view of detail G of the cartridge shown in FIG. 15F. Channel 55e in the cartridge body is used to facilitate formation of a closed passage for connecting the air bladder exit port 344e to the sample storage well 41e, instead of a cap recess, for example 55f in cap 50f in cartridge 10f (see FIG. 17G). A person having ordinary skill in the art should understand that a channel like 55e and a recess like 55f could perform the same function in combination or alone. A cap hinge 60e" and latch 75e are also shown in FIG. 15G. In cartridge 10e, two hinges (60e' and 60e") are shown by way of example only, and other hinged configurations may also be used as would be known to one of skill in the art. The latch 75e is designed to engage with cap latch catch 74e (see FIGS. 15B and 15H), in a snap-fit manner. In some cartridges, either the underside of the cap or a flat surface of the cartridge body surrounding the top portion of the sample storage well may comprise a magnet for closing the cap, instead of a cap latch 75e. In some cartridges, for example without limitations, a magnetic member shaped like gasket 57e (FIGS. 14A, 15G) or 57f (see FIG. 16A), may be attached to the underside of the cap, the flat surface of the cartridge body surrounding the top portion of the sample storage well, or a combination thereof, and either the cap or the flat surface of the cartridge body surrounding the top portion of the sample storage well may comprise a suitable metallic member for attracting the magnetic member. In some cartridges, the gasket and the magnetic member may be a single member, in that the single member performs the dual function of securing and sealing the cap against the flat surface of the cartridge body surrounding the top portion of the sample storage well, when the cartridge is in a closed configuration.

Shown in FIG. 15H is a top view of the cartridge 10e, with the cap removed for better viewing of structural details. For illustrative purposes, holes 61e' and 61e" are shown, and these holes are used to anchor hinges 60e' and 60e" for hingedly attaching cap 50e to the body of cartridge 10e. However, in some embodiments, cap 50e may be an integral part of the cartridge. Other known designs in the hinges and latching system are consider to be within the scope of the present invention.

Also shown in FIG. 15H is a blood shunt 86e for bypassing optical chamber 211e, and providing fluid connection between sample storage well 41e and biosensor conduit 337e. In this embodiment, by way of example, the depth of the optical chamber 211e is optionally equivalent to the thickness of gasket 100e. However, other optical chamber depths, a requirement that depends on the sample type and the property of the sample being measured, are considered to be within the scope of the present invention. The outline of the blood shunt 86e and the optical chamber 211e is defined as gasket cut-out 117e (see in FIG. 14A), positioned to align at least partly with at least one of optical windows 213e and 215e (located in first housing member 20e and second housing member 30e, respectively; see FIG. 15E). As an example, the thickness of the gasket 100e may be about 0.1 millimeter. Instead of forcing the blood through the shallow optical chamber 211e, defined by a cut out in the gasket 100e, to get to the biosensor chamber 337e, it is preferred to have a bypass route of larger cross-sectional area. Shown in FIG. 15E, viewed in conjunction with FIG. 15H, shunt 86e is illustrated, which allows the blood to circumvent the optical chamber 211e. This circumvention is preferred: 1) to mitigate lysis of the red blood cells (i.e., hemolysis) if the red blood cells are forced through a narrow opening like the opening defined the cross-section of the optical chamber 211e; and 2) to ensure that any obstruction in the optical chamber, for example due to clotting of blood, will not prevent the blood from flowing from the sample storage well 41e to the biosensor chamber 337e.

Shown in FIG. 16A is an exploded top view of the disposable cartridge 10f in an open configuration, for measuring one or more properties of a sample, according to a sixth embodiment of the cartridge. Shown in FIG. 16B is a bottom view of the first housing member 20f of the cartridge shown in FIG. 16A. Shown in FIG. 16C is the bottom view of the first housing member 20f of the cartridge shown in FIG. 16B, overlaid by and in alignment with the gasket 100f shown in FIG. 16A. Shown in FIG. 16D is a top view of the second housing member 30f of the cartridge shown in FIG. 16A. Shown in FIG. 16E is the top view of the second housing member 30f shown in FIG. 16D, overlaid by and in alignment with the gasket 100f shown in FIG. 16A. Shown in FIGS. 17A and 17B are perspective top views of the cartridge 10f in a closed and an open configuration respectively, facilitated by hinges 60f' and 60f", showing a cap recess 55f and a sealing gasket 57f in FIG. 17B. The cap recess 55f and the sealing gasket 57f are two differences between cartridges 10e and 10f.

Shown in FIG. 17C is a top view of the cartridge 10f in a closed configuration. Shown in FIG. 17D is a first cross-sectional view through the cartridge 10f shown in FIG. 17C along line D-D. Shown in FIG. 17E is a detailed view of detail E of the cartridge shown in FIG. 17D. Shown in FIG. 17F is a second cross-sectional view through the cartridge 10f shown in FIG. 17C along line F-F. Shown in FIG. 17G is a detailed view of detail G of the cartridge shown in FIG. 17F.

A third difference between cartridges 10e and 10f is that the sample storage well 41f is cylindrical in shape instead of the conical-like sample storage well 41e (see FIG. 15G). However, any shape of the sample storage well is considered to be within the scope of the present invention. A fourth difference is that the bottom opening (bottom portion) 45f of sample storage well 41f coincides with an entrance to the sample storage conduit 83f, with bottom opening 45f disposed at the bottom side of the storage well 41f (see FIG. 17G). An advantage of the cylindrical shape over a conical-like shape is an increased sample storage well sample storage capacity, for cartridges having the same thickness of the first housing members (20f and 20e). Although the top opening 43f of a sample storage well 41f is illustrated as circular, non-circular opening is optional. A larger top opening also provides additional sample storage well storage capacity. Another example of means for providing additional sample storage well sample storage capacity is illustrated in cartridges 10h-10m (FIGS. 20A-27H, 27J, 27K), in the form of a sample storage well boss 44 (44h, FIG. 20A; 44j, FIG. 22A; 44k, FIG. 24A). In POCT, small sample size is highly desirable, but a larger sample size is preferred for measurement of blood properties like blood gases, in particular partial pressure of oxygen ($pO_2$), for the following reason: since air contains 21% oxygen, the error in $pO_2$ measurement caused by inclusion of an air bubble in the sample is directly proportional to the size of the air bubble and inversely proportional to the sample size.

Another reason why a top opening, or top portion, of a sample storage well is preferred to be larger relative to the bottom opening is that it is easier to deposit a pin prick drop of blood accumulated on the skin of a body part, or blood from a syringe, into the sample well when the area of the top opening of the well is sufficiently large. Therefore, a preferred area of a sample well top opening (e.g. 43f, FIG. 17H) for any of the embodiments described herein, is in the range of about 10 $mm^2$ (square millimeters) to about 150 $mm^2$, or any amount there between, and a preferred area of a sample well bottom opening (e.g. 45f) for any of the embodiments described herein is in the range of about 0.01 $mm^2$ to about 10 $mm^2$, or any amount there between. A more preferable area of a sample well top opening (e.g. 43f) for any of the embodiments described herein is in the range of about 15 $mm^2$ to about 100 $mm^2$, or any amount there between, and a more preferable area of a sample well bottom opening (e.g. 45f) for any embodiment described herein is in the range of about 0.05 $mm^2$ to about 5 $mm^2$, or any amount there between.

Shown in FIG. 17H is a top view of the cartridge 10f, with the cap removed. Another means for mitigating, modifying or minimizing blood flow out of the sample storage well is to make all or part of the sample storage conduit less wettable. Alternatively, as illustrated in FIG. 17H, a hydrophobic insert 82 disposed near the entrance of sample storage conduit 83f and aligned with the sample storage conduit 83f, provides means for minimizing blood flow out of the sample storage well, except when either the air bladder is squeezed, or negative pressure is applied to the leading edge of the blood sample (discussed in more detail regarding cartridges 10j, 10k and 10m; FIGS. 20A-27H, 27J, 27K, below). The term hydrophobic insert used to describe element 82 implies that the hydrophobicity of the duct in element 82 aligned with the sample storage conduit 83f, is more hydrophobic than the sample storage conduit 83f. In addition to an enlarged cavity (see 46 in FIG. 15E, for example) and a hydrophobic insert (see 82 in FIG. 17H, for example), other structural features that provide means for minimizing blood flow out of the sample storage well except when either positive pressure is applied to the surface of the blood sample in the sample storage well, or negative pressure is applied to the leading edge of the blood sample, include: a sample storage well insert having internal walls more wettable than the sample storage conduit; a sample storage well having internal walls more wettable than the sample storage conduit; a sample storage conduit less wettable than the internal walls of the sample storage well; and any combination thereof. Therefore, depending on the plastic used to manufacture the cartridge, hydrophobic insert 82 in cartridge 10f and the enlarged cavity 46 in cartridge 10e are optional. Also, the stringency of the requirement to mitigate blood flow from the sample storage well (e.g. 41f) into the sample storage conduit (e.g. 83f) depends on the property of the blood measured. For example, a blood property measurement that requires a fixed amount a reagent (e.g., PT-INR) has a more stringent requirement to mitigate blood flow from the sample storage well (e.g. 41f) into the sample storage conduit (e.g. 83f) than a property that does not require a reagent (e.g., CO-oximetry and bilirubin). In other words, the metering requirement for PT-INR is more stringent than the metering requirement for CO-oximetry or bilirubin.

Figure 18A:
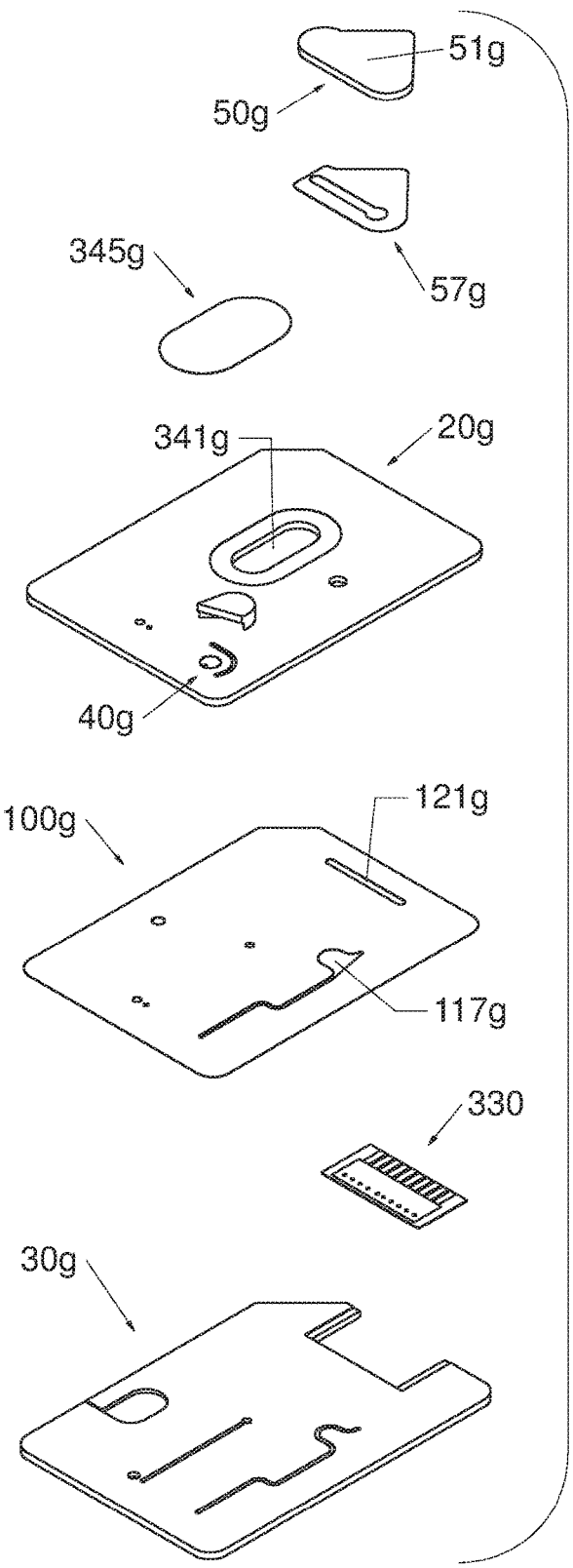
FIG. 18A is an exploded top view of the disposable cartridge 10g in an open configuration, for measuring a property of a sample, according to a seventh embodiment of the cartridge.

Shown in FIG. 18A is an exploded top view of the disposable cartridge 10g in an open configuration, for measuring one or more properties of a sample, according to a seventh embodiment of the cartridge. Cartridge 10g comprises both an optical chamber 211g (see FIG. 19E) and a biosensor chamber 337g (see FIG. 19H). An additional feature of cartridge 10g is the ability to accommodate larger fingers and a baby's heel, when these body parts are used to provide the blood sample. Also, the top opening 43g of the sample storage well 41g can be made relatively large, making the sample storage well 41g more accessible for delivery of a pin prick drop of blood, or delivery of blood from a syringe.

Figure 18B:
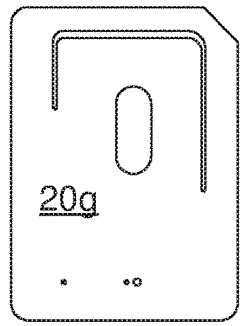
FIG. 18B is a bottom view of the first housing member 20g of the cartridge shown in FIG. 18A.
Figure 18C:
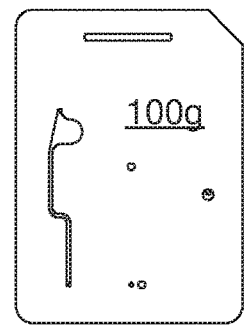
FIG. 18C is the bottom view of the first housing member 20g of the cartridge shown in FIG. 18B, overlaid by and in alignment with the gasket 100g shown in FIG. 18A.
Figure 18D:
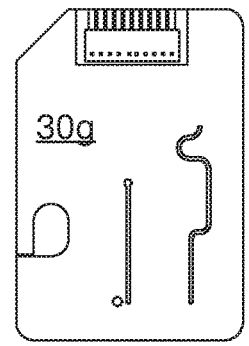
FIG. 18D is a top view of the second housing member 30g of the cartridge shown in FIG. 18A.
Figure 18E:
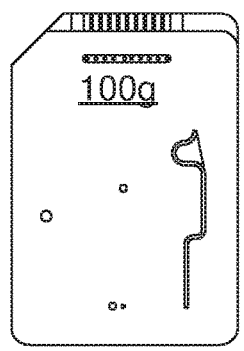
FIG. 18E is the top view of the second housing member 30g shown in FIG. 18D, overlaid by and in alignment with the gasket 100g shown in FIG. 18A.

Shown in FIG. 18B is a bottom view of the first housing member 20g of the cartridge shown in FIG. 18A. Shown in FIG. 18C is the bottom view of the first housing member 20g of the cartridge shown in FIG. 18B, overlaid by and in alignment with the gasket 100g shown in FIG. 18A. Shown in FIG. 18D is a top view of the second housing member 30g of the cartridge shown in FIG. 18A. Shown in FIG. 18E is the top view of the second housing member 30g shown in FIG. 18D, overlaid by and in alignment with the gasket 100g shown in FIG. 18A.

Figure 19H:
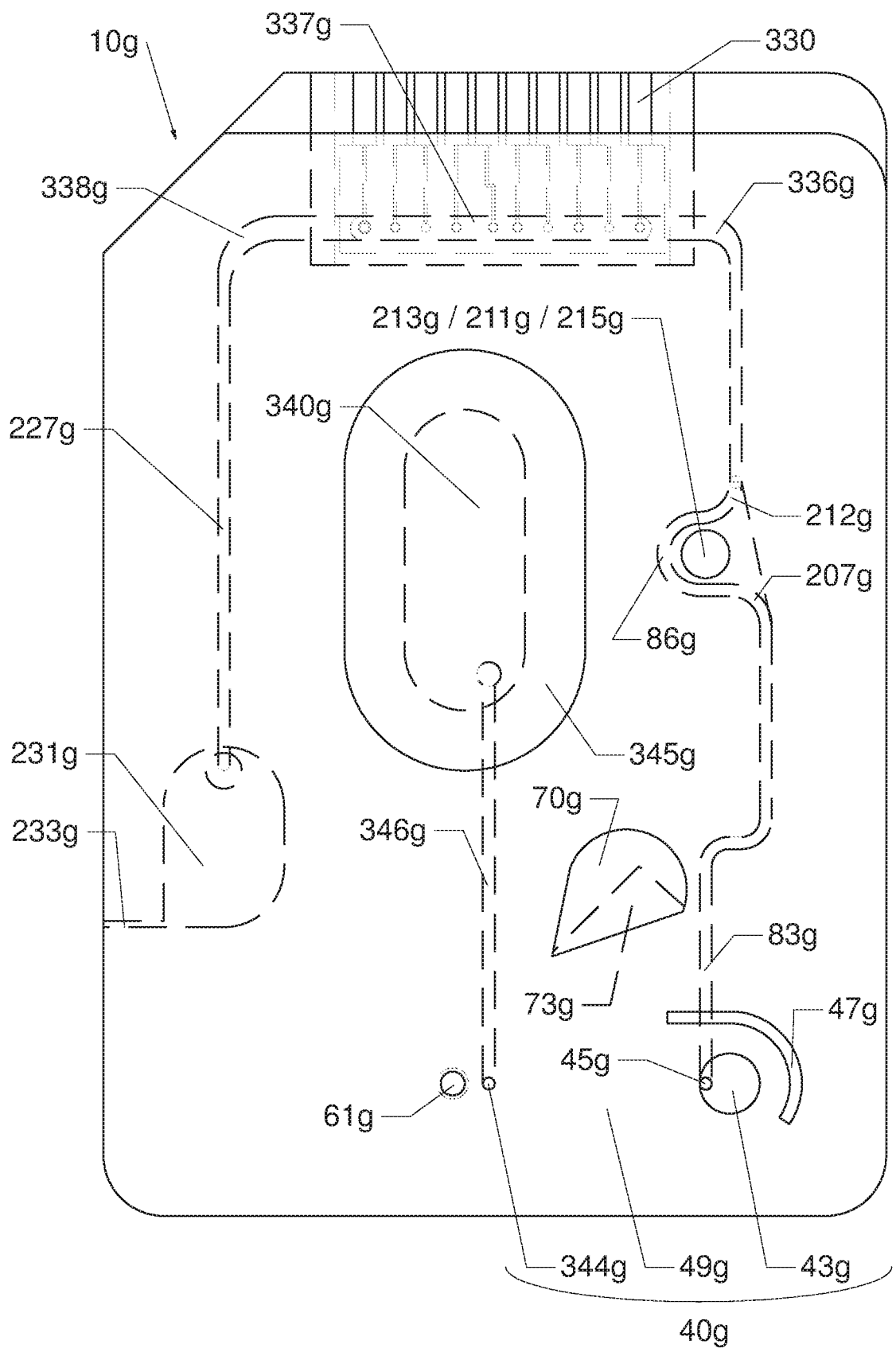
FIG. 19H is a top view of the cartridge 10g, with the cap hidden.

Shown in FIG. 19A is a perspective top view of the cartridge 10g in a closed configuration. Shown in FIG. 19B is a perspective top view of the cartridge 10g in an open configuration. Shown in FIG. 19C is a top view of the cartridge 10g in a closed configuration. Shown in FIG. 19D is a first cross-sectional view through the cartridge 10g shown in FIG. 19C along line D-D. Shown in FIG. 19E is a detailed view of detail E of the cartridge shown in FIG. 19D. Shown in FIG. 19F is a second cross-sectional view through the cartridge 10g shown in FIG. 19C along line F-F. Shown in FIG. 19G is a detailed view of detail G of the cartridge shown in FIG. 19F. Shown in FIG. 19H is a top view of the cartridge 10g, with the cap removed.

A person having ordinary skill in the art should appreciate that although cartridges 10e, 10f and 10g are describe having both an optical chamber and a biosensor chamber, a cartridge may comprise either one or more optical chambers, or one or more biosensor chambers; it should also be appreciated that an optical chamber and a biosensor chamber are non-limiting examples of detection chambers, and although blood is used in many cases as an example of the sample when describing the cartridges, the cartridges are not limited to measuring properties of a blood sample.

Overview of Cartridge 10h as a Non-Limiting Example

Cartridge 10h (see FIGS. 20A-21H) is an eighth embodiment of a cartridge for measuring one or more properties of a blood sample, comprising an optical chamber and a biosensor chamber, but other similar embodiments may not include a biosensor chamber. In the similar embodiments that do not include a biosensor chamber, the optical chamber 211h may be operatively connected to the vent 233h with no detection chamber in between, as for example, cartridge 10 illustrated in FIG. 2A, where the optical chamber 211 is connected to the vent 233, with no detection chamber in between. Also, other similar embodiments, as for example for cartridge 10j described later (see FIGS. 22A-23G), illustrate pre-calibrated biosensors, and consequently there is no need for calibration fluid.

A first difference in cartridge 10h compared with the previous cartridge embodiments 10 to 10f, is a sample storage well boss 44h disposed at the top portion of the sample storage well 41h well for increasing the sample storage well sample storage capacity, without necessarily increasing the overall thickness of the sample inlet portion 40h and a cap 50h in a closed configuration; the recess 55h provides the space for housing the boss 44h, provided that the boss 44h and cap recess 55h do not make contact so as to seal off the top opening 43h of the sample storage well 41h. A second difference is the illustration of elements used for calibrating the biosensors in biosensor array 330. In particular, cartridge 10h comprises a calibration fluid pouch 355h. A third difference is the optional inclusion of a directional valve, which operates automatically: movement of the elastomeric flap 371 is regulated by movement of the calibration fluid and the blood. In contrast, movement of the elements of directional valves used in cartridges 10k and 10m, discussed later, require participation by the analyzer.

Cartridge 10h also comprises an optional enlarged cavity 46h, which may be used to insert an air bubble between the calibration fluid and the blood to prevent mixing of the calibration fluid and the blood and to assist in removing residual calibration fluid from the biosensor chamber, before the blood flows into the biosensor chamber. It is known by those skilled in the art that an air bubble is effective for removing fluid from a surface. The enlarged cavity 46h may also function to buffer excess blood volume and consequently restrict blood flow up to the enlarged cavity 46h.

After the blood sample in the sample storage well 41h is urged to flow, a blood flow path is established. The blood flow path comprises an inlet blood flow path and a terminal blood flow path, illustrating that the blood makes two separate stops. The inlet blood flow path begins at the sample storage well 41h and ends at a point between the optical chamber overflow conduit 227h and the junction 367h; the terminal blood flow path begins at the end of the inlet blood flow path, i.e. at a point between the optical chamber overflow conduit 227h and the junction 367h, and ends at a point between the biosensor chamber exit 338h and the vent 233h (see FIGS. 21D and 21H). The term leading edge of the blood sample refers to the front portion of the blood in the blood flow path, the term downstream of a structure refers to a location between the structure and the vent 233h or a cartridge exit duct (for example 390j illustrated in FIGS. 23D and 23E) in cartridges that do not have vents like 233h. The term upstream of a structure refers to a location between the structure and the sample storage well 41h. The junction 367h is located between the optical chamber 211h and the biosensor chamber 337h where a calibration fluid flow path (described next) intersects with the blood flow path. In order for the blood to flow from the sample storage well 41h to the optical chamber overflow conduit 227h, the blood may flow through the optical chamber 211h through the shunt 86h or any similar structure surrounding the optical chamber 211h, or a combination thereof. Therefore, the term "blood flowing out of the optical chamber" may imply blood flowing through the optical chamber and/or any shunt-like structure.

After the calibration fluid pouch 355*h* is ruptured by applying force to the top of pouch 355*h*, pushing the pouch against a spike 361*h* (see FIG. 21H in conjunction second housing member 30*h* shown in FIG. 20A), a calibration fluid flow path is established. The calibration fluid flow path begins at the calibration fluid pouch 355*h* and terminates at a point between the biosensor chamber exit 338*h* and the vent 233*h*, via the junction 367*h*. The term leading edge of the calibration fluid refers to the front portion of the calibration fluid in the calibration fluid flow path. Since both the calibration fluid and the blood must pass through the biosensor chamber 337*h*, the blood flow path and the calibration fluid flow path share a common path. The common path begins at the junction 367*h* and terminates at a point between the biosensor chamber exit 338*h* and the vent 233*h* or cartridge exit duct (for example 390*j* illustrated in FIGS. 23D and 23E) in cartridges that do not have vents like 233*h*.

Shown in FIG. 20A is an exploded top view of the disposable cartridge 10*h* in a closed configuration. Shown in FIG. 20B is a bottom view of the first housing member 20*h* of the cartridge shown in FIG. 20A. Shown in FIG. 20C is the bottom view of the first housing member 20*h* of the cartridge shown in FIG. 20B, overlaid by and in alignment with the gasket 100*h* shown in FIG. 20A. Shown in FIG. 20D is a top view of the second housing member 30*h* of the cartridge shown in FIG. 20A, showing a cavity 372 for anchoring elastomeric flap 371, and a duct 365*h* for channeling calibration fluid from duct 364*h* to biosensor chamber 337*h* via junction 367*h* (see FIG. 21H). Shown in FIG. 20E is the top view of the second housing member 30*h* shown in FIG. 20D, overlaid by and in alignment with the gasket 100*h* shown in FIG. 20A, with the biosensor array 330 installed. Shown in FIG. 20F is a detailed view of detail F of the cartridge shown in FIG. 20E. In this non-limiting example, the directional valve comprises an elastomeric flap 371 (having a larger section 371" and a smaller section 371') for maintaining the blood and calibration fluid in their respective compartments upstream (i.e., towards the sample, storage, well 41*h*) of the flap. The larger section 371" is anchored in cavity 372, and the smaller section 371" is flappable wherein a first position, elastomeric flap 371 closes off the blood passage when calibration fluid is being delivered to the biosensors, and when in a second position, elastomeric flap 371 closes off the calibration fluid passage when blood is being delivered to the biosensor chamber. Elastomeric flap 371 is therefore resilient and movable from the first position to the second position depending upon which fluid is passing through the flow passageways.

Shown in FIG. 21A is a perspective top view of the cartridge 10*h* in a closed configuration. Shown in FIG. 21B is a perspective bottom view of the cartridge 10*h*, illustrating a recess 375*h* in bottom of second housing member 30*h* of cartridge 10*h* for heating the blood with heating pad installed in analyzer receptor. The recess allows the blood in the hairpin loop segment of sample storage conduit 83*h* to be closer to the heating element. Also shown is a laminate 368*h* for covering calibration fluid duct 364*h* and hole 363*h* in spike 361*h* (see FIGS. 21E and 21H). Shown in FIG. 21C is a perspective top view of the cartridge 10*h* in an open configuration, showing elements of the cap 50*h*, a vent 233*h*, and a calibration fluid pouch 355*h*. In this embodiment, the cap rotates vertically about the hinges 60*h*' and 60*h*", in a plane substantially orthogonal to a plane generally defined by a flat surface surrounding the hinges. A paper label may be used to cover the calibration fluid pouch 355*h*. The paper label may comprise circular perforations for facilitating tearing the label during activation of an analyzer plunger, used to press the pouch 355*h* against the spike 361*h*, in order to rupture the pouch 355*h*. The analyzer plunger may be activated by, for example, a stepper motor or a solenoid.

Shown in FIG. 21D is a top view of the cartridge 10*h* in a closed configuration, showing an enlarge cavity 46*h*, which may be used to create an air bubble between the calibration fluid delivered by the pouch 355*h*, and the leading edge of the blood sample. Regulation of blood flow in cartridge 10*h* uses positive pressure provided by squeezing or activating air bladder 340*h*. In contrast, regulation of blood flow in cartridge 10*j* (discussed later) uses negative pressure, provided by a vacuum pump installed in an analyzer. Shown in FIG. 21E is a first enlarged cross-sectional view through the cartridge 10*h* shown in FIG. 21D along line E-E, showing the elastomeric flap 371, portions (46*h*' and 46*h*") of the enlarged cavity 46*h*, the optical chamber 211*h*, first optical window 213*h*, second optical window 215*h*, and the blood shunt 86*h*. Shown in FIG. 21F is a second enlarged cross-sectional view through the cartridge 10*h* shown in FIG. 21D along line F-F, showing the biosensor chamber exit 338*h*, air bladder duct 343H, an air bladder 340*h*, a sample storage conduit 83*h*, and a detection chamber overflow conduit 228*h*. Shown in FIG. 21G is a third enlarged cross-sectional view through the cartridge 10*h* shown in FIG. 21D along line G-G, illustrating the cap 50*h*, the sample storage well 41*h* surrounded by a boss 44*h*. Also shown is the bottom opening (or bottom portion) 45*h* of sample storage well 41*h*, which coincides with the entrance of the sample storage conduit 83*h*, and a hydrophobic insert 82*h* disposed near the entrance of sample storage conduit 83*h* for providing means for regulating blood flow out of the sample storage well. Also shown is the detection chamber overflow conduit 228*h*, which may also serve as a waste receptacle for receiving excess fluid, for example, calibration fluid and blood. Shown in FIG. 21H is a fourth enlarged cross-sectional view through the cartridge 10*h* shown in FIG. 21D along line H-H. Shown is the calibration fluid pouch 355*h*, resting on a compressible member 357*h* that encircles a spike 361*h* that is used to rupture the pouch 355*h*. Shown in the spike 361*h* (spike 361*h* is also shown in second housing member 30*h* in FIG. 20A) is a hole 363*h* for draining calibration fluid from the pouch 355*h* after the pouch is ruptured, and ducts 364*h* and 365*h* for channeling the calibration fluid to the biosensor chamber entrance 336*h*, and subsequently to the biosensor chamber 337*h*. The duct 365*h* and the biosensor chamber entrance 336*h* intersect at a junction 367*h*. Also shown is a laminate 368*h* for covering calibration fluid duct 364*h* and hole 363*h* in spike 361*h*, a cross section of the smaller section 371' of elastomeric flap 371, an air bladder 340*h*, and a detection chamber overflow conduit 228*h*.

The calibration fluid flow path in cartridge 10*h* is defined with respect to the cartridge, whereas the calibration fluid flow path in cartridges 10*k* and 10*m* for example, may be defined as: 1) with respect to the cartridge; and 2) with respect to a system comprising the cartridge and an analyzer used to operate the cartridge. With respect to the cartridge, referring to cartridge 10*h*, the calibration fluid flow path begins at the pouch 355*h*, and the fluid from the ruptured pouch flows down through the hole 363*h* in the spike 361*h*, across the duct 364*h*, then up the duct 365*h* and terminates at a point between the biosensor chamber exit 338*h* and the vent 233*h* (see FIGS. 21D and 21H). In cartridges 10*k* and 10*m* (described in more detail later), the calibration fluid is delivered from a pouch in an analyzer, and therefore with respect to the cartridge, the calibration fluid flow path begins where the external calibration fluid is delivered to the cartridge (see 393*k* in FIG. 25A and 393*m* in FIG. 27A), and ends at a point between the biosensor chamber exit 338*k*/338*m* and the cartridge exit duct 390*k*/390*m*; with respect to the system, which includes the cartridge and the analyzer used in conjunction with the cartridge (10*k* and 10*m*), the calibration fluid flow path begins at the external calibration fluid pouch located in the analyzer (also referred to as, analyzer calibration fluid pouch), and ends at a point between the biosensor chamber exit 338*k*/338*m* and the cartridge exit duct 390*k*/390*m*.

Overview of Cartridge 10*j* as a Non-Limiting Example

Cartridge 10*j* (see FIGS. 22A-23G) is a ninth embodiment of a cartridge for measuring one or more properties of a blood sample, comprising an optical chamber and a biosensor chamber, but other similar embodiments do not include a biosensor chamber. In the similar embodiments that do not include a biosensor chamber, the optical chamber 211*j* may be operatively connected to the cartridge exit duct 390*j* with no other detection chamber in between, as for example, cartridge 10 illustrated in FIG. 2A, where the optical chamber 211 is connected to the vent 233, with no detection chamber in between. In cartridge 10*j*, negative pressure provided by a vacuum pump housed in a cartridge analyzer is used instead of positive pressure, to regulate blood flow: the positive pressure in the previous cartridge embodiments is provided by squeezing or activating an air bladder in the cartridge.

After the blood in the sample storage well 41*j* is urged to flow, a blood flow path is established, beginning at the sample storage well 41*j* and ending at a point between the biosensor chamber exit 338*j* and the cartridge exit duct 390*j*. Since the biosensors are pre-calibrated, unlike the biosensors in cartridge 10*h*, it is preferred that after the blood is pulled from the sample storage well 41*h*, the leading edge of the blood makes a single stop at a point between a biosensor chamber exit 338*j* and the cartridge exit duct 390*j*, and therefore may provide more time to hydrate the biosensors prior to measuring an electric signal.

A first difference in cartridge 10*j* compared with cartridge 10*h* (illustrated in FIGS. 20A-21H) is that cartridge 10*j* does not have a calibration fluid flow path because the biosensors are pre-calibrated. A second difference in cartridge 10*j* compared with cartridge 10*h* is the absence of an air bladder; instead of applying positive pressure to the surface of the blood sample in the sample storage well 41*j* in order to push the leading edge of the blood sample into the detection chamber, negative pressure is applied via the cartridge exit duct 390*j* to pull the leading edge of the blood sample into the detection chamber. Cartridge 10*j* comprises a cartridge exit duct 390*j* for receiving a vacuum hollow needle. The vacuum hollow needle comprises a first end operatively connected to the analyzer vacuum pump, an open end distal to the first end and operatively connected to the first end, and an outer surface. The duct 390*j* comprises a vacuum sealing member 353*j* for frictionally engaging the outer surface of the vacuum hollow needle, whereby negative pressure generated by the vacuum pump is transferable to the cartridge (see FIGS. 23D and 23E) via the cartridge exit 339*j*. The cartridge exit 339*j* is an inner portion of the duct 390*j* in cartridge 10*j*, in operative communication with the vacuum pump via the vacuum hollow needle. The vacuum hollow needle may be either permanently extended from the vacuum pump, or retracted and only extended to engage with the vacuum sealing member 353*j* after the cartridge is fully inserted into the cartridge receptor of the analyzer. If the vacuum hollow needle is permanently extended from the vacuum pump, the vacuum hollow needle becomes inserted into the cartridge via the vacuum sealing member 353*j*, when the cartridge is inserted in the cartridge receptor of the analyzer.

The disposable cartridge 10*j* is adjustable between an open configuration and a closed configuration, by rotating the cap 50*j* about the hinge 60*j*. In the open configuration the sample storage well 41*j* is configured to receive the blood sample, and in the closed configuration, the blood in the sample storage well is subjected to atmospheric pressure via a cap breathable plug 56*j*, for enabling the vacuum generated by the vacuum pump to be applied to the cartridge. Examples of a vacuum pump associated with the analyzer, are without any limitations, a diaphragm, a plunger, or a peristaltic vacuum pump. A person having ordinary skill in the art should appreciate that other means may be used for subjecting the blood in the sample storage well 41*j* to atmospheric pressure, for example without any limitations, a hole in the cap, or a leaky seal between the cartridge body upper surface and the cap when the cap is closed. For simplicity, the aforementioned means for subjecting the blood in the sample storage well 41*j* to atmospheric pressure when the cap is closed, may be described as a cap vent.

A third difference when compared with cartridge 10*h* is that cartridge 10*j* does not have a vent like vent 233*h* regarding cartridge 10*h*. Instead, the cap 50*j* comprises a cap breathable plug 56*j* for subjecting the blood in the sample storage well 41*j* to atmospheric pressure, and a cartridge exit duct 390*j* for applying negative pressure to the leading edge of the blood. The cap breathable plug is advantageous in preventing spillage of blood sample, which could contaminate the outside of the cartridge and the analyzer. A cap breathable plug may be in the form of a thin membrane, which allows air flow but not liquid like blood and water. Although the cap breathable plug is shown as a circular disc, the plug may have any shape or any size. Cartridge 10*j* also comprises another similar breathable plug, an exit breathable plug 356*j*, for preventing liquid from leaving the cartridge and entering the vacuum pump via the vacuum hollow needle.

A fourth difference in cartridge 10*j* compared with cartridge 10*h* is the absence of a hydrophobic insert 82*h* (see FIGS. 20A and 21G) and instead, cartridge 10*j* comprises a sample storage well insert 441*j* (see FIGS. 22A and 23G). When the sample storage well inserted 441*j* is inserted in the cartridge body via a hole 443*j* (see FIG. 22A), the sample storage well appears just like the sample storage well 41*h* of cartridge 10*h* (compare FIGS. 21G and 23G). Sample storage well insert 441*j* may be made in its entirety of hydrophilic material, or the one or more walls in the insert 441*j* that is exposed to the blood sample is treated so that the one or more walls become hydrophilic. By hydrophilic, it is implied that the hydrophilicity of the walls of the sample storage well is sufficiently greater than the hydrophilicity of the sample storage conduit 83*j*. Some cartridge embodiments may comprise both a hydrophilic sample storage well insert similar to 441*j* and a hydrophobic insert similar to 82*h*. The hydrophilicity of the sample storage well insert enhances wetting the surface of the well with the blood sample, thereby mitigating inclusion of air bubbles in the well, and enhances retention of at least a portion of the blood sample in the sample storage well. The degree of sample retention in the sample well increases as the walls of the sample storage well 41*j* are made more hydrophilic and the sample storage conduit 83*j* is made less hydrophilic. Negative pressure applied to either the bottom opening 45*j* of the sample storage well, or to the leading edge of the blood sample (i.e. if the blood moves past the bottom opening 45*j*), may be used to overcome the forces that cause the blood sample to be retained in the sample storage well. A combination of sufficiently hydrophobic sample storage well surface and sufficiently hydrophilic sample storage conduit is preferred, whereby sample flow past the bottom opening 45j of the sample storage well is minimized. Similarly, positive pressure applied to the surface of the blood sample in the sample storage well, if a cartridge like 10h comprises an insert like 441j, may be used to overcome the forces that cause the blood sample to be retained in the sample storage well 41h.

The entire cartridge less the insert 441j may be manufactured from hydrophobic material, which may be preferred for facilitating injection molding and providing suitable plastic clarity for the optical windows 213j and 215j. As previously explained, enlarge cavity 46 near the bottom opening 45e of sample storage well 41e of cartridge 10e provides an optional example of a means for mitigating, modifying or minimizing blood flow out of the sample storage well 41e (see FIGS. 15E, 15G and 15H). Therefore, cartridge 10j may also comprise an enlarged cavity like 46.

A fifth difference between cartridge 10j and 10h is that cartridge 10j comprises an enlarged waste receptacle 231j. A person having ordinary skill in the art should understand that the waste receptacle may have various shapes including looped structures like the sample storage conduit 83j.

Shown in FIG. 22A is an exploded top view of the disposable cartridge 10j in a closed configuration. Shown in FIG. 22B is a bottom view of the first housing member 20j of the cartridge shown in FIG. 22A, showing the sample storage well insert 441j inserted from the bottom of the first housing member 20j (view in conjunction with FIG. 23G), as an example of a way to install the insert 441j. Shown in FIG. 22C is the bottom view of the first housing member 20j of the cartridge shown in FIG. 22B, overlaid by and in alignment with the gasket 100j shown in FIG. 22A, showing the insert 441j mostly covered by the gasket 100j. Shown in FIG. 22D is a top view of the second housing member 30j of the cartridge shown in FIG. 22A. Shown in FIG. 22E is the top view of the second housing member 30j shown in FIG. 22D, overlaid by and in alignment with the gasket 100j shown in FIG. 22A.

Shown in FIG. 23A is a perspective top view of the cartridge 10j in a closed (but not sealed) configuration. Shown in FIG. 23B is a perspective bottom view of the cartridge 10j, showing a recess 375j in bottom of second housing member 30j of cartridge 10j for heating blood in the sample storage conduit 83j, using one or more heating pads installed in the cartridge receptor of an analyzer. Shown in FIG. 23C is a perspective top view of the cartridge 10j in an open configuration for receiving a blood sample, showing elements of the cap 50j, and the sample storage well boss 44j.

Shown in FIG. 23D is a top view of the cartridge 10j in a closed configuration. In the closed configuration, the cap and cartridge are not in a sealed configuration because the cap 50j comprises a cap breathable plug 56j, which subjects the blood sample to atmospheric pressure. Shown in FIG. 23E is a first enlarged cross-sectional view through the cartridge 10j shown in FIG. 23D along line E-E, showing the vacuum sealing member 353j installed in the cartridge exit duct 390j, and showing the cartridge exit 339j. The cartridge exit duct 390j receives the analyzer vacuum hollow needle, and the vacuum sealing member 353j frictionally engages the outer surface of the vacuum hollow needle. In operation, the vacuum hollow needle slides into the vacuum sealing member 353j after the cartridge is inserted into the receptor of an analyzer, for transferring negative pressure to the cartridge exit 339j. The negative pressure may be applied to the leading edge of the blood in order to establish a blood flow path. Also shown is an exit breathable plug 356j, for preventing liquids from leaving the cartridge and entering the vacuum pump via the vacuum hollow needle. Shown in FIG. 23F is a second enlarged cross-sectional view through the cartridge 10j shown in FIG. 23D along line F-F, showing an optical chamber 211j, a first optical window 213j, a second optical window 215j, and a blood shunt 86j for allowing blood to bypass the optical chamber 211j, providing an alternative blood flow path between sample storage well 41j and biosensor conduit 337j, instead of a path through the optical chamber 211j. Shown in FIG. 23G is a third enlarged cross-sectional view through the cartridge 10j shown in FIG. 23D along line G-G, showing the association between the cap 50j and the sample storage well 41j when the cartridge is in a closed configuration. Also shown in FIG. 23G is a hinge 60j", a cap latch 75j, a sectional view of the sample storage well insert 441j, and the bottom portion 45j of the sample storage well 41j. The bottom portion 45j coincides with the entrance to the sample storage conduit 83j. In FIG. 1J, regarding cartridge 10, elements 45 and 81 are optionally shown separately because the cartridge examples provided comprise a first housing member 20 and second housing member 30, and the elements 45 and 81 are disposed in the first housing member 20 and second housing member 30 respectively. The cartridge embodiments provided are non-limiting examples and a person having ordinary skill in the art should appreciate that the cartridges can comprise any number of housing members, any combination of different types of materials with respect wettability and optical properties for example, and strategically located physical features. Some examples of physical features include enlarged cavities and inserts made from materials having different wettability properties, and may be included in cartridge 10j.

Overview of Cartridge 10k as a Non-Limiting Example

Cartridge 10k (see FIGS. 24A-26E) is a tenth embodiment of a cartridge for measuring one or more properties of a blood sample, comprising an optical chamber and a biosensor chamber, but other similar embodiments do not include a biosensor chamber. In the similar embodiments that do not include a biosensor chamber, the optical chamber 211k may be operatively connected to the cartridge exit duct 390k with no other detection chamber in between. For cartridge 10k, as for cartridge 10j, negative pressure is used instead of positive pressure, to regulate blood flow.

A difference in cartridge 10k when compared with cartridge 10j (see FIGS. 22A-23G) is the inclusion of means for calibrating the biosensors 330. The means comprise external calibration fluid provided by an analyzer calibration fluid pouch. In contrast, cartridge 10h illustrated in FIGS. 20A-21H comprises internal calibration fluid, provided by a cartridge calibration fluid pouch 355h.

After a portion of the blood sample in the sample storage well 41k is urged to flow, a blood flow path is established, the blood flow path comprising an inlet blood flow path and a terminal blood flow path. The inlet blood flow path begins at the sample storage well 41k and ends at a point between the optical chamber overflow conduit 227k and the junction 387k; the terminal blood flow path begins at the end of the inlet blood flow path, i.e. at a point between the optical chamber overflow conduit 227k and the junction 387k, and ends at a point between the biosensor chamber exit 338k and the cartridge exit duct 390k. The term leading edge of the blood sample refers to the front portion of the blood in the blood flow path, the term downstream of a structure refers to a location between the structure and the cartridge exit duct 390$k$, and the term upstream of a structure refers to a location between the structure and the sample storage well 41$k$. The leading edge of the blood makes a first stop at a point between the optical chamber overflow conduit 227$k$ and a junction 387$k$ (see FIG. 24D), defining the inlet flow path; later the blood makes a second stop at a point between the biosensor chamber exit 338$k$ and a cartridge exit duct 390$k$ (see FIG. 25A), defining the terminal blood flow path. For clarity, the first stop and the second stop of the leading edge of the blood sample, clears the optical chamber 211$k$ and the biosensor chamber 337$k$ respectively. The junction 387$k$ is located between the optical chamber 211$k$ and the biosensor chamber 337$k$ where a calibration fluid flow path intersects with the blood flow path. With respect to the cartridge, the calibration fluid flow path begins where the external calibration fluid is delivered to the cartridge, i.e. at the internal segment of the calibration duct 393$k$ (see FIGS. 25A and 25D), and terminates at a point between the detection chamber exit 338$k$ and the cartridge exit duct 390$k$. With respect to a system that includes the cartridge and an analyzer used in conjunction with the cartridge, the calibration fluid flow path begins at the analyzer calibration fluid pouch and terminates at a point between the biosensor chamber exit 338$k$ and the cartridge exit duct 390$k$.

The analyzer calibration fluid pouch may comprise a collapsible wall and an analyzer calibration fluid dispenser or needle or dispensing needle. The dispenser typically comprises a first end in operative communication with the pouch, an open end distal to the first end for dispensing calibration fluid, and an outer surface for sliding the dispenser into the cartridge calibration duct 391$k$, facilitated by a calibration sealing member 354$k$. The dispenser can transfer the calibration fluid from the analyzer calibration fluid pouch to the internal segment 393$k$ of the calibration duct 391$k$. The analyzer calibration fluid pouch wall is able to collapse when fluid is dispensed, thereby mitigating suck back into the pouch. The analyzer calibration fluid dispensing needle may be either permanently extended from the collapsible pouch, or retracted and only extended to engage with the calibration sealing member 354$k$ of the cartridge after the cartridge is inserted into the analyzer receptor. If the analyzer calibration fluid dispensing needle is permanently extended from the pouch, the analyzer calibration fluid dispensing needle becomes inserted into the cartridge via the calibration sealing member 354$k$, when the cartridge is inserted in the analyzer receptor. Simultaneously, the vacuum hollow needle is inserted into the cartridge exit duct 390$k$.

Another difference in cartridge 10$k$ when compared with cartridge 10$h$ is the directional valve 376$k$ (FIG. 24A; described below). Cartridge 10$h$ comprises an elastomeric flap (see 371 in FIG. 20D) directional valve, and cartridge 10$k$ comprises a ball type directional valve. A person having ordinary skill in the art should understand that the directional valves illustrated are examples only, and should not limit the present invention in any way. Other examples of directional valve elements are elements in the form of rods that move up and down along the longitudinal axis of the rod, having strategically placed O-rings. Some directional valve elements comprise rods that rotate about the longitudinal axis instead of moving up and down. For elements of directional valves that rotate, which may also include balls like 377$k$, the elements may comprise external portions like the head of a screw, and the analyzer may comprise stepper motors having projections like the end of a screwdriver for engaging the external portions of the directional valve elements that appears like the head of a screw: rotational motion is transferred from the stepper motor to the directional valve element.

Shown in FIG. 24A is an exploded top view of the disposable cartridge 10$k$ in an open configuration. Shown in FIG. 24$b$ is a bottom view of the first housing member 20$k$ of the cartridge shown in FIG. 24A. Shown in FIG. 24C is a bottom view of the second housing member 30$k$ of the cartridge shown in FIG. 24A, showing a sample duct 385$k$ disposed at the bottom of the second housing member 30$k$. Shown in FIG. 24D is a detailed view of the detail D of the second housing member 30$k$ of the cartridge shown in FIG. 24A, showing: a junction at 387$k$ defined by a segment of a circle, where a blood flow path and a calibration fluid flow path intersect; a bottom seat 388$k$ in cartridge body for mating with ball 377$k$ when the ball is in a down position, for closing off sample duct 385$k$; laminate 369$k$ for covering sample duct 385$k$ and a resilient means, for example a retaining spring 383$k$ (see FIG. 25B); optical chamber 211$k$; optical chamber overflow conduit 227$k$; and blood shunt 86$k$ (FIG. 25D) for bypassing optical chamber 211$k$. Elements 376$k$ of a directional valve are show in FIG. 24A but due to the small sizes, the elements must be viewed in conjunction with FIGS. 24D, 25B, 25E, 26B and 26D, for a better understanding of the directional valve.

Shown in FIG. 25A is a top view of the cartridge 10$k$ in a closed configuration. Shown in FIGS. 25A-25E is the ball 377$k$ of elements of directional valve 376$k$ in an up position, and shown in FIGS. 26A-26E is the ball 377$k$ in a down position. Shown in FIG. 25B is a first (enlarged) cross-sectional view through the cartridge 10$k$ shown in FIG. 25A along line B-B, showing the ball of a directional valve in an up position. Shown in FIG. 25C is a second (not enlarged) cross-sectional view through the cartridge 10$k$ shown in FIG. 25A along line C-C, showing the ball of the directional valve in an up position. Shown in FIG. 25D is a third (enlarged) cross-sectional view through the cartridge 10$k$ shown in FIG. 25A along line D-D, illustrating a calibration duct 391$k$ for housing calibration sealing member 354$k$ for frictionally engaging the outer surface of the analyzer calibration fluid dispensing needle (also referred to as a dispenser), and an internal segment of the calibration duct 393$k$ for receiving the external calibration fluid. The configuration and function of vacuum sealing member 353$k$ for cartridge 10$k$ is similar to vacuum sealing member 353$j$ for cartridge 10$j$, illustrated in FIG. 23E. In operation, a vacuum hollow needle and an analyzer calibration fluid dispensing needle slide into the vacuum sealing member 353$k$ and the calibration sealing member 354$k$ respectively, when the cartridge 10$k$ is fully inserted in the cartridge receptor of the analyzer. With respect to the cartridge, the calibration fluid flow path begins where the external calibration fluid is delivered to the cartridge (i.e. internal segment 393$k$ of calibration duct 391$k$ shown in FIGS. 25A and 25D) and ends at a point between the biosensor chamber exit 338$k$ and the cartridge exit duct 390$k$. With respect to the system, which includes the cartridge 10$k$ and the analyzer used in conjunction with the cartridge, the calibration fluid flow path begins at the external calibration fluid pouch located in the analyzer (also referred to as, analyzer calibration fluid pouch), and ends at a point between the biosensor chamber exit 338$k$ and the cartridge exit duct 390$k$.

Shown in FIG. 26A is a top view of the cartridge 10$k$ in an open configuration. Shown in FIG. 26B is a first (enlarged) cross-sectional view through the cartridge 10$k$ shown in FIG. 26A along line B-B, showing the ball 377$k$ of the directional valve in a down position. Shown in FIG. 26C is a second (not enlarged) cross-sectional view through the cartridge 10k shown in FIG. 26A along line C-C, showing the ball 377k of the directional valve in a down position. Shown in FIG. 26D is detail D shown in FIG. 26C. Shown in FIG. 26E is a third (enlarged) cross-sectional view through the cartridge 10k shown in FIG. 26A along line E-E, showing the cartridge exit duct 390k for receiving the vacuum hollow needle attached to the analyzer vacuum pump, and calibration duct 391k for receiving the external calibration fluid dispenser. Also shown are the biosensor chamber entrance 336k and the biosensor chamber exit 338k.

Referring to FIGS. 25B and 25E, viewed in conjunction with FIG. 24D, when the ball 377k is in the up position, sample duct 385k and junction 387k are configured so that sample storage well 41k is operatively connected with biosensor chamber 337k. Simultaneously, the ball 377k closes off operative communication between biosensor chamber 337k and internal segment 393k of the calibration duct 391k: calibration duct 391k is operatively connected to the external calibration fluid pouch residing in the analyzer, via the calibration fluid dispensing needle.

Referring to FIGS. 26B and 26D, viewed in conjunction with FIG. 24D, when the ball 377k is in the down position, sample duct 385k and junction 377k are configured so that sample storage well 41k is not operatively connected with biosensor chamber 337k. Simultaneously, operative communication between biosensor chamber 337k and the calibration duct 391k is established. A resilient means, for example spring 383k, keeps the ball in the up position, and the stem 379k must be pushed downward in order to keep the ball in the down position. An example of means for pushing the ball down is a plunger in the analyzer, activated by a stepper motor or a solenoid. As an example, an O-ring 381k provides a seal between the first housing member 20k and the stem 379k of elements 376k of directional valve.

In some embodiments, the position of the ball is controlled using a metal insert in the valve stem or ball, wherein the metal is capable of being attracted to one or more electromagnets installed in the analyzer above the valve element, below the valve element, or a combination thereof. By activating one of the electromagnets, the valve element may be pulled towards the activated electromagnet. When the analyzer comprises an electromagnet above and below the valve elements, a resilient means, for example a spring, may not be required to reverse ball position. With a single electromagnet, a resilient means, such as a spring, may be required to reverse ball position. A person skilled in the art would understand that a spring can be installed above or below the valve element. Instead of a spring as exemplified by 383k, other types of resilient means may be used, for example a "diaphragm" (378m), made from a resilient material, as shown for cartridge 10m (see 376m, FIGS. 27A-27K).

Overview of Cartridge 10m as a Non-Limiting Example

Cartridge 10m (see FIGS. 27A-27K) is an eleventh embodiment of a cartridge for measuring one or more properties of a blood sample, comprising an optical chamber and a biosensor chamber, but other similar embodiments do not include a biosensor chamber. In the similar embodiments that do not include a biosensor chamber, the optical chamber 211m may be operatively connected to the cartridge exit duct 390m with no other detection chamber in between. Cartridge 10m is similar to cartridge 10k (see FIGS. 24A to 26E). One difference is the design of directional valve elements shown collectively as 376m. Instead of spring (383k in cartridge 10k), the ball 377m is attached to a resilient diaphragm 378m. A person having ordinary skill in the art should understand that a non-resilient diaphragm augmented by a spring (similar to 383k in cartridge 10k), may also be used. The operation of the directional valve elements 376m is similar to the operation described for cartridge 10k.

Shown in FIG. 27A is a top view of the cartridge 10m in a closed configuration, with the ball 377m in an up position. Shown in FIG. 27B is a first enlarged cross-sectional view through the cartridge 10m shown in FIG. 27A along line B-B, showing the ball 377m of the directional valve in the up (or retracted) position. Shown in FIG. 27C is a second enlarged cross-sectional view through the cartridge 10m shown in FIG. 27A along line C-C, showing the ball 377m in the up (or retracted) position.

Shown in FIG. 27D is a top view of the cartridge 10m in an open configuration, with the ball 377m in a down position. Shown in FIG. 27E is a first enlarged cross-sectional view through the cartridge 10m shown in FIG. 27D along line E-E, showing the ball 377m of the directional valve in the down (or extended) position. Shown in FIG. 27F is a second enlarged cross-sectional view through the cartridge 10m shown in FIG. 27D along line F-F, showing the ball 377m in the down (or extended) position.

Shown in FIG. 27G is a perspective view of the valve element 376m of cartridge 10m, in an inverted position, in order to display the ball 377m in a retracted position. Shown in FIG. 27H is a front view of the valve element 376m shown in FIG. 27G, showing the ball 377m in the retracted position (compare with FIG. 27K, where the ball 377m is in an extended position). Shown in FIG. 27J is a perspective view of the valve element 376m of cartridge 10m, in an inverted position, in order to display the ball 377m in an extended position. Shown in FIG. 27K is a front view of the valve element 376m shown in FIG. 27J (compare with FIG. 27H, where the ball 377m in a retracted position). The diaphragm 378m forms a seal with the first housing member 20m, illustrated in FIGS. 27B, 27C, 27E and 27F.

Sample Measurement Using Positive Pressure

The following is a description of a method for measuring one or more properties of a blood sample, using cartridges similar to cartridges 10, 10b, 10c, 10d, 10e, 10f, 10g and 10h previously described explicitly or implicitly, which do not include biosensor chambers. The cartridges comprise an air bladder for providing positive pressure, and an optical chamber. The method comprises some or all of the following steps, not necessarily in the sequence given:

a) providing a cartridge in an unsealed configuration, the cartridge comprising a cartridge cap pivotally attached to the cartridge via a hinge, a sample storage well and an air bladder, each in communication with an air bladder exit port, and an optical chamber in communication with the sample storage well;

b) providing an analyzer comprising:
1) a receptor for receiving the cartridge;
2) one or more processors for controlling the analyzer and calculating the one or more properties of the blood sample from one or more signals received by one or more detectors located within the analyzer;
3) a source of electromagnetic radiation for interrogating the blood sample in the optical chamber of the cartridge;
4) means for activating or squeezing the air bladder of the cartridge; and
5) the one or more detectors for receiving the one or more signals from the optical chamber and sending the one or more signals to the one or more processors for transforming the one or more signals into the one or more properties of the blood sample;

c) depositing the blood sample from a body part or from a syringe, into the sample storage well;

d) rotating the cartridge cap about the hinge, thereby adjusting the cartridge from an unsealed configuration to a sealed configuration and producing a sealed cartridge, wherein a recess in either the cartridge cap or the cartridge body or a combination thereof facilitates provision of a closed air passage operatively connecting the air bladder exit port and the sample storage well, for communicating pressurized air from the air bladder exit port to the sample storage well for urging the blood towards the optical chamber;

e) inserting the sealed cartridge into the receptor of the analyzer;

f) squeezing or activating the air bladder for providing the pressurized air;

g) urging the blood or a mixture of the blood and one or more reagents into the optical chamber; and h) measuring the one or more properties of the blood sample.

It should be understood that any means used to activate the air bladder or squeeze the air bladder in order to provide or generate pressurized air, are considered to be within the scope of the present invention.

Some methods for measuring a property of a blood sample, for example prothrombin time or activated clotting time, may further comprise dissolving the one or more than one reagent into the blood, prior to urging the mixture of blood and the one or more reagents into the detection chamber.

Other methods for measuring a property of a blood sample, for example prothrombin time or activated clotting time, may further comprise: a) providing a cartridge in an unsealed configuration, further comprising an optical chamber; b) providing an analyzer further comprising a source of electromagnetic radiation and a detector for collecting electromagnetic radiation transmitted through the unclotted or clotted blood in the optical chamber or reflected from the unclotted or clotted blood in the optical chamber; c) applying a pre-determined calibration algorithm to the collected electromagnetic radiation to measure hematocrit of the blood sample to produce a hematocrit measurement; and d) using the hematocrit measurement to correct the property of the blood sample, for example prothrombin time or activated clotting time, for the actual plasma volume in the blood sample.

Later, methods will be described for measuring one or more properties of a blood sample, using cartridges similar to cartridges 10, 10b, 10c, 10d, 10e, 10f, 10g and 10h previously described explicitly or implicitly. The cartridges comprise an air bladder for providing positive pressure, an optical chamber, and a biosensor chamber disposed in the blood flow path downstream of the optical chamber overflow conduit, the biosensor chamber comprising one or more biosensors for generating one or more signals used to calculate the one or more properties of the blood sample. As will be seen, some cartridges further comprise a calibration fluid pouch containing calibration fluid for calibrating the one or more biosensors.

Sample Measurement Using Negative Pressure

The following is a description of a method for measuring one or more properties of a blood sample, using cartridges similar to cartridges 10j, 10k and 10m previously described explicitly or implicitly, which do not include biosensor chambers. Negative pressure is provided by a vacuum pump in a system comprising an analyzer and a cartridge. The method comprises some or all of the following steps, not necessarily in the sequence given:

a) providing the cartridge in an open configuration, the cartridge comprising a cartridge cap pivotally attached to the cartridge via a hinge, a sample storage well in communication with an optical chamber, the cartridge in an open configuration;

b) providing an analyzer comprising:
1) a receptor for receiving the cartridge;
2) a vacuum pump for generating negative pressure;
3) a vacuum hollow needle comprising a first end operatively connected to the vacuum pump, a second end, distal to the first end and operatively connected to the first end, the second end defining an opening, the vacuum hollow needle further comprising an outer surface for frictionally engaging a vacuum sealing member in the cartridge, whereby the negative pressure is transferable to the second end of the vacuum hollow needle;
4) one or more processors for controlling the analyzer and calculating one or more properties of the blood sample from one or more signals received by one or more detectors located within the analyzer;
5) the one or more detectors for receiving one or more signals from the optical chamber and sending the one or more signals to the one or more processors for transforming the one or more signals into the one or more properties of the blood sample;

c) depositing the blood sample from a body part, or from a syringe, into the sample storage well;

d) rotating the cartridge cap about the hinge thereby adjusting the cartridge from an open configuration to a closed but not sealed configuration to produce a closed cartridge, whereby the blood in a sample storage well of the cartridge is maintained at atmospheric pressure;

e) inserting the closed cartridge into the analyzer receptor, and engaging the vacuum hollow needle and the vacuum sealing member of the cartridge, whereby the negative pressure can be transferred from the open end of the vacuum hollow needle to the cartridge;

f) activating the analyzer vacuum pump and transferring the negative pressure to the leading edge of the blood via the cartridge exit duct;

g) urging the blood or a mixture of the blood and one or more reagents into the optical chamber; and h) measuring the one or more properties of the blood sample.

Later, methods will be described for measuring one or more properties of a blood sample, using cartridges similar to cartridges 10j, 10k and 10m previously described explicitly or implicitly. The cartridges comprise an optical chamber and a biosensor chamber disposed in the blood flow path downstream of the optical chamber overflow conduit, the biosensor chamber comprising one or more biosensors for generating one or more signals used to calculate the one or more properties of the blood sample. As will be seen, some cartridges further comprise a calibration duct for receiving external calibration fluid for calibrating the one or more biosensors.

Sample Measurement (Using Cartridges 10e, 10f and 10g as Non-Limiting Examples)

The following is a description of a method for measuring one or more properties of a blood sample, using one of cartridges 10e, 10f or 10g previously described explicitly or implicitly. The method comprises some or all of the following steps, not necessarily in the sequence given:

a) providing a cartridge comprising a cartridge cap pivotally attached to the cartridge via a hinge, a sample storage well and an air bladder, each in communication with an air bladder exit port, an optical chamber and a biosensor chamber in communication with the sample storage well;
  b) providing an analyzer comprising:
  1) a receptor for receiving the cartridge;
  2) one or more processors for controlling the analyzer and calculating the one or more properties of the blood sample from one or more signals received by one or more detectors located in the analyzer;
  3) a source of electromagnetic radiation for interrogating the blood in the optical chamber;
  4) means for activating the air bladder located within the cartridge; and
  5) one or more detectors for receiving the signals from the optical chamber and the biosensor chamber and sending the signals to the one or more processors for transforming the signals into the properties of the sample;
  c) depositing the blood sample from a body part or from a syringe, into the sample storage well;
  d) rotating the cartridge cap about the hinge thereby adjusting the cartridge from an unsealed configuration to a sealed configuration to produce a sealed cartridge, wherein a recess in the cap, the cartridge body, or a combination thereof, facilitates provision of a closed air passage operatively connecting the air bladder exit port and the sample storage well for communicating pressurized air from the air bladder exit port to the sample storage well for urging the blood towards the optical chamber and the biosensor chamber;
  e) inserting the sealed cartridge into the analyzer receptor;
  f) activating the air bladder for providing the pressurized air;
  g) urging the blood into the optical chamber and into the biosensor chamber and stopping the leading edge of the blood at a point after the biosensor chamber exit; and
  h) measuring the properties of the blood sample.

Sample Measurement (Using Cartridge 10h as a Non-Limiting Example)

The following is a description of a method for measuring one or more properties of a blood sample, using cartridge 10h illustrated collectively in FIGS. 20A-21H, previously described explicitly or implicitly. The method comprises some or all of the following steps, not necessarily in the sequence given:
  a) providing a cartridge in an open configuration, the cartridge comprising a cartridge cap pivotally attached to the cartridge via a hinge, a sample storage well and an air bladder, each in communication with an air bladder exit port, an optical chamber, an optical chamber overflow conduit, and a biosensor chamber in communication with the sample storage well, and a calibration fluid pouch in communication with the biosensor chamber;
  b) providing an analyzer comprising:
  1) a receptor for receiving the cartridge;
  2) one or more processors for controlling the analyzer, and for receiving and processing signals from the sample in the detection chambers located in the cartridge;
  3) a source of electromagnetic radiation for interrogating the blood in the optical chamber;
  4) means for activating the air bladder;
  5) means for rupturing, or causing the rupturing of, the calibration fluid pouch;
  6) one or more detectors for receiving the signals from the optical chamber and the biosensor chamber; and
  7) means for sending the signals from the detectors to the one or more processors for transforming the signals into a plurality of properties of the sample;
  c) depositing the blood sample from a body part or from a syringe, into the sample storage well;
  d) rotating the cartridge cap about the hinge thereby adjusting the cartridge from an unsealed configuration to a sealed configuration to produce a sealed cartridge, wherein a cap recess facilitates provision of a closed air passage operatively connecting the air bladder exit port and the sample storage well for communicating pressurized air from the air bladder exit port to the sample storage well for urging the blood towards the optical chamber;
  e) inserting the sealed cartridge into the analyzer receptor;
  f) activating the air bladder for providing the pressurized air for urging the blood into the optical chamber;
  g) stopping the leading edge of the blood at a point between the optical chamber overflow conduit at junction 367h (see FIGS. 21D and 21H);
  h) interrogating the blood in the optical chamber with the source of electromagnetic radiation in the analyzer;
  i) sending the signals from the optical chamber received by the one or more detectors, to the one or more processors for transforming the signals into one or more properties of the sample;
  j) rupturing the calibration fluid pouch;
  k) applying additional force to the calibration fluid pouch in order to urge the calibration fluid into the biosensor chamber for calibrating one or more biosensors in the biosensor array (see for example CA Pat. No. 2,978,737 to Samsoondar, and U.S. Pat. No. 5,096,669 to Lauks, both incorporated herein by reference);
  l) after calibrating the biosensors, squeezing the air bladder in order to urge the leading edge of the blood into the biosensor chamber, thereby displacing the calibration fluid from the biosensor chamber; and
  m) sending the signals from the biosensor chamber to the one or more processors for transforming the signals into the one or more properties of the blood sample.

Sample Measurement (Using Cartridge 10j as a Non-Limiting Example)

The following is a description of a method for measuring one or more properties of a blood sample, using cartridge 10j illustrated collectively in FIGS. 22A-23G previously described explicitly or implicitly. The method comprises some or all of the following steps, not necessarily in the sequence given:
  a) providing a cartridge in an open configuration, the cartridge comprising a cartridge cap pivotally attached to the cartridge via a hinge, and a sample storage well in communication with an optical chamber, an optical chamber overflow conduit, and a biosensor chamber, a cartridge exit duct in communication with the biosensor chamber, the cartridge exit duct comprising a vacuum sealing member;
  b) providing an analyzer comprising:
  1) a receptor for receiving the cartridge;
  2) one or more processors for controlling the analyzer, and for receiving and processing signals from the sample in the detection chambers;
  3) a source of electromagnetic radiation for interrogating the blood in the optical chamber;
  4) a vacuum pump for generating negative pressure;
  5) a vacuum hollow needle comprising a first end operatively connected to the vacuum pump, a second end, distal to the first end and operatively connected to the first end, the second end defining an opening, the vacuum hollow needle further comprising an outer surface for sliding into the cartridge exit duct;

6) one or more detectors for receiving the signals from the optical chamber and the biosensor chamber; and 7) means for sending the signals from the detectors to the one or more processors for transforming the signals into a plurality of properties of the sample;

c) depositing the blood sample from a body part or from a syringe, into the sample storage well;

d) rotating the cartridge cap about the hinge thereby adjusting the cartridge from an open configuration to a closed but not sealed configuration, to produce a closed cartridge;

e) inserting the closed cartridge into the analyzer receptor;

f) inserting the vacuum hollow needle into the cartridge exit duct, which comprises the vacuum sealing member for frictionally engaging the outer surface of the vacuum hollow needle;

g) activating the analyzer vacuum pump and transferring the negative pressure to the leading edge of the blood;

h) urging the blood into the optical chamber and the biosensor chamber by applying the negative pressure to the leading edge of the blood;

i) interrogating the blood in the optical chamber using the source of electromagnetic radiation in the analyzer;

j) sending the signals from the optical chamber received by the one or more detectors, to the one or more processors for transforming the signals into one or more properties of the sample; and k) sending the signals from the biosensor chamber to the one or more processors for transforming the signals into one or more properties of the sample.

Sample Measurement (Using Cartridges 10k and 10m as Non-Limiting Examples)

The following is a description of a method for measuring one or more properties of a blood sample, using one of cartridges 10k and 10m illustrated collectively in FIGS. 24A-26E and FIGS. 27A-27K respectively, previously described explicitly or implicitly. Because cartridge 10m is very similar to cartridge 10k, except for the design of the directional valves 376k and 376m, the following steps are described primarily for cartridge 10k, and similar steps may be performed for operating cartridge 10m. The method comprises some or all of the following steps, not necessarily in the sequence given:

a) providing a cartridge in an open configuration, the cartridge comprising a cartridge cap comprising a cap breathable plug, the cartridge cap pivotally attached to the cartridge via a hinge, a sample storage well in communication with an optical chamber, an optical chamber overflow conduit, and a biosensor chamber, a cartridge exit duct in communication with the biosensor chamber, the cartridge exit duct comprising a vacuum sealing member, and a cartridge calibration duct in communication with the biosensor chamber, the cartridge calibration duct comprising a calibration sealing member;

b) providing an analyzer comprising:

1) a receptor for receiving the cartridge;

2) one or more processors for controlling the analyzer, and for receiving and processing signals from a sample in the optical chamber and the biosensor chamber;

3) a source of electromagnetic radiation for interrogating the blood in the optical chamber;

4) a vacuum pump for generating negative pressure;

5) a vacuum hollow needle comprising a first end operatively connected to the vacuum pump, a second end, distal to the first end and operatively connected to the first end, the second end defining an opening, the vacuum hollow needle further comprising an outer surface for sliding into the cartridge exit duct facilitated by a vacuum sealing member in the cartridge;

6) an analyzer calibration fluid pouch, the analyzer calibration fluid pouch comprising a collapsible wall and a calibration fluid needle/dispenser, the dispenser comprising a first end in operative communication with the pouch, a second end distal to the first end for dispensing calibration fluid, and an outer surface for sliding into the cartridge calibration duct, facilitated by the calibration sealing member;

7) one or more detectors for receiving the signals from the optical chamber and the biosensor chamber; and 8) means for sending the signals from the detectors to the one or more processors for transforming the signals into a plurality of properties of the sample;

c) depositing the blood sample from a body part or from a syringe, into the sample storage well;

d) rotating the cartridge cap about the hinge thereby adjusting the cartridge from an open configuration to a closed but not sealed configuration to produce a closed cartridge, whereby the blood in the sample storage well is subjected to atmospheric pressure facilitated by the cap breathable plug;

e) inserting the closed cartridge into the analyzer receptor;

f) inserting the vacuum hollow needle into the vacuum sealing member, and inserting the calibration fluid dispenser into the calibration sealing member;

g) arranging the directional valve ball to a first position that permits passage of the blood past the ball valve (see FIGS. 25B and 25E), the arranging facilitated by a resilient means, for example spring (383k);

h) activating the analyzer vacuum pump and transferring negative pressure to the leading edge of the blood;

i) urging the blood into the optical chamber overflow conduit via the optical chamber and/or the blood shunt (86k) by applying the negative pressure to the leading edge of the blood;

j) deactivating the vacuum pump;

k) interrogating the blood in the optical chamber using the source of electromagnetic radiation in the analyzer;

l) sending the signals from the optical chamber received by the one or more detectors, to the one or more processors for transforming the signals into one or more properties of the sample;

m) arranging the directional valve ball to a second position (see FIGS. 26B and 26D) that permits passage of calibration fluid past the ball valve, the arranging facilitated by for example, a plunger and a stepper motor in the analyzer;

n) re-activating the analyzer vacuum pump and transferring the negative pressure to the leading edge of calibration fluid in an internal segment of the calibration duct (393k), for a predetermined period;

o) urging the calibration fluid into the biosensor chamber by applying the negative pressure to the leading edge of the calibration fluid;

p) deactivating the vacuum pump;

q) calibrating one or more biosensors of the biosensor array;

r) deactivating the plunger and rearranging the ball to the first position, facilitated by a resilient means, for example spring (383k);

s) re-activating the analyzer vacuum pump and transferring the negative pressure to the leading edge of blood (located in the optical chamber overflow conduit), for a predetermined period, causing the blood to displace the calibration fluid from the biosensor chamber (an air bubble may become inserted between the blood and the calibration fluid, depending on the space between the leading edge of the blood in the optical chamber overflow conduit 227k and junction 387k), and bringing the leading edge of the blood to a stop at a point between the biosensor chamber exit 338k and the cartridge exit duct 390k;

t) sending the signals from the biosensor chamber to the one or more than one processor for transforming the signals into one or more properties of the blood sample.

Method for Spectroscopic Measurement

An embodiment of a system for spectroscopic measurement or testing of whole blood comprises an analyzer and a disposable cartridge is also provided herein. Other terms like spectrophotometric, photometric or optical measurement are sometimes used instead of spectroscopic measurement. The analyzer comprises a source of electromagnetic radiation (EMR) and one or more photodetectors for measuring the EMR reflected from the sample in the optical chamber or transmitted through the sample in the optical chamber. The source of EMR, which impinges upon or interrogates the contents of the optical chamber, may be a tungsten lamp (other lamps may be used), one or more lasers, and one or more light-emitting diodes (LEDs) across a range of wavelengths as is well known in the art, and without being limited in any way. The analyzer may also include a spectrometer, which may comprise multichannel detectors such as a photodiode array (PDA) or a charge-coupled device (CCD), for example, without being limited in any way. The spectrometer may also comprise a transmission or reflection grating for dispersing EMR reflected from a sample (i.e., reflectance, denoted by R) or EMR transmitted through a sample (i.e. transmittance, denoted by T), into component wavelengths.

Preferably the spectrometer comprises a multichannel photodetector arranged as a linear PDA detector installed in the spectrometer, for example, a linear repetitive installation of discrete photodiodes on an integrated circuit chip. For measuring transmittance, the source of EMR and the PDA detector should be on opposite sides of the optical chamber, and for measuring reflectance, both the source of EMR and the PDA detector should be on the same side of the optical chamber. For reflectance measurement, the side of the optical chamber distal to the source of EMR may comprise a reflecting member, or a distal window of the optical chamber may be used as a reflecting member. Alternatively, a reflecting member may be installed in the cartridge receptor of the analyzer, in close proximity to the optical chamber window distal to the source of EMR.

For illustration of the method, by way of example which is not to be considered limiting, the PDA detector may have a pixel dispersion of 2 nanometers per pixel (i.e., the pixel or digital resolution), and the PDA detector is calibrated to read from wavelengths (denoted by $\lambda$) 300 nanometers to 812 nanometers. In this example, the center of pixel 1 is assigned a wavelength of 300 nanometers, and the center of pixel 256 is assigned a wavelength of 812 nanometers, thereby providing a wavelength range of 300-812 nanometers. For clarity, since the center of pixel 1 is assigned 300 nanometers, the center of pixel 2 will be assigned 302 nanometers, the center of pixel 3 will be assigned 304 nanometers and so on in increments of 2 nanometers per pixel (the pixel dispersion). A person skilled in spectroscopy should appreciate that the wavelength range and spectral resolution of the PDA detector depends on several factors, for example, the semiconductor material used to construct the PDA, and grating and the orientation of the grating relative to the PDA detector; the source of EMR is a major determinant of the wavelength range. Each pixel is typically scanned in microseconds, which should provide sufficient time to accumulate sufficient charge on the photodiode, for example to distinguish a signal from noise and dark current, without saturating the photodiode.

Saturation, or "saturating the photodiode", means that the photodiode has reached a maximum response in current and any additional photons impinging upon the photodiode is usually converted to heat instead of current. Because the scanning time is so short, it is reasonable to say that all the photodiodes in the PDA detector are scanned simultaneously. The photons are converted to electrical current, which is measured and digitized. In this present example, absorbance (denoted by A) may be determined, where $$A = -\log 10 T.$$

It is well known that transmittance is defined as the fraction of incident light which is transmitted, or that passes through, a sample. Thus:

$$T = I/Io, \text{ where}$$

Io=the intensity of light (or EMR) impinging upon the sample (i.e. the incident light) and I=the intensity of light (or EMR) after passing through the sample.

For calculating transmittance, the amount of EMR impinging upon the optical chamber, Io, may be measured by interrogating an optical chamber containing air. The EMR impinging upon the optical chamber, Io, may be measured before or after every sample measurement, or less frequently and stored in the processor for later use. A measurement of the absorbances (or more accurately stated, the calculation of the absorbances) over the full wavelength range is collected over time (t). In this example, the absorbance data is displayed in Table 3, below.

For example, $A\lambda 300$ t0 is the absorbance at 300 nanometers measured at zero time, and $A\lambda 812$ t60 is the absorbance at 812 nanometers measured at 60 seconds. The table comprises 256 columns (one for each wavelength or pixel) and 61 rows (one per second, including zero time).

In the example below, the measurements are used to estimate prothrombin time (PT; usually reported as PT-INR; PT-International Normalized Ratio), activated partial thromboplastin time (aPTT), or thrombin time (TT), and since a normal PT is about 10-14 seconds, a normal ACT is about 70-130 seconds, and a normal TT is about 15-19 seconds, the measurements are performed every second. An aspect of the present invention with respect to coagulation measurements, e.g. PT, ACT and TT, is to use the absorbance at one or more wavelengths or pattern recognition using absorbances at a plurality of wavelengths. Techniques of pattern recognition, combined with spectroscopy are known by those having skill in the art. An example where spectroscopy combined with pattern recognition algorithm are used to identify coffee variety is provided in Zhang et. Al. (Mid-Infrared Spectroscopy for Coffee Variety Identification: Comparison of Pattern Recognition Methods", J. of Spectroscopy, Volume 2016, Article ID 7927286, the contents of which are incorporated herein by reference). As blood coagulates, the blood changes from various liquid varieties to various gel varieties, with corresponding changes in spectroscopic patterns, allowing one to use similar techniques as those used by Zhang et. al. to identify different variety of coffee beans. An example of a method for measuring clotting time, which does not use pattern recognition and uses absorbances at a plurality of wavelengths, is provided below. The specific blood coagulation time measured depends on the reagents included in the disposable cartridge. For example, thromboplastin may be used for PT, celite or kaolin may be used for ACT, and thrombin may be used for TT.

Typically, blood coagulation time is measured using mechanical methods. For spectroscopic-based assays, using citrated plasma is usually used in place of whole blood, since the amount of EMR that reaches the photodetector is reduced as most of the incident EMR is scattered and absorbed by the blood cells. As a result the signal to noise ratio may not be sufficient to obtain reliable measurements. However, separating out the plasma from the whole blood requires time and centrifugation equipment. It is well known that as plasma clots or coagulates, the absorbance at a single wavelength increases. By way of example, G. O. Gogstad et. al. (1986, "Turbidimetric Determination of Prothrombin Time by Clotting in a Centrifugal Analyzer" Clin. Chem. 32/10, 1857-1862; the contents of which are incorporated herein by reference), describe the change in absorbance spectra of plasma during coagulation. However, measurement of coagulation time using whole blood instead of plasma is more representative of in vivo coagulation, and whole blood is the preferred sample for POCT. As a result there is a need for spectroscopic measurement of the blood coagulation time employing whole blood. In order to improve the signal to noise ratio when whole blood is used with the devices as described herein, the depth of the optical chamber should be relatively small, for example about 100 micrometers. However, the use of absorbance, reflectance or transmittance at a single wavelength to generate a clotting reaction curve as shown in FIG. 1 of Cogstad et. al. (1986) using absorbance for example, and the calculations used to compute clotting time, are considered to be within the scope of the present invention. Cogstad et. al. provided examples of calculations use to compute clotting time.

The source of EMR in the example provided below may be a tungsten lamp. U.S. Pat. No. 6,651,015 to Samsoondar, the contents of which are incorporated herein by reference, describes in detail how spectrophotometric apparatus are calibrated using multi-wavelength analysis. With the use of a source of EMR like a tungsten lamp, which provides multiwavelength EMR (the tungsten lamp is polychromatic, whereas a laser is monochromatic), and the use of a linear PDA detector, the analyzer has the capacity to generate full absorbance spectra in milliseconds. Several spectra may be collected over milliseconds and the absorbances averaged to minimize noise. Mathematical smoothing techniques, which are covered extensively in the literature, may be used to minimize noise. Other mathematical techniques like the use of an order derivative of absorbance are also discussed in U.S. Pat. No. 6,651,015 to Samsoondar. Even though full absorbance spectra are obtained, as tabulated in Table 3 (below), the temporal absorbances at one or more wavelengths may also be used. Furthermore, selected portions of the absorbance spectra, a range of the absorbance spectra, or the full absorbance spectra, may be used.

As stated in U.S. Pat. No. 6,651,015, "By "Derivative of Absorbance" it is meant an order derivative of the absorbance spectrum. Zero order derivative of absorbance is the measured absorbance. The first order derivative of absorbance at a particular wavelength is the slope of the absorbance spectrum at that wavelength; the Second order derivative of absorbance at a particular wave length is the slope of the first derivative absorbance spectrum at the wavelength." The same concept may be applied to any other curve other than an absorbance curve, for example, a temporal correlation coefficient curve, which is discussed below.

A different optical technique for measuring coagulation times (e.g. PT) is provided in Faivre et. al. ("Coagulation dynamics of a blood sample by multiple scattering analysis", J. Biomed. Optics 16(5), May 2011, the contents of which are incorporated herein by reference). This method relies on the detection of blood cell mobilization while the blood is being trapped into the clot as coagulation occurs. This method relies on the analysis of a speckle figure that results from whole-blood mixed with coagulation reagent which is then introduced in the optical chamber and illuminated with coherent light. Coherent light is a beam of photons that have the same wavelength and are in phase, e.g. a laser.

As explained by Faivre et. al. (2011), the speckle pattern results from the multiple scattering of a high number of randomly distributed diffusing objects, when illuminated by coherent light. For example, when illuminating a suspension of diffusing particles with a laser, each particle diffuses the light, and the constructive or destructive interferences between the diffused rays form a speckled image. In the case of a blood sample, as the cells are unbound, their residual motions due to the spontaneous migration in the optical chamber induce a constantly changing speckle figure, exhibiting a "swarmlike" behavior. Therefore, consecutive speckle images (i.e., temporal images) of cells in unclotted blood are expected to be poorly correlated. When the blood clot forms, the cells are immobilized to form a speckle image that is fixed in time. Therefore consecutive speckle images of cells in clotted blood are expected to be highly correlated.

The approach described by Faivre et. al. (2011), comprises imaging a multiple speckle images using a CCD camera as a multispeckle light detector. In order to determine when the blood cells are immobilized, the differences between two consecutive images must be quantified, and the correlation coefficient between the two images is calculated. A plot of the correlation coefficients on the y-axis and time on the x-axis is used to determine when the blood begins to clot and the time when the clot is solid. Improved analysis was performed using the derivative of the correlation coefficient instead of the correlation coefficient. The first derivative, for example, makes it easier for one to examine the graph and visually pick the time when clotting begins and the time when clotting is essentially complete (as described in Faivre et, al. 2011)). The use of derivatives of curves are explained in greater detail below. The CCD camera used by Faivre et. al. (2011) is a two-dimensional array of CCDs, and the source of EMR is a laser. Faivre et. al. (2011) does not describe or suggest the use of polychromatic EMR, or the use of a linear (one-dimensional) PDA detector, for measuring blood coagulation times.

Method for Measuring Blood Coagulation Time

A method for measuring blood coagulation of a blood sample comprises some or all of the following steps, not necessarily in the sequence given. The method may include the following:

a) Providing a system comprising a disposable cartridge, an analyzer, and one of positive pressure means for regulating blood flow in the cartridge, and negative pressure means for regulating blood flow in the cartridge.

The cartridge comprises: a cartridge body having an upper surface and a lower surface; a sample storage well comprising a top portion for receiving the blood sample and a bottom portion for releasing at least a portion of the blood sample into a sample storage conduit, wherein the area of the top portion is substantially larger than the area of the bottom portion; an optical chamber for generating one or more signals during sample interrogation; and a sample storage conduit comprising at least one reagent and fluidly connecting the sample storage well and the optical chamber.

The analyzer comprises: a receptor for receiving the cartridge; a source of electromagnetic radiation (EMR) for interrogating the contents of the optical chamber; a spectrometer comprising a grating for dispersing the EMR emerging from the sample in the optical chamber, into component wavelengths, and a one-dimensional multi-channel detector for receiving the dispersed EMR from the grating, and one or more processors for controlling the analyzer and processing the signals received by the spectrometer.

b) Receiving the blood sample in the sample storage well;

c) Establishing the blood flow;

d) Dissolving and mixing the one or more reagent with a portion of the blood sample to produce a mixed blood sample;

e) Filling the optical chamber with at least some of the mixed blood sample;

f) Interrogating the mixed blood sample in the optical chamber with the EMR in a temporal manner, for example, but not limited to, 1 second interval (the integration time per scan may be in the order of microseconds, and multiple scans may be averaged in order to reduce noise) over an interrogation period of, for example, 60 seconds, at one or more wavelengths, to produce a plurality of optical measurements, where each optical measurement of the plurality of optical measurements, is obtained for each time measurement, as shown in Table 3 below. Interrogation may be triggered at a predefined time, for example, around the time when the blood makes contact with the one or more reagent;

g) Measuring the clotting time from the plurality of optical measurements at one or more wavelengths, where the clotting time is the length of time from a selected time a coagulation process is considered to begin to a selected time the coagulation process is considered to end. The selected time the coagulation process is considered to end may be when the plurality of optical measurements stabilize so that sequential optical measurements no longer vary significantly in value, or the time where an inflection point in the clotting reaction curve occurs (see FIG. 1 of Cogstad et. al. (1986)). When one or more reagent is added to the blood, the beginning of the coagulation dynamics may be defined, but other predefined criteria may also be used. Multiple clotting reaction curves may be developed, one for each wavelength used, and the average clotting time may be calculated from the multiple clotting reaction curves. Other adjustments may be performed on the calculated clotting time, in order to provide clotting times that correlate with the clotting times generated by laboratory methods that use plasma instead of whole blood. Predefined criteria for defining when clotting is considered to begin and when clotting is considered to end, may incorporate adjustments necessary to provide clotting times that correlate with the clotting times generated by laboratory methods that use plasma instead of whole blood.

The method may further comprise:

h) Preparing a primary two-dimensional matrix of temporal or sequential optical measurements, wherein each row in the matrix represents the optical measurements at all wavelengths (pixels) at one time, and each column in the matrix represents the temporal optical measurements at one wavelength (pixel). It should be understood that the matrix could be transposed, such that rows become columns and columns become rows. Pixels are usually assigned wavelengths after the spectrometer is calibrated, usually using lasers and the wavelengths of the lasers;

i) Preparing a secondary two-dimensional matrix, a subset of the primary two-dimensional matrix, by selecting a plurality of columns and a plurality of rows for use in the blood coagulation measurement. For example, from the 61 temporal measurements at 300-812 nanometers shown in Table 3 below, the rows for times other than 0, 5 10, 15, 20, 25 . . . 50, 55 and 60 seconds (i.e., 13 different times) are deleted and all the wavelengths except 500, 550, 600, 650, 700, 750 and 800 nanometers (i.e., 7 wavelengths) are deleted, creating a 13×7 matrix. Deleting the times as described may not be preferred where the optical signals are changing rapidly, and when the required accuracy of the measured clotting time is high. In some time periods where optical signals are not changing significantly, it may be preferred to delete blocks of time from that time period, and in some time periods where significant optical signals are changing, less deletion may be preferred. The rows and columns that are deleted may be best determined by trial and error, and the secondary matrix may comprise rows and columns that appear to be selected randomly. In this example of a 13×7 subset of the primary two-dimensional matrix, the rows may be identified as R1, R2, R3 . . . R11, R12 and R13 to facilitate the explanation below.

j) Calculating a correlation coefficient between the first pair of rows, i.e., R1 and R2 (R1 is the same as t0);

k) Calculating a correlation coefficient between a subsequent second pair of rows, which may be R2 and R3 or R3 and R4, for example, provided that one of the rows in the second pair is from a later time not used in the first pair;

l) Calculating a correlation coefficient between a subsequent third pair of rows, which may be R3 and R4 or R4 and R5, for example, provided that one of the rows in the third pair is from a later time not used in the first or second pair;

m) Continuing the calculation of correlation coefficients as before until the correlation coefficient between the last pair of rows is calculated.

n) Generating an order derivative (for example zero, first, and second order derivative) of the calculated correlation coefficients plotted against time for identifying when the coagulation process ends. Preferably, the correlation coefficient is plotted on the y-axis and time on the x-axis, and such a plot is referred to as a temporal correlation coefficient curve. The time when coagulation is considered to have come to an end and used to calculate the clotting time may be defined by the inflection point in the rising portion of the temporal correlation coefficient curve, or other computing means, for example as provided by Cogstad et. al. (1986). Mathematical equations may be installed in the analyzer processor and used to locate the inflection point. Alternatively, particularly for visual inspection of the coagulation dynamics for quality assurance, the first order derivative of the temporal correlation coefficient curve may be displayed, where the inflection point is displayed as a peak (see FIG. 3 in Faivre et. al. (2011))]. The use of an order derivative of a curve is explained in greater detail below. As explained above, regarding an absorbance spectrum with respect to wavelength, a zero-order derivative of a curve is the same curve;

o) Applying a predefined criteria to the order derivative of a temporal correlation coefficient curve for identifying at which selected time a coagulation process is considered to begin and at which selected time the coagulation process is considered to end, to determine a specific blood coagulation time. As examples which should not be considered limiting, the time the coagulation process is considered to begin is the time when the blood makes contact with the one or more reagents, and the time when the coagulation process is considered to end is the time identified by the inflection point in the steep rising portion of the temporal correlation coefficient curve. It is understood by those having skill in the art that the clotting process is very complex, and the selected times a coagulation process is considered to begin and end may be arbitrary. An example of a study that demonstrates the complexity of clotting is provide in Greco ("Reflectance Spectroscopy of Clotting Blood: A description of the Time-Dependent Behavior", Arch. Pathol. Lab. Med., Vol 128, February 2004, the contents of which are incorporated herein by reference). In FIG. 1 of Greco, they identify four general regions: a rapid monotonic decrease of reflected light intensity, a sigmoidal increase of reflected light intensity, a region of linear increase of reflected light intensity, and a terminal phase.

p) Reporting the specific blood coagulation time.

As one of skill would understand, the one or more reagents included in the cartridge determines which coagulation time is being measured, for example, PT, ACT or TT.

TABLE 3

Absorbance data collected by 256 pixels from a single sample interrogated over a 60 second period

| Time (t) in | Pixel (Resolution elements or individual photodiodes) | | | | | |
|---|---|---|---|---|---|---|
| | 1 | 2 | 3 | ...253 | 255 | 256 |
| | Wavelength ($\lambda$) in nanometers | | | | | |
| seconds | 300 | 302 | 304 | 808 | 810 | 812 |
| 0 | $A_{\lambda 300\ t0}$ | $A_{\lambda 302\ t0}$ | $A_{\lambda 304\ t0}$ | ...$A_{\lambda 808\ t0}$ | $A_{\lambda 810\ t0}$ | $A_{\lambda 812\ t0}$ |
| 1 | $A_{\lambda 300\ t1}$ | $A_{\lambda 302\ t1}$ | $A_{\lambda 304\ t1}$ | ...$A_{\lambda 808\ t1}$ | $A_{\lambda 810\ t1}$ | $A_{\lambda 812\ t1}$ |
| 2 | $A_{\lambda 300\ t2}$ | $A_{\lambda 302\ t2}$ | $A_{\lambda 304\ t2}$ | ...$A_{\lambda 808\ t2}$ | $A_{\lambda 810\ t2}$ | $A_{\lambda 812\ t2}$ |
| ... | ... | ... | ... | ...... | ... | ... |
| 58 | $A_{\lambda 300\ t58}$ | $A_{\lambda 302\ t58}$ | $A_{\lambda 304\ t58}$ | ...$A_{\lambda 808\ t58}$ | $A_{\lambda 810\ t58}$ | $A_{\lambda 812\ t58}$ |
| 59 | $A_{\lambda 300\ t59}$ | $A_{\lambda 302\ t59}$ | $A_{\lambda 304\ t59}$ | ...$A_{\lambda 808\ t59}$ | $A_{\lambda 810\ t59}$ | $A_{\lambda 812\ t59}$ |
| 60 | $A_{\lambda 300\ t60}$ | $A_{\lambda 302\ t60}$ | $A_{\lambda 304\ t60}$ | ...$A_{\lambda 808\ t60}$ | $A_{\lambda 810\ t60}$ | $A_{\lambda 812\ t60}$ |

Selection of columns and rows essentially transforms a 60×256 matrix shown in Table 3, into for example, a 60×10 matrix, if 10 different wavelengths for 60 seconds are used in calculating clotting times. Preferably all the time (i.e. rows) measurements are used, and if sufficiently discernable changes in optical measurements are observed, then a single column (1 wavelength) may be sufficient, in which case, no correlation coefficient coefficients are necessary.

The use of a derivative of a correlation coefficient plot with respect to time is also within the scope of the present invention. For example, with correlation coefficient plotted along the y-axis and time plotted along the x-axis, the first derivative of the correlation coefficient plot represents the rate of change of correlation coefficient with respect to time. A first derivative of the correlation coefficient plot with respect to time has a peak where the upwards slope in the original correlation coefficient plot reaches a maximum, a trough where the downwards slope of the correlation coefficient plot reached a maximum, and a value of zero at any peak in the original correlation coefficient plot. Either side of the maximum correlation coefficient are positive and negative bands with maximum and minimum at the same times as the inflection points in the correlation coefficient peak. Therefore, it is easier to visually identify the inflection points in the original correlation coefficient plot, by using the first derivative of correlation coefficient plot. A second derivative of the correlation coefficient plot with respect to time (the slope of the first derivative of the correlation coefficient plot with respect to time) has peaks and troughs corresponding to the points of maximum curvature in the original correlation coefficient plot, and in particular has a trough corresponding to each peak in the original correlation coefficient plot.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein. Furthermore, the discussed combination of features might not be absolutely necessary for the inventive solution.

I claim:

1. A system for measuring one or more properties of a blood sample, the system comprising:
    a cartridge comprising:
        a cartridge body having an upper surface and a lower surface;
        a sample storage well comprising a top portion for receiving the blood sample and a bottom portion for releasing at least a portion of the blood sample into a sample storage conduit, wherein the area of the top portion is substantially larger than the area of the bottom portion;
        an optical chamber for generating one or more signals during sample interrogation, the one or more signals used to calculate the one or more properties of the blood sample;
        the sample storage conduit for transferring some, or all, of the at least a portion of the blood from the sample storage well to the optical chamber;
        a cap hingedly attached to the cartridge body via a hinge, the cap having a top side and an underside;
    an analyzer, the analyzer comprising:
        a receptor for receiving the cartridge;
        a source of electromagnetic radiation for interrogating the blood sample in the optical chamber and for producing one or more signals, after the cartridge is inserted into the receptor;
        one or more detectors for receiving the one or more signals generated in the optical chamber; and one or more processors for controlling the analyzer and calculating the one or more properties of the blood sample from the one or more signals received by the one or more detectors; and wherein the system further comprising one of:

A) positive pressure means for regulating blood flow in the cartridge, the positive pressure means comprising:
an air bladder in the cartridge for generating pressurized air;
an air bladder exit port located on the upper surface of the cartridge, the air bladder exit port operatively connected with the air bladder;
an overflow conduit in communication with the optical chamber and a vent;
a flat surface located on the upper surface of the cartridge body, the flat surface of the cartridge body surrounding the top portion of the sample storage well and the air bladder exit port; and
a cap flat surface located on the underside of the cap; wherein
the cartridge is adjustable between an unsealed configuration and a sealed configuration by rotating the cap about the hinge;
in the unsealed configuration the sample storage well is configured to receive the blood sample; and
in the sealed configuration a portion of the flat surface of the cartridge body mates with the cap flat surface to form a closed air passage operatively connecting the air bladder exit port to the sample storage well so that pressurized air from the air bladder exit port is transferable to the sample storage well, wherein the closed air passage is facilitated by a groove set into the upper surface of the cartridge body, a recess set into the underside of the cap, or a combination thereof, whereby when the air bladder is squeezed some, or all, of the at least a portion of the blood is urged from the sample storage well towards the optical chamber, and air within the overflow conduit is purged through the vent; and B) negative pressure means for regulating blood flow in the cartridge, the negative pressure means comprising:
a vacuum pump in the analyzer for generating negative pressure;
a vacuum hollow needle comprising a first end operatively connected to the vacuum pump, a second end distal to the first end and operatively connected to the first end, the vacuum hollow needle further comprising an outer surface;
a cartridge exit duct operatively connected to the optical chamber, the cartridge exit duct comprising a vacuum sealing member for frictionally engaging the outer surface of the vacuum hollow needle so that the negative pressure is transferable to the cartridge exit duct; wherein
the cartridge is adjustable between an open configuration and a closed configuration by rotating the cap about the hinge;
in the open configuration the sample storage well is configured to receive the blood sample; and
in the closed configuration, the sample storage well is covered with the cap, the cap further comprising a cap vent for subjecting the blood sample in the sample storage well to atmospheric pressure, whereby some, or all, of the at least a portion of the blood flows from the sample storage well towards the cartridge exit duct when the cartridge exit duct is under negative pressure.

2. The system of claim 1, wherein the top portion of the sample storage well comprises a boss for increasing the sample storage well storage capacity, and wherein the cap rotates about the hinge in a plane substantially orthogonal to a plane generally defined by the upper surface.

3. The system of claim 1, wherein the cartridge further comprises one of an enlarged cavity disposed in the sample storage conduit, and a hydrophobic insert adjacent to and aligned with the sample storage conduit, and the sample storage well further comprising internal walls, the internal walls of the sample storage well characterized as being more wettable than a surface of the sample storage conduit.

4. The system of claim 1, wherein the system comprises the positive pressure means, and the cartridge further comprises a biosensor chamber disposed between the optical chamber and the vent, the biosensor chamber in operative communication with the optical chamber and the vent, and wherein the biosensor chamber comprises one or more biosensors for generating one or more signals used to calculate an additional one or more properties of the blood sample.

5. The system of claim 1, wherein system comprises the negative pressure means, and the cartridge further comprises a biosensor chamber in operative communication with the optical chamber and the cartridge exit duct, and wherein the biosensor chamber comprises one or more biosensors for generating one or more signals used to calculate an additional one or more properties of the blood sample, and a biosensor chamber exit.

6. The system of claim 4, wherein the cartridge further comprises a calibration fluid pouch in operative communication with the biosensor chamber, the calibration fluid pouch containing calibration fluid for calibrating the one or more biosensors.

7. The system of claim 5, wherein the analyzer further comprises:
an analyzer calibration fluid pouch, the analyzer calibration fluid pouch comprising calibration fluid and a collapsible wall, the analyzer calibration fluid pouch for dispensing calibration fluid, the analyzer calibration fluid pouch operatively connected to an analyzer calibration fluid dispensing needle, the analyzer calibration fluid dispensing needle comprising a first end in operative communication with the analyzer calibration fluid pouch, a second end distal to the first end for dispensing the calibration fluid, and an outer surface;
means for operating a directional valve located in the cartridge; and wherein
the cartridge further comprises:
a calibration duct comprising an internal segment of the calibration duct and a calibration sealing member, the calibration sealing member for frictionally engaging the outer surface of the analyzer calibration fluid dispensing needle so that the calibration fluid is transferable from the analyzer calibration fluid pouch to the internal segment of the calibration duct;
a calibration fluid flow path beginning at the internal segment of the calibration duct and ending at a point between the biosensor chamber exit and the cartridge exit duct,
a blood flow path beginning at the sample storage well and ending at a point between the biosensor chamber exit and the cartridge exit duct, and
a junction where the calibration fluid flow path intersects with the blood flow path; and
the directional valve disposed at the junction and movable from a first position to a second position, wherein in the first position the directional valve establishes an-operative communication between the vacuum pump and a leading edge of the blood, and in the second position, the directional valve establishes an operative communication between the vacuum pump and the analyzer calibration fluid pouch.

8. A cartridge comprising:

a cartridge body comprising an upper surface and a lower surface;

a sample inlet portion located on the upper surface, the sample inlet portion comprising:
 a sample storage well comprising a top portion for receiving a blood sample and a bottom portion for releasing at least a portion of the blood sample into a sample storage conduit, wherein the area of the top portion is substantially larger than the area of the bottom portion;
 an air bladder exit port;
 a flat surface of the cartridge body, the flat surface of the cartridge body surrounding the top portion of the sample storage well and the air bladder exit port;

an optical chamber for generating one or more signals during sample interrogation, the one or more signals used to calculate one or more properties of the blood sample;

the sample storage conduit for transferring some, or all, of the at least a portion of the blood from the sample storage well to the optical chamber;

an air bladder for generating pressurized air, the air bladder operatively connected with the air bladder exit port;

a vent for relieving pressure in the optical chamber;

a cap hingedly connected to the cartridge body via a hinge, the cap having a top side and an underside, wherein at least a portion of the underside comprises a cap flat surface;

wherein, the cartridge is adjustable between an unsealed configuration and a sealed configuration by rotating the cap about the hinge;

in the unsealed configuration the sample storage well is configured to receive the blood sample; and in the sealed configuration a portion of the flat surface of the cartridge body mates with a portion of the cap flat surface to form a closed air passage operatively connecting the air bladder exit port to the sample storage well so that when the air bladder is squeezed pressurized air from the air bladder exit port is transferable to the sample storage well, wherein the closed air passage is facilitated by a groove set into the upper surface of the cartridge body, a recess set into the underside of the cap, or a combination thereof, wherein when the air bladder is squeezed some, or all, of the at least a portion of the blood is urged from the sample storage well towards the optical chamber.

9. The cartridge of claim 8, wherein the top portion of the sample storage well comprises a boss for increasing storage capacity of the sample storage well and wherein the cap rotates about the hinge in a plane substantially orthogonal to a plane generally defined by the upper surface.

10. The cartridge of claim 8, wherein the cartridge further comprises one of an enlarged cavity disposed in the sample storage conduit, and a hydrophobic insert adjacent to and aligned with the sample storage conduit, and the sample storage well further comprising internal walls, the internal walls of the sample storage well characterized as being more wettable than a surface of the sample storage conduit.

11. The cartridge of claim 8, wherein the cartridge further comprises a biosensor chamber, the biosensor chamber disposed between, and in operative communication with the optical chamber and the vent, and wherein the biosensor chamber comprises one or more biosensors for generating one or more signals used to calculate an additional one or more properties of the blood sample, and a biosensor chamber exit.

12. The cartridge of claim 11, further comprising a calibration fluid pouch in operative communication with the biosensor chamber, the calibration fluid pouch containing calibration fluid for calibrating the one or more biosensors.

13. The cartridge of claim 12, further comprising a blood flow path beginning at the sample storage well and ending at a point between the biosensor chamber exit and the vent, a calibration fluid flow path beginning at the calibration fluid pouch and ending at a point between the biosensor chamber exit and the vent, a junction where the blood flow path and the calibration fluid flow path intersect, and a directional valve disposed at the junction, the directional valve movable from a first position to a second position, wherein in the first position the directional valve permits movement of the calibration fluid along the calibration fluid flow path, and in the second position, the directional valve permits movement of at least a portion of the blood along the blood flow path.

14. The cartridge of claim 8, wherein the sample storage conduit comprises an enlarged cavity.

15. The cartridge of claim 8, wherein the sample storage conduit comprises at least one reagent.

16. The cartridge of claim 15, wherein the sample storage conduit comprises a mixing chamber.

17. A cartridge comprising:

a cartridge body comprising an upper surface and a lower surface;

a sample storage well disposed at the upper surface and comprising a top portion for receiving a blood sample and a bottom portion for releasing at least a portion of the blood sample into a sample storage conduit, wherein the area of the top portion is substantially larger than the area of the bottom portion;

an optical chamber for generating one or more signals during sample interrogation, the one or more signals used to calculate one or more properties of the blood sample;

the sample storage conduit for transferring some, or all, of the at least a portion of the blood from the sample storage well to the optical chamber;

a cartridge exit duct operatively connected to the optical chamber, the cartridge exit duct comprising a vacuum sealing member for frictionally engaging an outer surface of a vacuum hollow needle so that negative pressure from a vacuum pump associated with an analyzer is transferable to the cartridge exit duct; and a cap hingedly connected to the cartridge body via a hinge, the cap having a top side and an underside; wherein the cartridge is adjustable between an open configuration and a closed configuration by rotating the cap about the hinge;

in the open configuration the sample storage well is configured to receive the blood sample; and in the closed configuration, the sample storage well is covered with the cap, the cap further comprising a cap vent for subjecting the blood sample in the sample storage well to atmospheric pressure, whereby some, or all, of the at least a portion of the blood flows from the sample storage well towards the cartridge exit duct when the cartridge exit duct is under negative pressure.

18. The cartridge of claim 17, wherein the top portion of the sample storage well comprises a boss for increasing the sample storage well storage capacity, and wherein the cap rotates vertically about the hinge in a plane substantially orthogonal to a plane generally defined by the upper surface.

19. The cartridge of claim 17, wherein the cartridge further comprises one of an enlarged cavity disposed in the sample storage conduit, and a hydrophobic insert adjacent to and aligned with the sample storage conduit, and the sample storage well further comprising internal walls, the internal walls of the sample storage well characterized as being more wettable than a surface of the sample storage conduit.

20. The cartridge of claim 17, wherein the cartridge further comprises a biosensor chamber, the biosensor chamber disposed downstream of, and operatively connected to, the optical chamber, the biosensor chamber comprising one or more biosensors for generating one or more signals used to calculate an additional one or more properties of the blood sample and a biosensor chamber exit.

21. The cartridge of claim 20, further comprising:
a calibration duct comprising an internal segment of the calibration duct and a calibration sealing member, the calibration sealing member for frictionally engaging an outer surface of an analyzer calibration fluid dispensing needle, when the cartridge is connected with the analyzer, so that calibration fluid is transferable from an analyzer calibration fluid pouch located in the analyzer, to the internal segment of the calibration duct;
a calibration fluid flow path beginning at the internal segment of the calibration duct and ending at a point between the biosensor chamber exit and the cartridge exit duct, a blood flow path beginning at the sample storage well and ending at a point between the biosensor chamber exit and the cartridge exit duct, and a junction where the calibration fluid path intersects with the blood flow path; and
a directional valve disposed at the junction, for establishing operative communication between the vacuum pump and a leading edge of the at least a portion of the blood, and for establishing operative communication between the vacuum pump and the analyzer calibration fluid pouch.

22. The cartridge of claim 17, further comprising at least one reagent in the sample storage conduit.

23. A method for measuring blood coagulation of a blood sample comprising:
providing a system comprising a disposable cartridge, an analyzer, and one of a positive pressure means for regulating flow of at least a portion of the blood sample in the cartridge, and a negative pressure means for regulating flow of at least a portion of the blood sample in the cartridge;
the cartridge comprising:
a cartridge body having an upper surface and a lower surface;
a sample storage well comprising a top portion for receiving the blood sample and a bottom portion for releasing at least a portion of the blood sample into a sample storage conduit, wherein the area of the top portion is substantially larger than the area of the bottom portion;
an optical chamber for generating one or more signals during sample interrogation; and
the sample storage conduit further comprising one or more than one reagent, the sample storage conduit fluidly connecting the sample storage well and the optical chamber;
the analyzer comprising:
a receptor for receiving the cartridge;
a source of electromagnetic radiation (EMR) for interrogating contents of the optical chamber;
a spectrometer comprising a grating for dispersing the EMR emerging from at least a portion of the blood sample in the optical chamber, into component wavelengths, to produce dispersed EMR;
a one-dimensional multi-channel detector for receiving the dispersed EMR from the grating and producing the one or more that one signals; and
one or more processors for controlling the analyzer and processing the one or more than one signals received by the spectrometer;
receiving the blood sample in the sample storage well;
establishing a flow of at least a portion of the blood sample within the sample storage conduit;
mixing the one or more reagents with at least a portion of the blood sample to produce a mixture;
filling the optical chamber with at least some of the mixture;
interrogating the mixture in the optical chamber with the EMR in a temporal manner to produce a set of temporal optical measurements over a range of wavelengths and over a range of time;
preparing a primary two-dimensional matrix of the set of temporal optical measurements;
preparing a secondary two-dimensional matrix comprising a subset of optical measurements for a plurality of selected wavelengths obtained from the range of wavelengths, and a plurality of selected times obtained from the range of time;
calculating correlation coefficients for subsequent pairs of optical measurements from the secondary two-dimensional matrix;
using the calculated correlation coefficients for generating an order derivative of a temporal correlation coefficient curve; and
applying predefined criteria to the order derivative of a temporal correlation coefficient curve identifying at which selected time a coagulation process begins and at which selected time the coagulation process ends to determine a specific blood coagulation time; and
reporting the specific blood coagulation time.

24. The method of claim 23, wherein the order derivative of the set of calculated temporal correlation coefficients is one of a zero, a first and a second order derivative.

25. The system of claim 1, wherein the sample storage well is a separate structure inserted in the cartridge body as a sample storage well insert, wherein the wettability property of the sample storage well is greater than the wettability property of the rest of the cartridge body.

26. The cartridge of claim 8, wherein the sample storage well is a separate structure inserted in the cartridge body as a sample storage well insert, wherein the wettability property of the sample storage well is greater than the wettability property of the rest of the cartridge body.

27. The cartridge of claim 17, wherein the sample storage well is a separate structure inserted in the cartridge body as a sample storage well insert, wherein the wettability property of the sample storage well is greater than the wettability property of the rest of the cartridge body.

* * * * *